United States Patent
Zhao et al.

(10) Patent No.: US 12,358,925 B2
(45) Date of Patent: Jul. 15, 2025

(54) TARGETED UBIQUITINATION DEGRADATION BRD4 PROTEIN COMPOUND, PREPARATION METHOD THEREFOR AND APPLICATION THEREOF

(71) Applicant: CSPC ZHONGQI PHARMACEUTICAL TECHNOLOGY (SHIJIAZHUANG) CO., LTD., Shijiazhuang (CN)

(72) Inventors: Chuanwu Zhao, Shijiazhuang (CN); Chunhua Jiang, Shijiazhuang (CN); Yan Zhang, Shijiazhuang (CN); Xuejiao Zhang, Shijiazhuang (CN); Jinlu Yang, Shijiazhuang (CN); Jieqiong Kang, Shijiazhuang (CN); Peipei Zhao, Shijiazhuang (CN)

(73) Assignee: CSPC ZHONGQI PHARMACEUTICAL TECHNOLOGY (SHIJIAZHUANG) CO., LTD, Shijiazhuang (CN)

( * ) Notice: Subject to any disclaimer, the term of this patent is extended or adjusted under 35 U.S.C. 154(b) by 1018 days.

(21) Appl. No.: 17/427,845

(22) PCT Filed: Feb. 3, 2020

(86) PCT No.: PCT/CN2020/000027
§ 371 (c)(1),
(2) Date: Aug. 2, 2021

(87) PCT Pub. No.: WO2020/156017
PCT Pub. Date: Aug. 6, 2020

(65) Prior Publication Data
US 2022/0135589 A1    May 5, 2022

(30) Foreign Application Priority Data

Feb. 2, 2019 (CN) .......................... 201910106874.8

(51) Int. Cl.
| | | |
|---|---|---|
| C07D 471/14 | (2006.01) |
| A61K 47/55 | (2017.01) |
| A61K 47/62 | (2017.01) |
| A61K 47/66 | (2017.01) |
| A61P 25/00 | (2006.01) |
| A61P 35/00 | (2006.01) |
| C07D 471/04 | (2006.01) |
| C07D 475/00 | (2006.01) |
| C07D 487/04 | (2006.01) |
| C07D 495/04 | (2006.01) |
| C07D 495/14 | (2006.01) |

(52) U.S. Cl.
CPC .................. *C07D 495/14* (2013.01)

(58) Field of Classification Search
CPC .. C07D 471/14; C07D 471/04; C07D 495/04; C07D 487/04; C07D 495/14; C07D 475/00; A61K 47/55; A61K 47/62; A61K 47/66; A61P 35/00; A61P 25/00
See application file for complete search history.

(56) References Cited

U.S. PATENT DOCUMENTS 9,809,603 B1    11/2017  Jacques

FOREIGN PATENT DOCUMENTS

| | | |
|---|---|---|
| CN | 106458993 A | 2/2017 |
| CN | 107257800 A | 10/2017 |
| CN | 108136044 A | 6/2018 |
| CN | 108350062 A | 7/2018 |
| WO | 2017/024317 A3 | 2/2017 |

*Primary Examiner* — Bruck Kifle
(74) *Attorney, Agent, or Firm* — NKL Law; Bin Lu; Allen Xue

(57) ABSTRACT

A compound represented by formula (I) or a tautomer, optical isomer, deuterated substance, oxynitride, solvate, pharmaceutically acceptable salt or prodrug thereof can be used in preparing a pharmaceutical composition. The compound or the pharmaceutical composition can be used in the preparation a drug for the prevention and/or treatment of cancer, tumors, viral infections, depression, neurological disorders, trauma, age-related cataracts, organ transplant rejection or autoimmune diseases.

9 Claims, 1 Drawing Sheet

TARGETED UBIQUITINATION DEGRADATION BRD4 PROTEIN COMPOUND, PREPARATION METHOD THEREFOR AND APPLICATION THEREOF

FIELD OF THE INVENTION

The present invention relates to the technical field of medicine, particularly, to a novel compound targeting ubiquitination degradation BRD4 protein, a preparation method thereof, a pharmaceutical composition containing same and a use of the compound or the pharmaceutical composition in the preparation of medicines.

BACKGROUND OF THE INVENTION

Bromodomain and extra-terminal domain (BET) proteins contain 4 members, namely BRD2, BRD3, BRD4 and BRDT. BET proteins recognize acetylated chromatin through its bromodomain (BD) and participate in gene expression regulation. As a member of the BET family, BRD4 contains two bromodomains, namely BD1 and BD2. BDs are readers of chromatin, ie, BDs recruit chromatin regulatory proteins in the promoter region to regulate gene expression and suppression by interacting with the acetylated lysine at the tail of histones (Balasundaram Padmanabhan etc., Journal of Biosciences; 2016, 41(2):295). Bromodomain-containing protein 4 (BRD4) is a chromatin reading protein which recognize and bind acetylated lysine residues in histones, and plays a key role in cell division and epigenetic memory transmission of transcriptional regulation. In addition to BRD4, the mammalian BET family also contains three other members: BRD2, BRD3 and BRDT, which can regulate various cellular processes through the interaction between the bromodomains (CN106905347). BRD4 has become a potential therapeutic target on various human malignancies, including various solid tumors and hematological malignancies. PLX-2853 and AZD5153, as chemical molecular inhibitors of BRD4, are currently undergoing clinical trials for the treatment of related malignancies (NCT03297424, NCT03205176).

In mammalian cells, protein degradation is mainly carried out through ubiquitin-proteasome system to deal with damaged or excessive proteins. Ubiquitin can be attached to the substrate protein through a series of enzymatic reactions, resulting in a covalent bond between the C-terminal glycine of ubiquitin and the lysine residue of the substrate. Ubiquitin-marked proteins are eventually recognized and destroyed by the proteasome. Despite the high complexity of the ubiquitin system, some components or processes in the system can provide promising therapeutic targets for the treatment of various diseases, including cancer and neurological disorders. Recently, Proteolysis Targeted Chimeras (PROTACs) is to selectively degrade any protein by placing the target protein near the E3 ligase. PROTACs are becoming a promising strategy for targeting so-called "indestructible" proteins, such as estrogen-related receptor alpha, cellular retinoic acid binding protein and BRD4. The key technology of PROTACs is to construct bifunctional small molecules to achieve two connection strategies: one is to bind the target protein, and the other is to recruit E3 ligase. Therefore, PROTACs can simultaneously bind the target protein and E3 in the cell to ubiquitinate the target protein that cannot bind to E3, and then be recognized and degraded by the proteasome (Angew Chem Int Ed Engl., 2016, 55: 1966).

Clinical studies have shown that maintaining high concentrations of drugs for long-term to inhibit the target protein may lead to drug resistance, reduced drug efficacy, and even have serious side effects. However, degradation of target protein by PROTAC molecules is similar to catalytic process. PROTAC only binds to the target protein for a long enough time to complete the ubiquitin marking, while the drug can be reused, thus avoid using equimolar amount of drug. Therefore, designing bifunctional small molecule drugs is helpful to reduce the drug dose and reduce side effects.

ARV-825 is a PROTAC compound that links the BRD4 inhibitor OTX015 with the phthalimide family by using the PROTACs technology, the phthalimide family can be combined with the E3 ubiquitin ligase complex component cereblon (CRBN) to successfully target and degrade the oncoprotein BRD4. The phthalimide family, including thalidomide and its derivatives such as lenalidomide and pomalidomide, can bind to cereblon (CRBN), and theoretically can bind E3 ligase to the target protein, and then degrade the target protein. Other BRD4-targeted PROTACs structures, such as dBET1, ARV-771 and BETd-246 have also been reported, which indicates that the BRD4-targeted PROTACs technology may be used as a research approach for druggability.

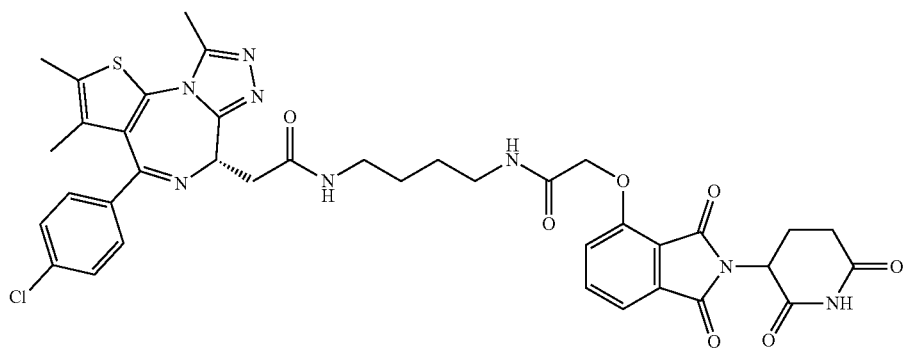

dBET1

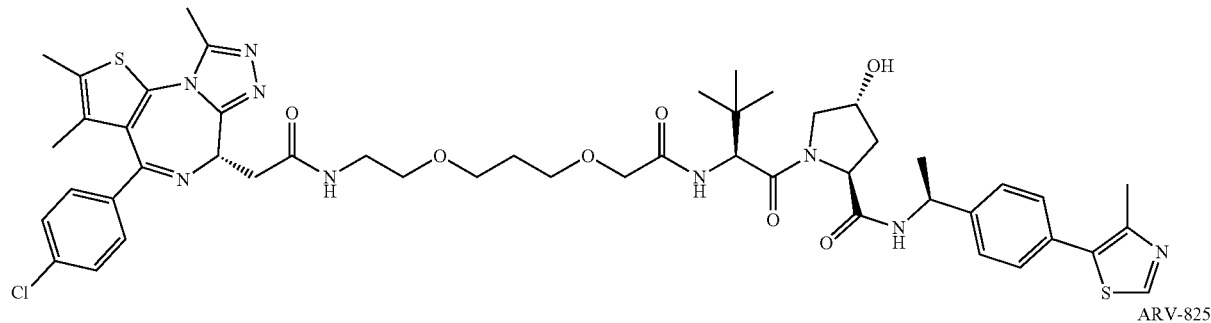

ARV-771

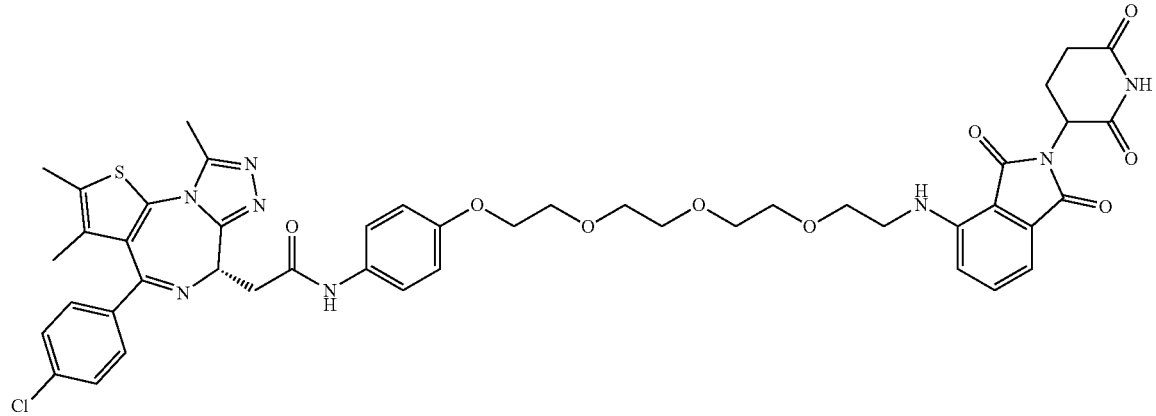

ARV-825

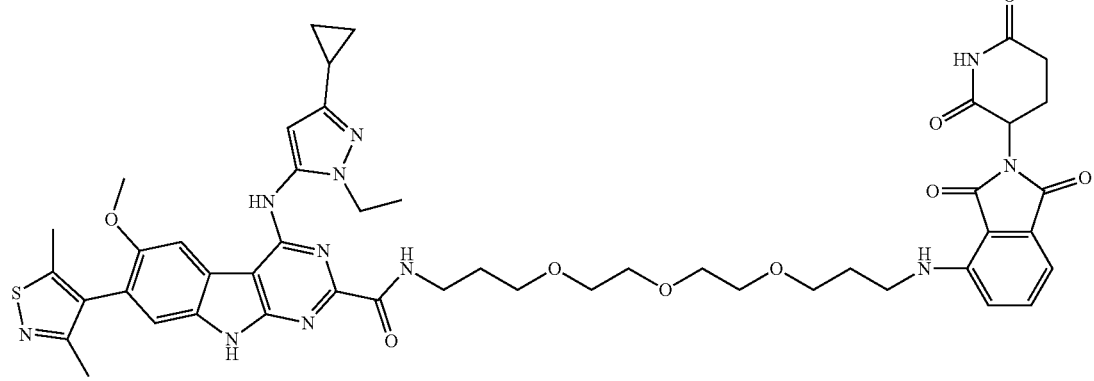

BETd-246

SUMMARY OF THE INVENTION

The present invention provides a class of novel compounds which can ubiquitin degrade the BRD4 protein based on PROTAC targeted protein degradation technology. They can be used to treat various tumor diseases, including various solid tumors and hematological malignancies. Specifically, the present invention relates to a compound of formula (I), a preparation method thereof, a pharmaceutical composition containing the compound, and the use of the compound or the pharmaceutical composition in the preparation of medicines.

In one aspect, a compound of formula (I) or a tautomer, optical isomer, deuterated substance, oxynitride, solvate, pharmaceutically acceptable salt or prodrug thereof is provided;

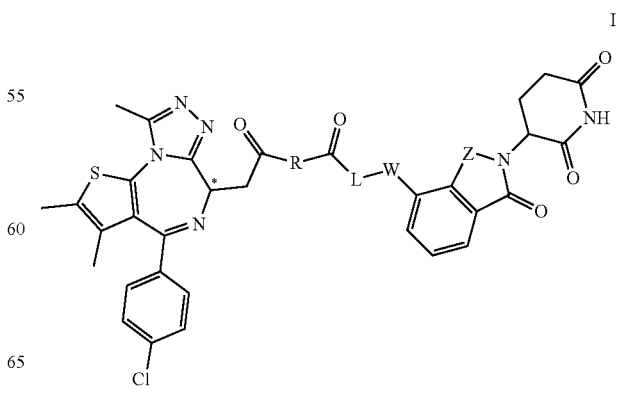

I wherein,
R is

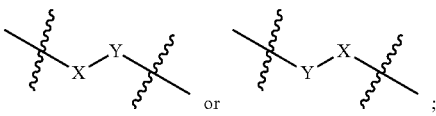

X is amino or substituted amino, and the substituent is selected from $C_{1-6}$ alkyl and $C_{1-6}$ alkoxy;
Y is amino, substituted or unsubstituted saturated 5-7 membered heterocycloalkyl, saturated heteromonospirocycloalkyl, saturated heterofused cycloalkyl or heteroaryl;
the saturated 5-7 membered heterocycloalkyl has heteroatoms selected from O, N and S, wherein the number of N heteroatom is 1, 2, or 3, and the number of O or S heteroatom is 0, 1, or 2, the substituted saturated 5-7 membered heterocycloalkyl means that the saturated 5-7 membered heterocycloalkyl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;
the saturated heteromonospirocycloalkyl has heteroatoms selected from O, N and S, wherein the number of N heteroatom is 1, 2 or 3, the number of O or S heteroatoms is 0, 1, or 2, and the saturated heteromonospirocycloalkyl is selected from the group consisting of 3-membered/5-membered, 4-membered/4-membered, 4-membered/5-membered, 4-membered/6-membered, 5-membered/5-membered, and 5-membered/6-membered ring, the substituted saturated heteromonospirocycloalkyl means that the saturated heteromonospirocycloalkyl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;
in addition to carbon atoms, the saturated heterofused cycloalkyl contains one or two heteroatoms independently selected from O, N and S, and the saturated heterofused cycloalkyl is selected from the group consisting of 5-membered/5-membered and 5-membered/6-membered bicyclic fused heterocyclic group, the substituted saturated heterofused cycloalkyl means that the saturated heterofused cycloalkyl is independently substituted with one or more substituents selected from halogen, hydroxy, cyano, nitro, amino, carbonyl, $C_{1-4}$ alkoxy, $C_{1-4}$ alkyl, $C_{3-8}$ cycloalkyl, aryl and $C_{5-7}$ heteroaryl;
in addition to carbon atoms, the heteroaryl group contains one or two heteroatoms independently selected from O, N and S, the substituted heteroaryl means that the heteroaryl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;
L is —$(CH_2)_n$—, —$CH_2CH_2(OCH_2CH_2)_m$— or —$CH_2R_1$—;
n is 1, 2, 3, 4, 5 or 6;
m is 1, 2, 3 or 4;
$R_1$ is optionally substituted cycloalkyl, heterocycloalkyl, haloheterocycloalkyl, aryl or heteroaryl; the substituent is independently selected from one or more groups consisting of halogen, hydroxyl, cyano, nitro, $C_{1-6}$ alkyl, $C_{1-6}$ alkoxy, haloheterocycloalkyl, aryl and heteroaryl;
W is —$CH_2$—, —NH—, —O—, —CONH— or —COO—;
Z is —$CH_2$— or —CO—.
In some embodiments,
R is

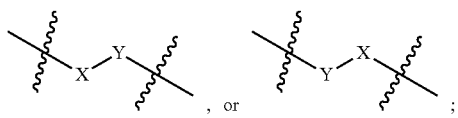

X is amino or substituted amino, and the substituent is $C_{1-6}$ alkyl and $C_{1-6}$ alkoxy;
Y is amino, substituted or unsubstituted saturated 5-7 membered heterocycloalkyl, saturated heteromonospirocycloalkyl, saturated heterofused cycloalkyl or heteroaryl;
the substituted or unsubstituted saturated 5-7 membered heterocycloalkyl has heteroatoms selected from O, N and S, wherein the number of N heteroatom is 1, 2, or 3, and the number of 0 or S heteroatom is 1, or 2, the substituted saturated 5-7 membered heterocycloalkyl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;
the substituted or unsubstituted saturated heteromonospirocycloalkyl has heteroatoms selected from O, N and S, wherein the number of N heteroatom is 1, 2 or 3, the number of O or S heteroatoms is 1, or 2, and the saturated heteromonospirocycloalkyl is selected from the group consisting of 3-membered/5-membered, 4-membered/4-membered, 4-membered/5-membered, 4-membered/6-membered, 5-membered/5-membered, and 5-membered/6-membered ring, which is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;
in addition to carbon atoms, the substituted or unsubstituted saturated heterofused cycloalkyl contains one or two heteroatoms independently selected from O, N and S, and the saturated heterofused cycloalkyl is selected from the group consisting of 5-membered/5-membered and 5-membered/6-membered bicyclic fused heterocyclic group, and the substituted saturated heterofused cycloalkyl is independently substituted with one or more substituents selected from halogen, hydroxy, cyano, nitro, amino, carbonyl, $C_{1-4}$ alkoxy, $C_{1-4}$ alkyl, $C_{3-8}$ cycloalkyl, aryl and $C_{5-7}$ heteroaryl;
in addition to carbon atoms, the heteroaryl group contains one or two heteroatoms independently selected from O, N and S, the heteroaryl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;
L is —$(CH_2)_n$—, —$CH_2CH_2(OCH_2CH_2)_m$— or —$CH_2R_1$—;
n is 1, 2, 3, 4, 5 or 6;
m is 1, 2, 3 or 4;

R₁ is optionally substituted cycloalkyl, heterocycloalkyl, haloheterocycloalkyl, aryl or heteroaryl; the substituent is independently one or more selected from group consisting of halogen, hydroxyl, cyano, nitro, $C_{1-6}$ alkyl, $C_{1-6}$ alkoxy, haloheterocycloalkyl, aryl and heteroaryl;

W is —CH₂—, amino, —O—, —CONH— or —COO—;

Z is —CH₂— or —CO—.

In some embodiments, X is amino; Y is amino, or substituted or unsubstituted saturated 5-7 membered heterocycloalkyl.

In some embodiments, X is amino; Y is amino, or piperazinyl.

In some embodiments, L is —(CH₂)$_n$—, —CH₂CH₂(OCH₂CH₂)$_m$—; n is 1, 2, 3, 4, 5 or 6; m is 1, 2, 3 or 4.

In some embodiments, the compound of the present invention is compound of formula (II) or a tautomer, deuterated compound, oxynitride, solvate, pharmaceutically acceptable salt or prodrug thereof:

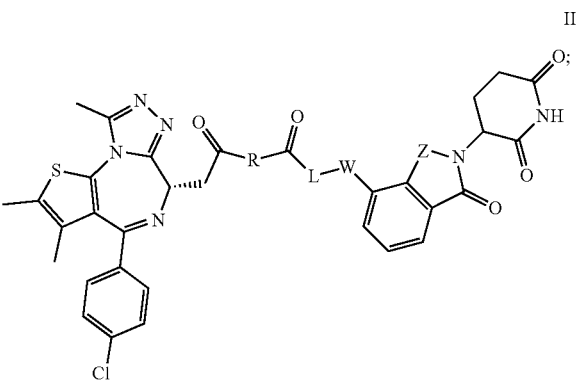

II wherein, R, L, W and Z are as defined above.

In some embodiments, the compound of the present invention contains the following specific compound, or tautomer, optical isomer, deuterated compound, oxynitride, solvate, pharmaceutically acceptable salt or prodrug thereof:

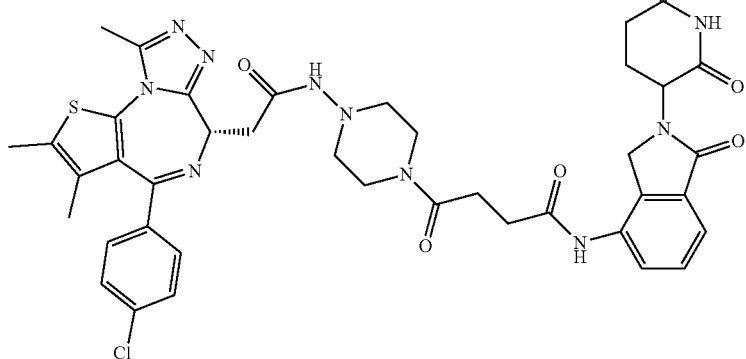

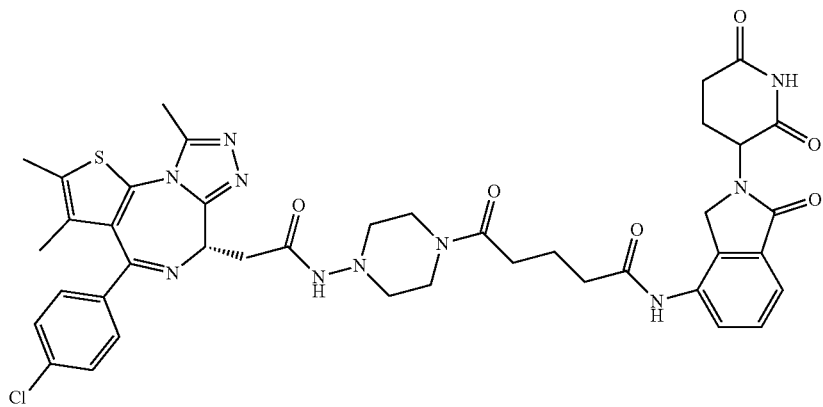

-continued
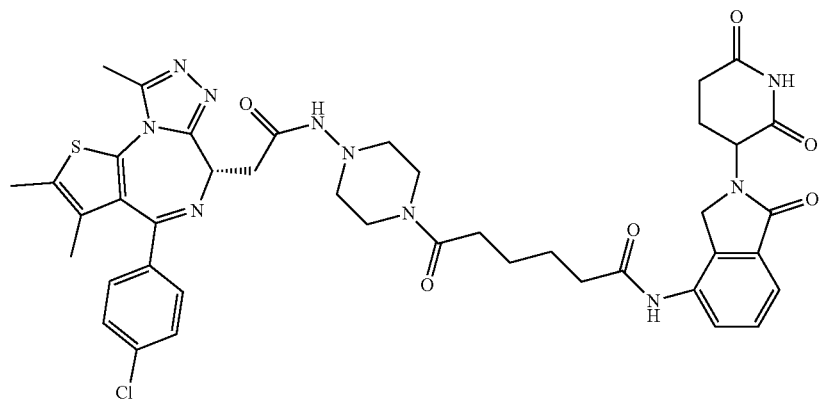
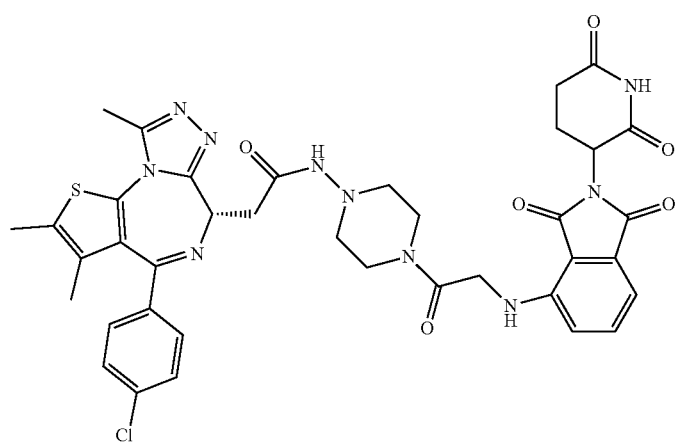
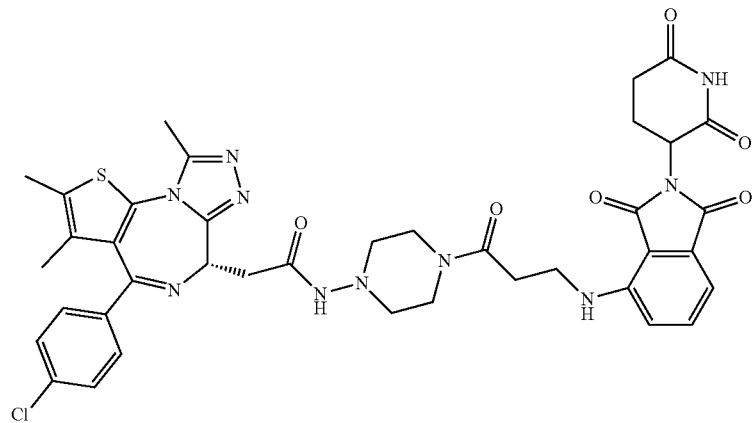
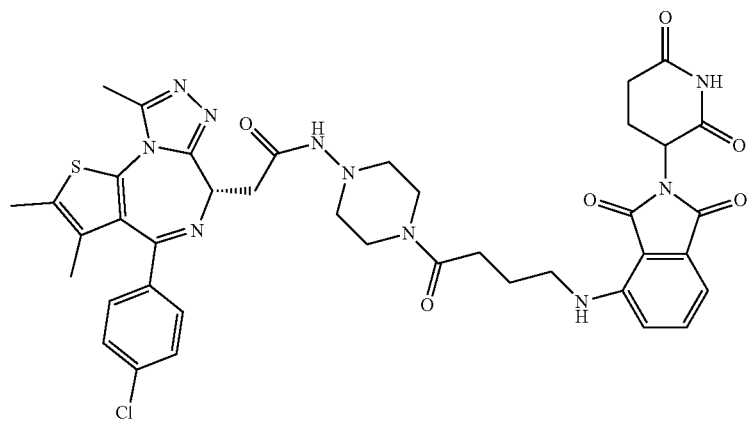

-continued
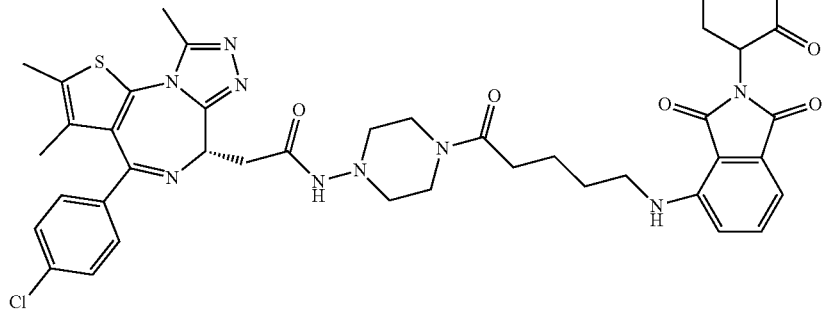
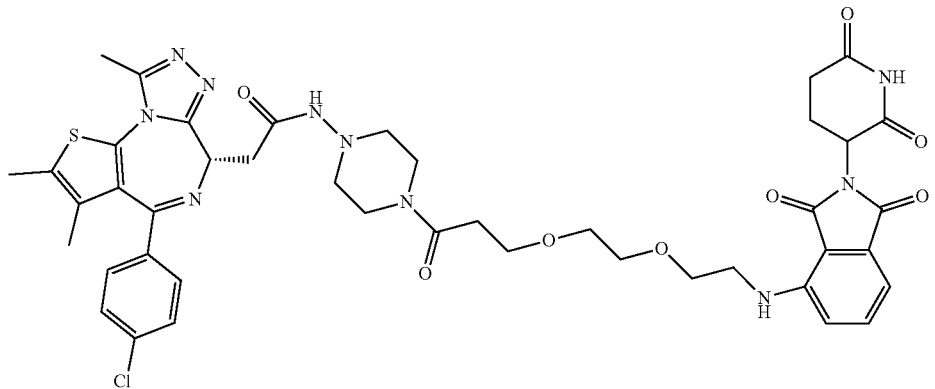
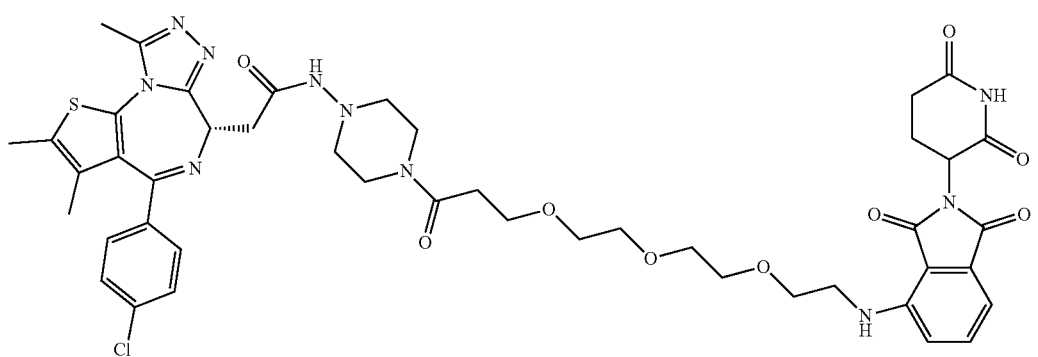
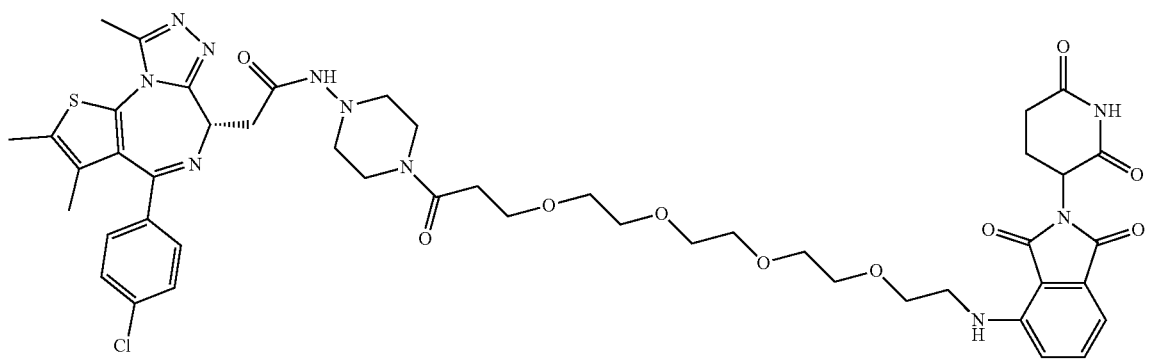

-continued
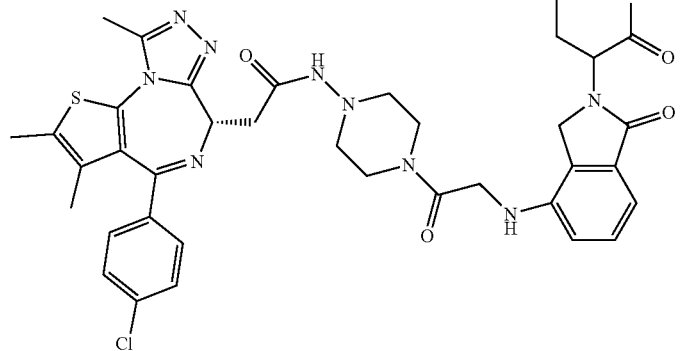
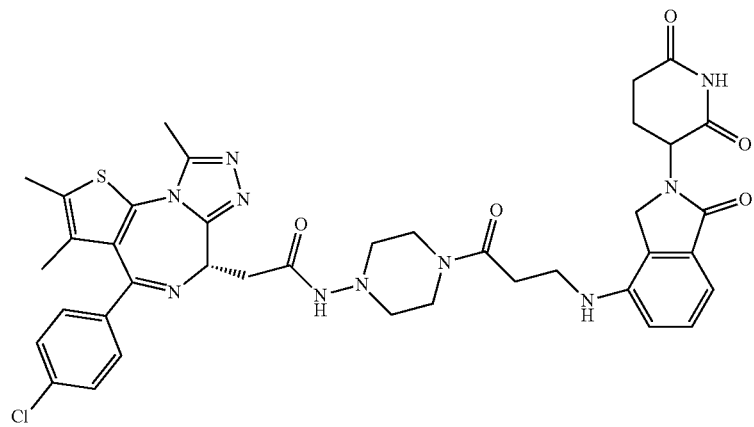
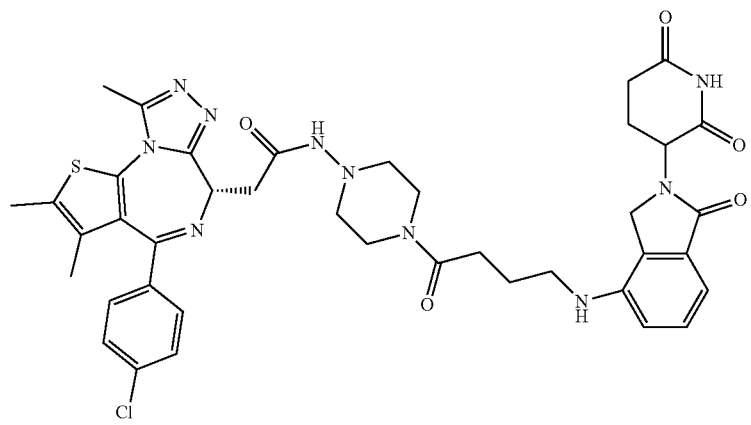
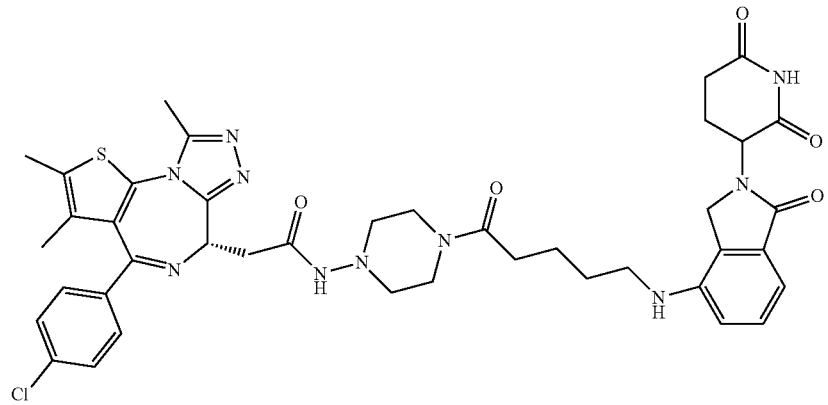

-continued
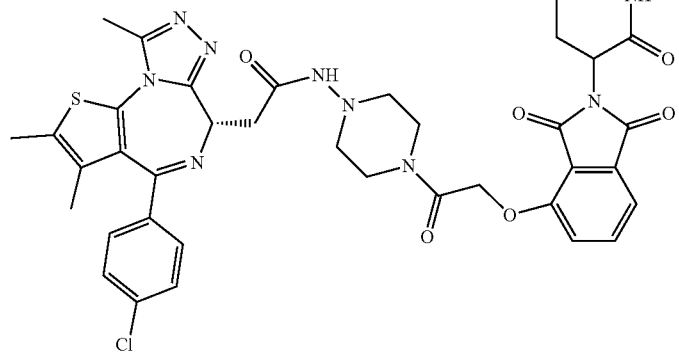
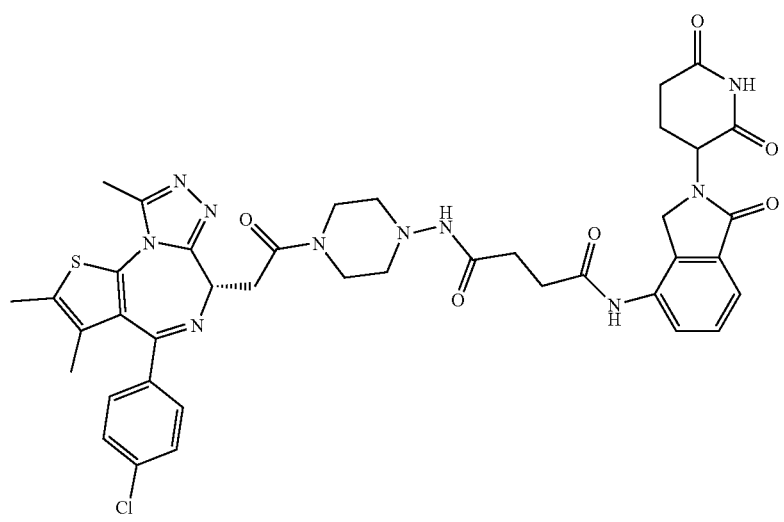
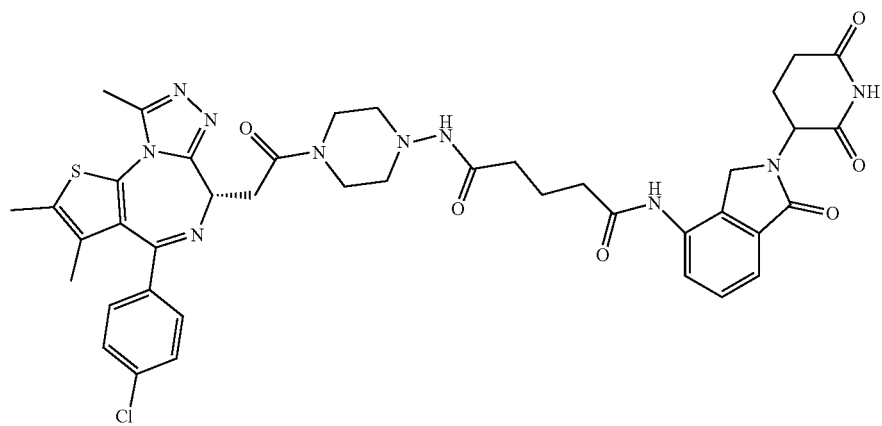

-continued
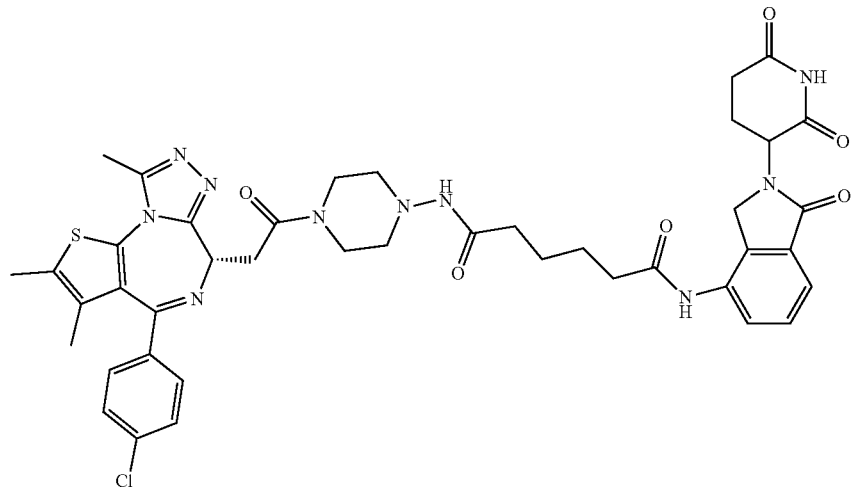
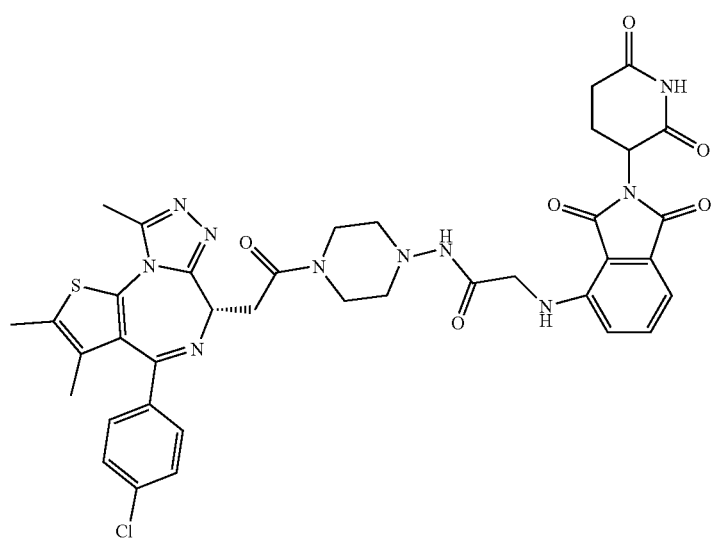
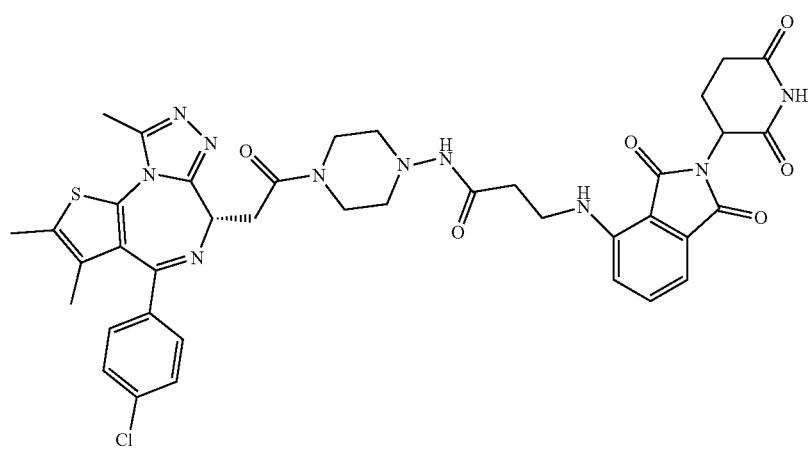

-continued
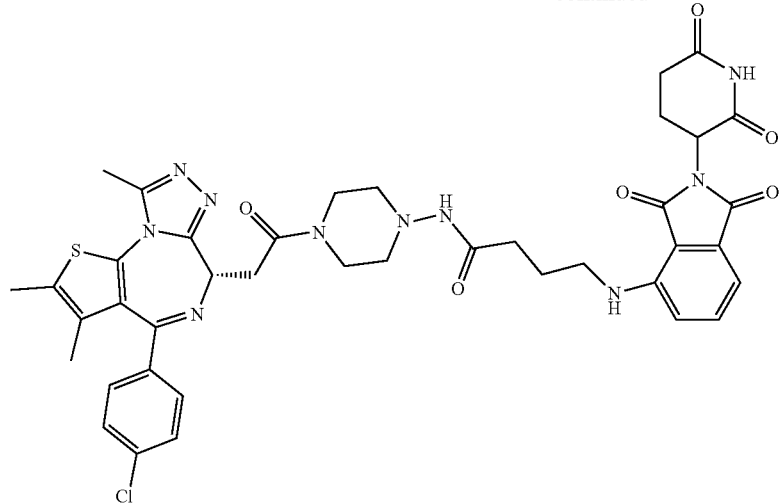
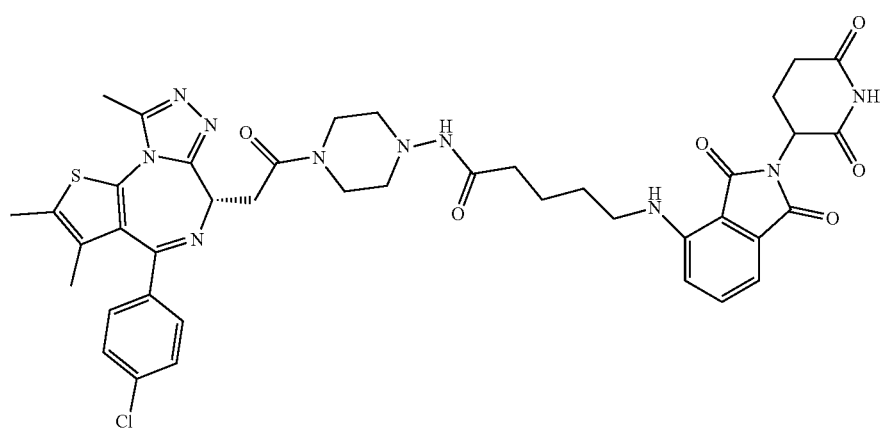
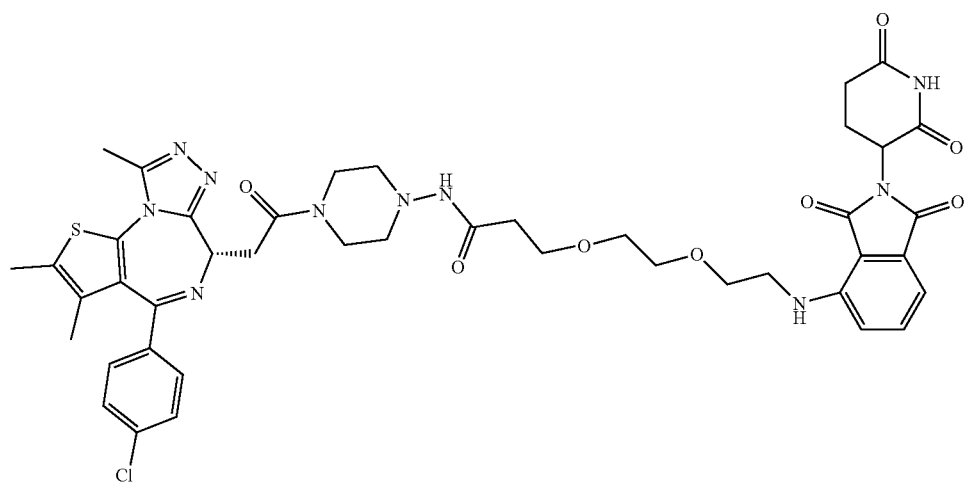

-continued
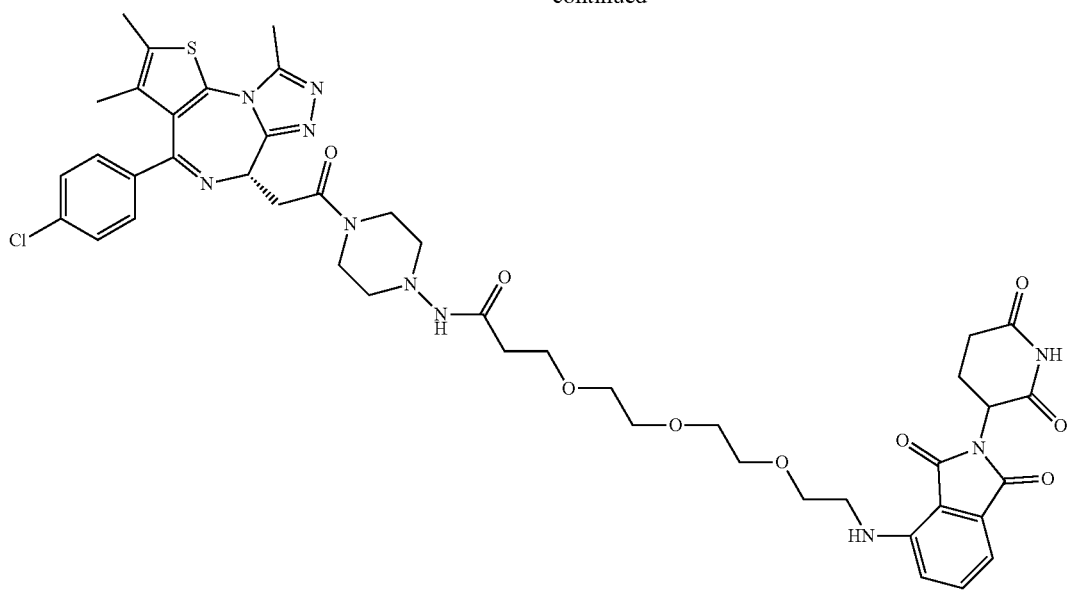
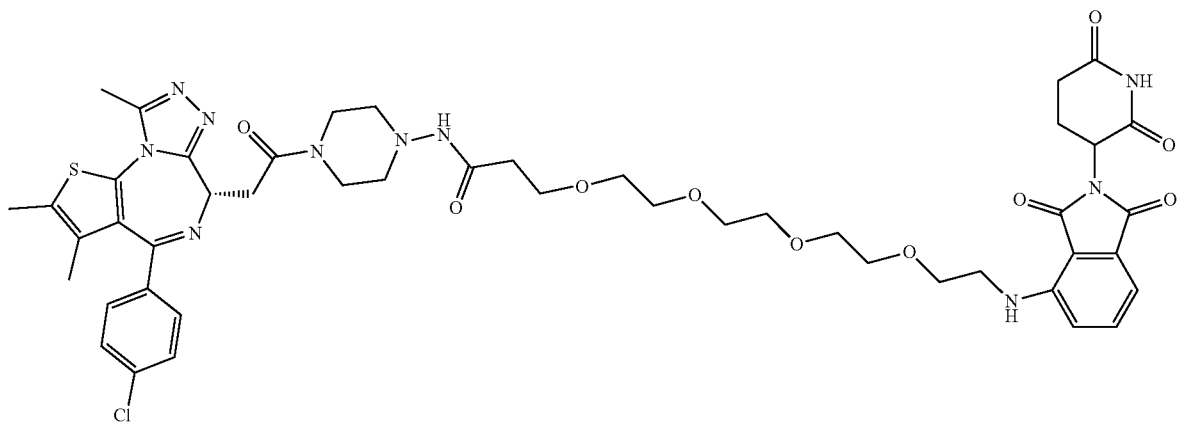
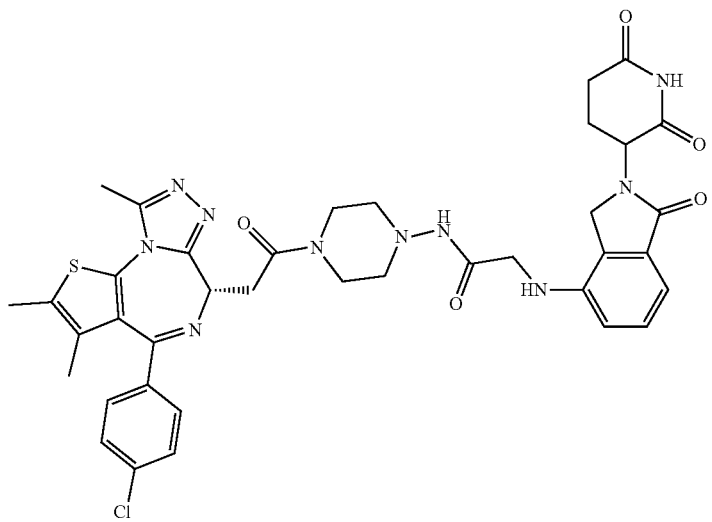

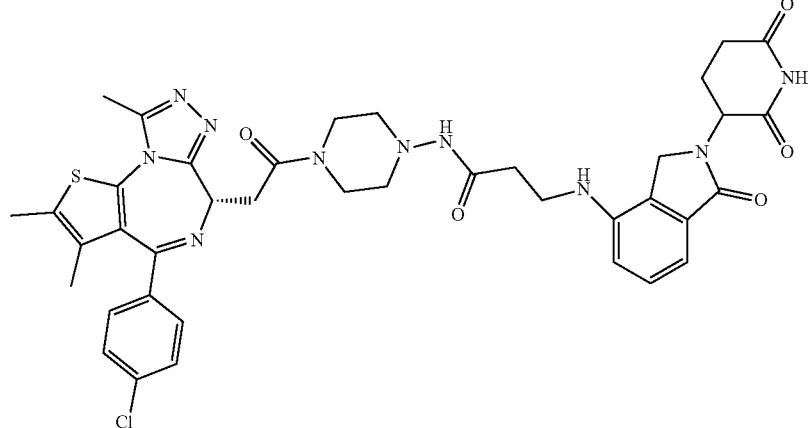
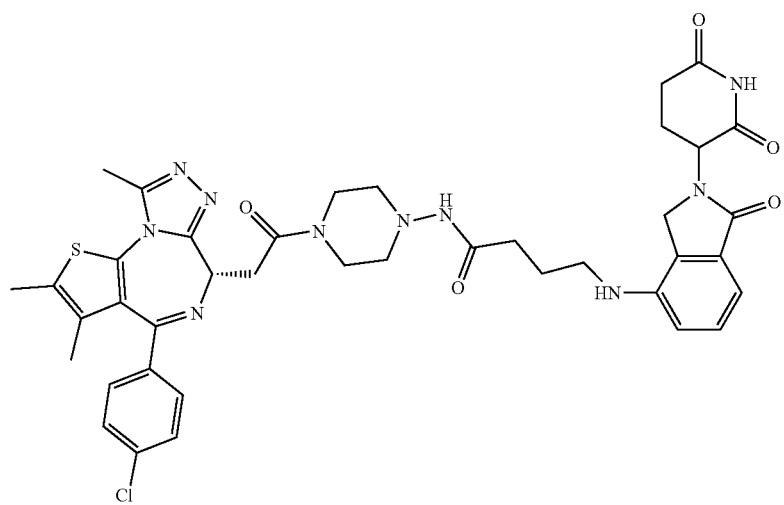
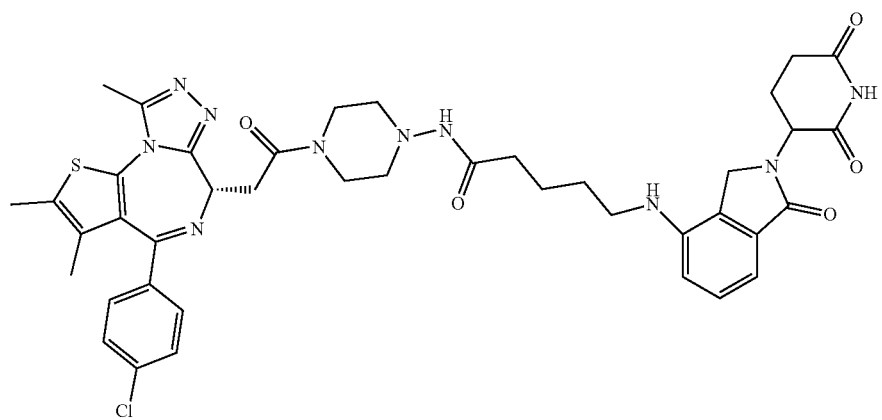

-continued
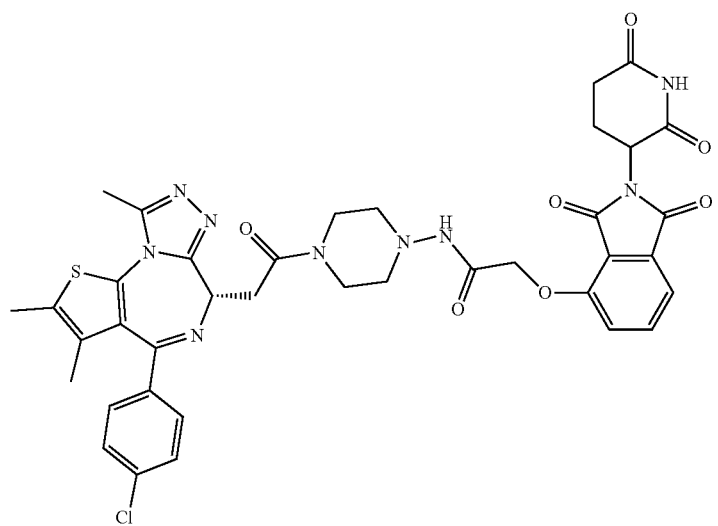
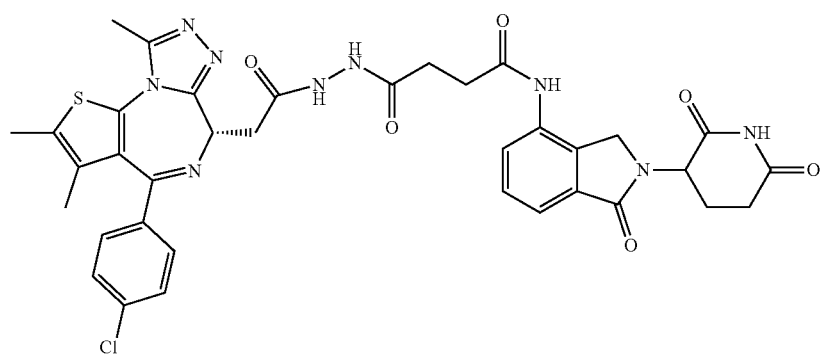
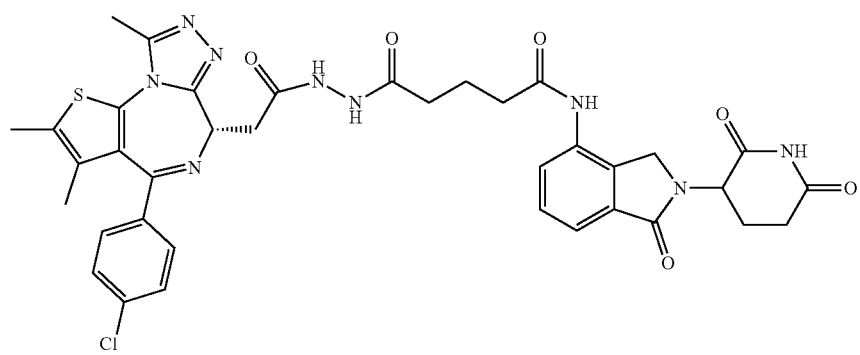
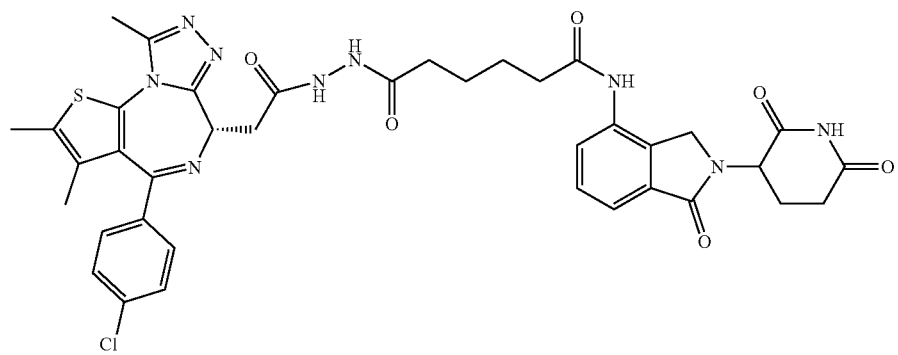

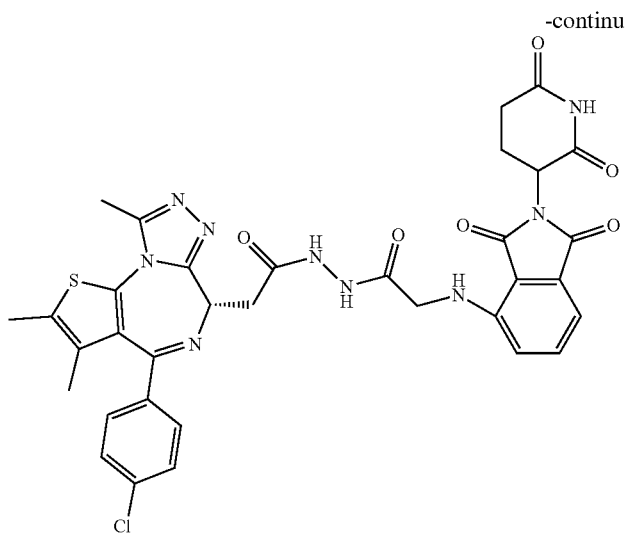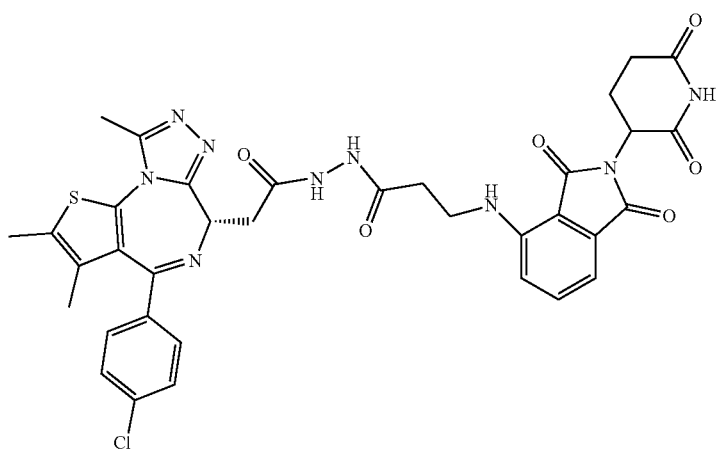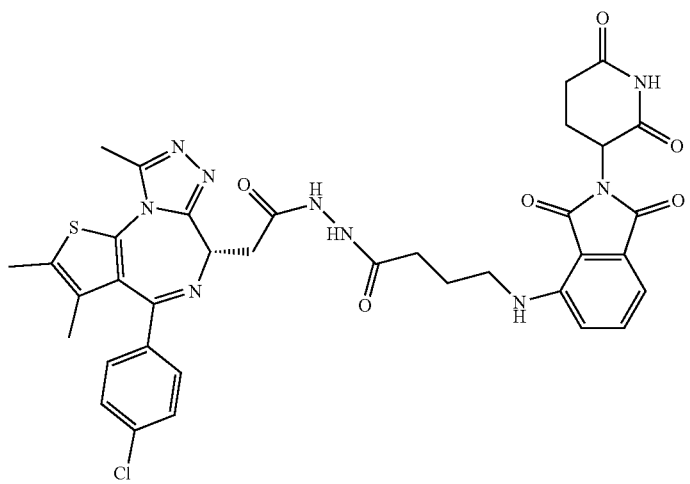

-continued
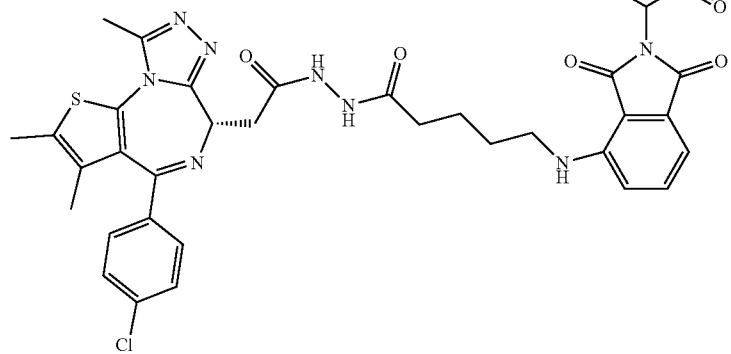
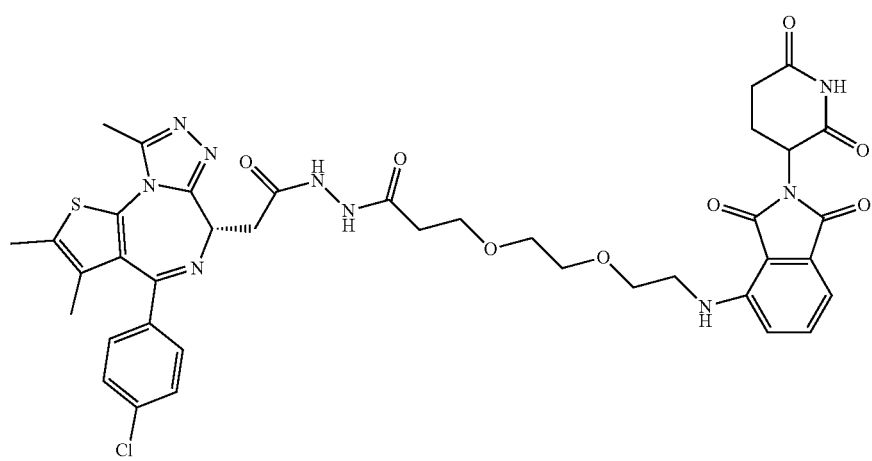
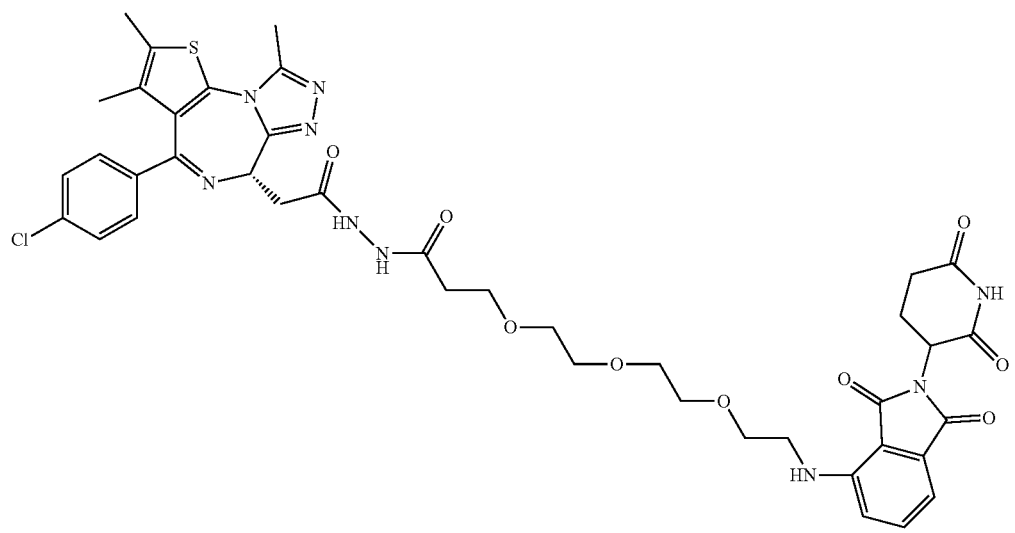

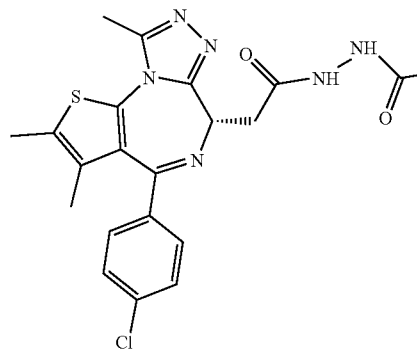
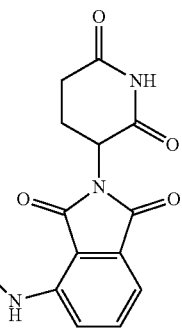
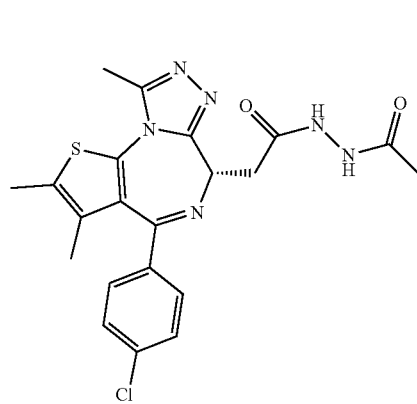
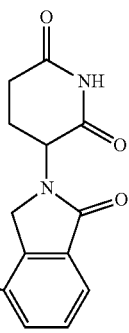
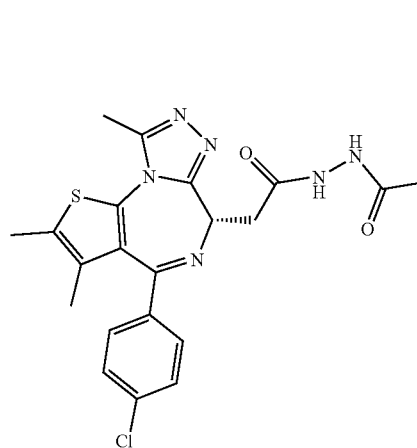
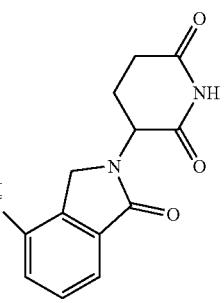

-continued

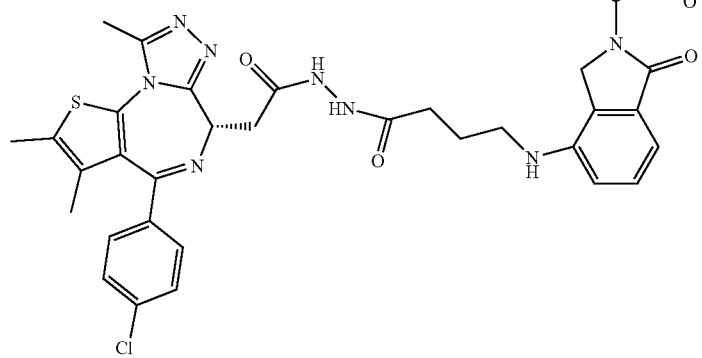

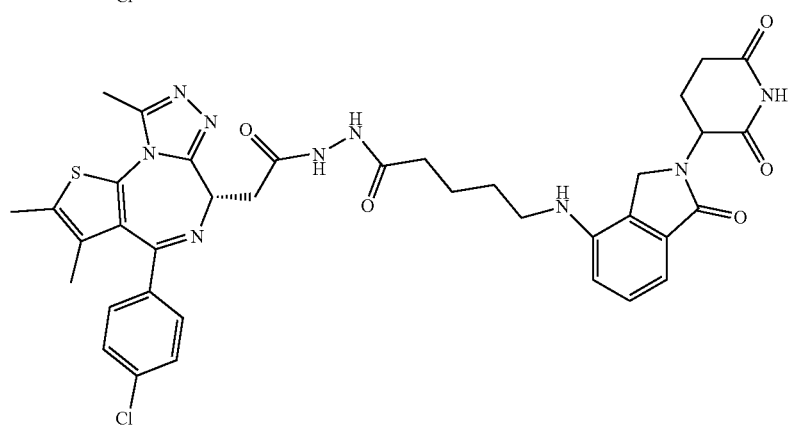

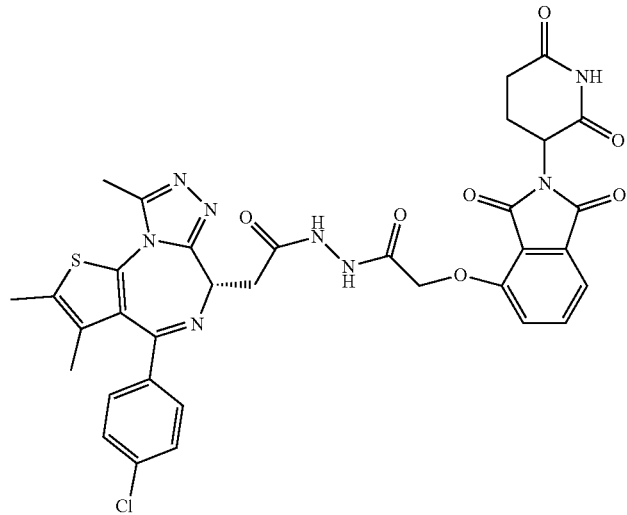

In another aspect, a pharmaceutical composition comprising the above-mentioned compound of formula (I) or a tautomer, optical isomer, deuterated substance, oxynitride, solvate, pharmaceutically acceptable salt or prodrug thereof is provided.

In another aspect, a use of the compound of formula (I) or a tautomer, optical isomer, deuterated substance, oxynitride, solvate, pharmaceutically acceptable salt or prodrug thereof in the preparation of medicine for the prevention and/or treatment of cancer, tumor, viral infections, depression, neurological disorders, trauma, age-related cataracts, organ transplant rejection or autoimmune diseases is provided; wherein, preferably, the cancer or tumor is selected from groups consisting of lung cancer, bone cancer, stomach cancer, pancreatic cancer, skin cancer, head and neck cancer, uterine cancer, ovarian cancer, testicular cancer, oviduct cancer, endometrial cancer, cervical cancer, vagina cancer, pancreatic cancer, brain cancer, pituitary adenoma, melanoma, epidermoid carcinoma, T-cell lymphoma, chronic and acute leukemia.

In another aspect, a method for preparing the compound of formula (I) or a tautomer, optical isomer, deuterated substance, oxynitride, solvate, pharmaceutically acceptable salt or prodrug thereof is provided, comprising subjecting the compound of formula (M) and the compound of formula (C) to condensation reaction to afford the compound of formula (I),

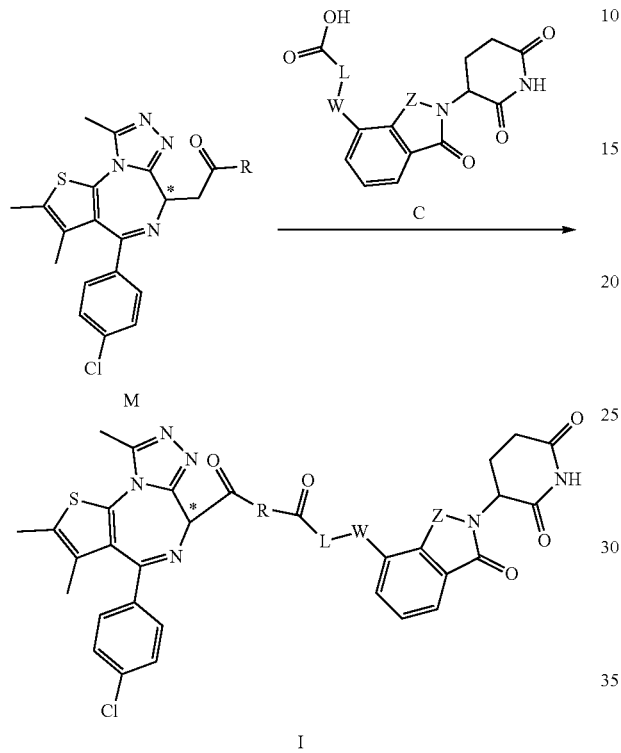

wherein, R, L, W and Z are as defined above.

Preferably, the reaction is carried out in organic solvent, the organic solvent is selected from one or more of tetrahydrofuran, acetonitrile, N,N-dimethylformamide, halogenated hydrocarbons, ethylene glycol dimethyl ether, dichloroethane, methanol, ethanol, petroleum ether, n-hexane, diethyl ether and ethyl acetate; preferably, the halogenated hydrocarbon is dichloromethane, dichloroethane, chloroform or tetrachloromethane.

The compound of formula (M) can be obtained by the following preparation method:

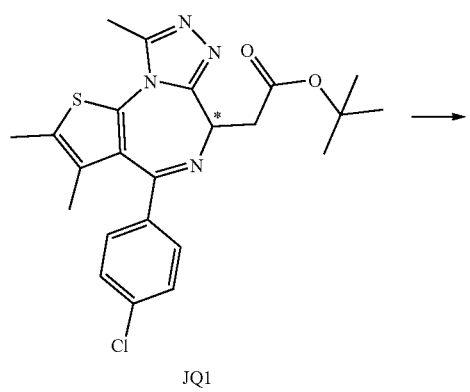

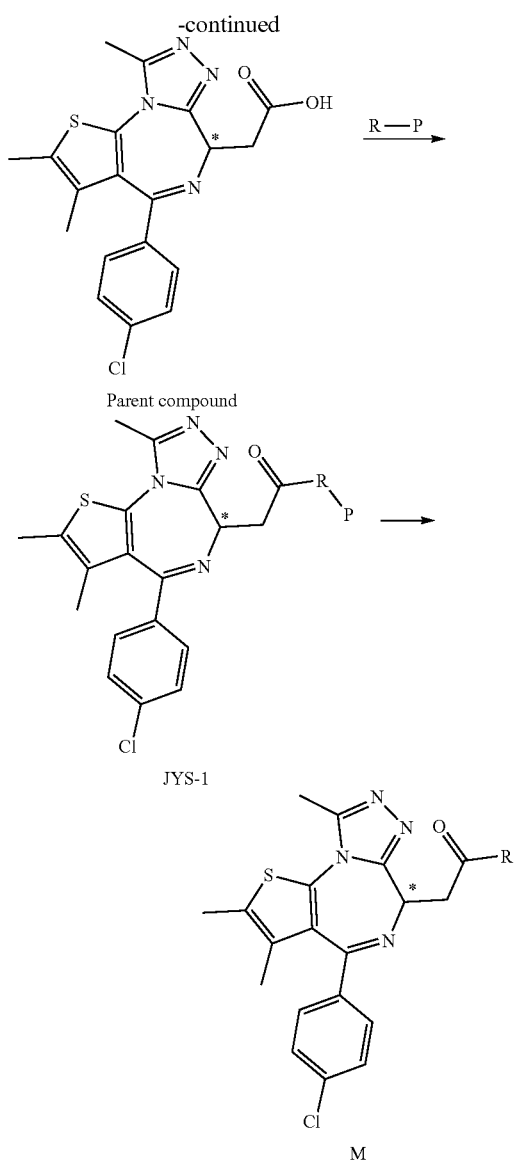

The preparation method comprises the following steps:
(1) Subjecting the compound of formula (JQ1) to ester hydrolysis reaction to obtain the parent compound;
(2) Subjecting the parent compound and the compound of formula (R-P) to acylation reaction to obtain the compound of formula (JYS-1);
(3) Deprotecting the compound of formula (JYS-1) to obtain the compound of formula (M).

Wherein, R, L, W, Z are as defined above;
P is an amino protecting group, the P is selected from the groups consisting of N-benzyloxycarbonyl (Cbz), tert-butoxycarbonyl (Boc), fluorenyl methoxycarbonyl (Fmoc), allyloxycarbonyl (Alloc), trimethylsilylethoxycarbonyl (Teoc), phthaloyl (Pht), trifluoroacetyl (Tfa), p-toluenesulfonyl (Tos), trityl (Trt), 2,4-dimethoxybenzyl (DMb) and p-methoxybenzyl (PMB), preferably tert-butoxycarbonyl (Boc);

Preferably, in the above steps (1)-(3), the reactions are all carried out in organic solvent, and the organic solvent is selected from one or more of tetrahydrofuran, acetonitrile, N,N-dimethylformamide, halogenated hydrocarbons, ethylene glycol dimethyl ether, dichloroethane, methanol, ethanol, petroleum ether, n-hexane, diethyl ether and ethyl acetate; preferably, the halogenated hydrocarbon is dichloromethane, dichloroethane, chloroform or tetrachloromethane.

Preferably, in the above steps (1) and (3), the reaction is carried out in acidic condition, and the acid is not limited to trifluoroacetic acid, formic acid, methanesulfonic acid, acetic acid, sulfuric acid or hydrochloric acid, preferably, the the acid is trifluoroacetic acid.

Preferably, in the above steps (2) and (3), the reaction is carried out in alkaline condition, and the alkaline is selected from one or more of triethylamine, diisopropylethylamine, piperidine, pyrrole, pyridine, dimethylpyridine and dimethylaminopyridine.

Definition and Detailed Description of Terms

The term "optional" or "optionally" means that the event or situation described later can but does not necessarily happen, and the description comprises the situation in which the event or situation happens and does not happen.

The term "alkyl" comprises $C_1$-$C_6$ alkyl, preferably $C_1$-$C_4$ alkyl, the alkyl can be linear or branched chain, or cycloalkyl, further comprising but not limited to methyl, ethyl, n-propyl, isopropyl, n-butyl, isobutyl, tert-butyl, cyclopropyl, cyclobutyl, cyclopentyl, cyclohexyl. The term also comprises all alkyl involved in alkyl groups such as alkoxy, halogen-substituted alkyl, etc.

The term "aryl" refers to the monovalent group after removing a hydrogen atom from the aromatic nucleus carbon of aromatic hydrocarbon molecule, comprising $C_6$-$C_{14}$ aromatic ring, and further comprising but not limited to phenyl and naphthyl.

The term "heteroaryl" refers to a monovalent group after removing a hydrogen atom from the aromatic nucleus carbon of heteroaryl compound molecule, wherein, the heteroatom is selected from N, O or S, comprising 5-14 membered heteroaromatic ring, the heteroaromatic ring can be a single ring or a fused ring, and can be partially unsaturated. The heteroaromatic ring also comprises a 5-membered or 6-membered nitrogen-containing heteroaromatic ring. The heteroaromatic ring comprises but is not limited to pyridine, pyrazine, pyridazine, pyrrole, imidazole, thiophene, furan. The aromatic ring and heteroaromatic ring can be further substituted by substituents.

The term "halogen" refers to fluorine (F), chlorine (Cl), bromine (Br) or iodine (I).

The term "substituted with one or more substituents" comprises but is not limited to substituted with one, two, three, or four substituents.

The compounds of the present invention comprises the compound or a tautomer, optical isomer, deuterated substance, oxynitride, solvate, pharmaceutically acceptable salt or prodrug thereof The salt of the compound of the present invention preferably comprises a pharmaceutically acceptable salt of the compound. The salt can be prepared by any suitable method in the literature, for example, inorganic acids are used such as hydrochloric acid, hydrobromic acid, sulfuric acid, and nitric acid, phosphoric acid; or organic acids are used such as acetic acid, maleic acid, succinic acid, mandelic acid, fumaric acid, malonic acid, pyruvic acid, oxalic acid, glycolic acid and salicylic acid; pyranonic acid such as glucuronic acid and galacturonic acid; α-hydroxy acid, such as citric acid and tartaric acid; amino acids, such as aspartic acid and glutamic acid; aromatic acids, such as benzoic acid and cinnamic acid; sulfonic acids, such as p-toluenesulfonic acid, ethylsulfonic acid.

In the present invention, solvate are those forms of the compound of the present invention, which form a complex through coordination with solvent molecules in a solid or liquid state. Hydrate is a special form of solvate in which the coordination is carried out with water. In the present invention, the preferred solvate is hydrate.

The term "prodrug" refers to compound which is converted into the aforementioned general formula or specific compound in vivo. Such conversion is affected by the hydrolysis of the prodrug in the blood or the enzymatic conversion of the prodrug into the parent structure in the blood or tissue. The prodrug of the present invention can be ester. In the existing invention, ester used as prodrug comprises phenyl ester, aliphatic ($C_{1-24}$) ester, acyloxymethyl ester, carbonate, carbamate, and amino acid ester. For example, a compound of the present invention contains hydroxyl/carboxyl, that is, it can be acylated to obtain compound in the form of prodrug. Other prodrug forms comprise phosphate ester, such these phosphate ester compounds are obtained by phosphorylation of the hydroxyl group on the parent compound.

In the present invention, desired pharmacological effects can be achieved by administering the pharmaceutical composition to patients in need thereof. For the purposes of the present invention, patients are mammals containing human in need of treating specific conditions or diseases.

In the present invention, the pharmaceutically acceptable carrier can be carrier that is relatively non-toxic and harmless to the patient at a concentration consistent with the effective activity of the active ingredient, so that any side effects caused by the carrier will not destroy the beneficial effects of the active ingredients. The pharmaceutically effective amount of the compound or pharmaceutically acceptable salt thereof is preferably an amount that produces results or effects on the specific condition being treated. Any effective conventional dosage unit form containing immediate release, sustained release and time-release formulations can be used, and the compound of the present invention can be administered together with a pharmaceutically acceptable carrier known in the art in the following manner: oral, parenteral, local, nasal cavity, eye, sublingual, rectal, vaginal administration, etc.

The compound of the present invention can be administered in a single agent or in combination with one or more other agents, wherein the combination does not cause unacceptable adverse reactions.

The Beneficial Effects of the Present Invention:

The present invention designs and synthesizes a series of BRD4 protein targeted degradatable PROTAC compound with aminopiperazine or hydrazine linker structure, which has good anti-tumor activity, and exhibits excellent BRD4 inhibitory effects, the compound shows better inhibitory activity, anti-proliferation and apoptosis-inducing ability compared with JQ1.

EMBODIMENTS FOR CARRYING OUT THE INVENTION

Figure 1:
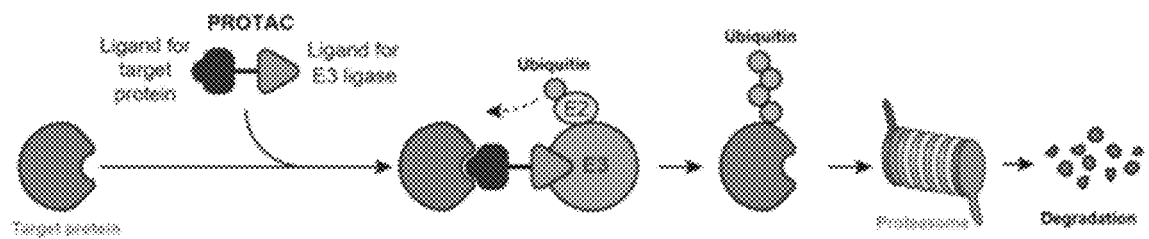
FIG. 1 shows the basic principle of PROTAC technology.

The preparation method of the present invention will be further described in detail below in conjunction with specific examples. It should be understood that the following examples are merely illustrative and explanation of the present invention, and should not be consider to limit the scope of protection of the present invention. All technologies implemented based on the above content of the present invention are covered within the scope of the present invention. Unless otherwise specified in the following examples, all temperatures are set in degrees Celsius. Unless otherwise specified, the raw material compounds are synthesized by the method described in present application or are commercially available, and are purchased from the following manufacturers: Bailingwei, Beijing Yinuokai Technology Co., Ltd., Aladdin reagent, Alfa Aesar, Shaoyuan Chemical Technology Co., Ltd. etc.

The abbreviations used in the Preparation Examples, Examples and elsewhere in present application are as follows:
DCM dichloromethane
DIPEA N,N-diisopropylethylamine
DMF N,N-dimethylformamide
EtOAc ethyl acetate
h hour
HATU O-(7-azabenzotriazol-1-yl)-N,N,N',N'-tetramethyluronium hexafluorophosphate
MeOH methanol
TFA trifluoroacetic acid Preparation Example 1

(6S)-4-(4-chlorophenyl)-2,3,9-trimethyl-6H-thieno[3,2-f][1,2,4]thiazolo[4,3-a][1,4]diazepine-6-acetic Acid (Parent Compound)

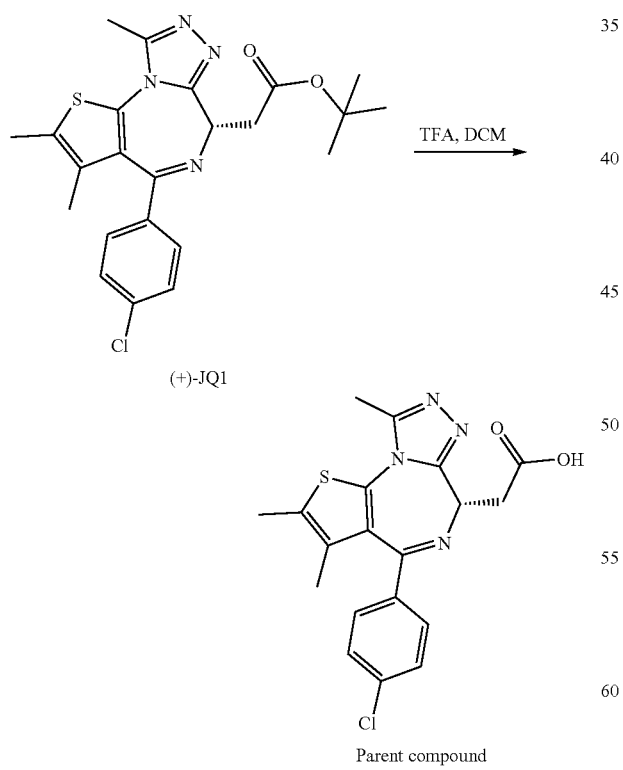

In a 500 ml reaction flask, a solution of tert-butyl(S)-2-(4-(4-chlorophenyl)-2,3,9-trimethyl-6H-thieno[3,2-f][1,2,4]triazolo[4,3-a][1,4]diazepine-6-yl)acetate ((+)-JQ1) (2.30 g, 5.00 mmol) dissolved in dichloromethane (100 ml) was provided. Then TFA (20 mL) was added to the solution and stirring continued for 4 h at room temperature, The mixture was evaporated under reduced pressure to afford the title compound (6S)-4-(4-chlorophenyl)-2,3,9-trimethyl-6H-thieno[3,2-f][1,2,4]thiazolo[4,3-a][1,4]diazepine-6-acetic acid (2.00 g), the product was used to the next step without purification.

Preparation Example 2: Preparation of (S)-2-(4-(4-chlorophenyl)-2,3,9-trimethyl-6H-thieno[3,2f][1,2,4]triazolo[4,3-a][1,4]diaza-6-yl)-N-(piperazin-1-yl)acetamide (Compound (M-1))

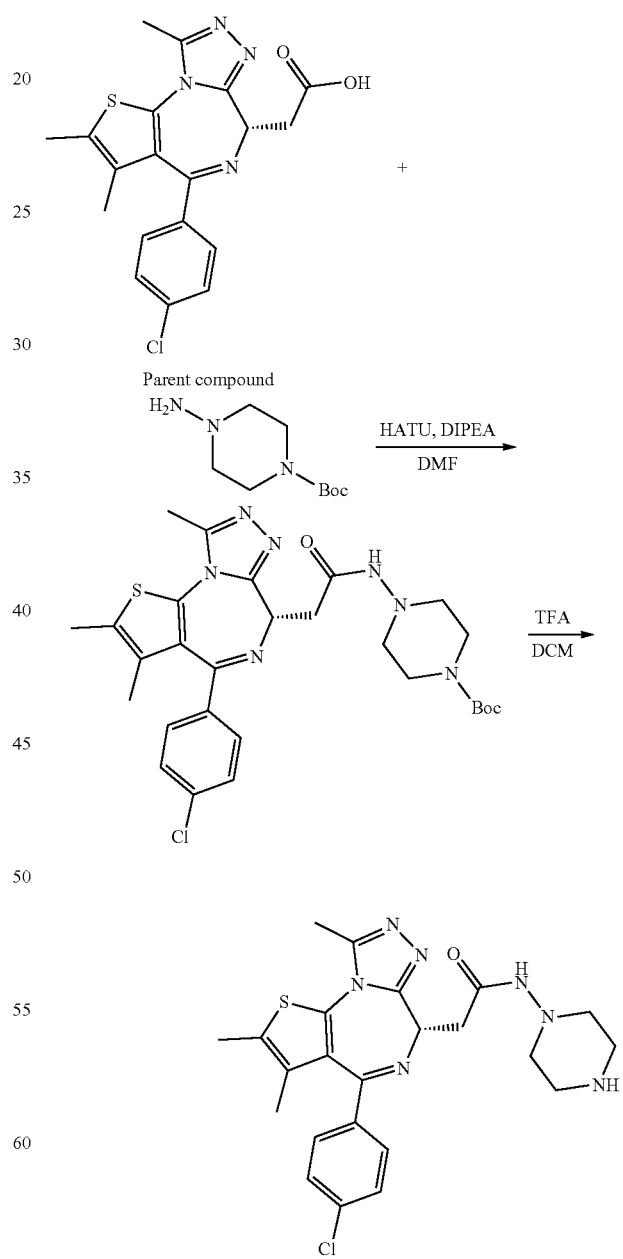

Step 1: Preparation of tert-butyl (s)-4-(2-(4-(4-(4-chlorophenyl)-2,3,9-trimethyl-6H-thieno[3,2-f][1,2,4]triazolo[4,3-a][1,4]diaza-6-yl)acetamido)piperazine-1-carboxylate In a 100 ml reaction flask, a solution of the parent compound (1) (0.40 g, 1 mmol) dissolved in DMF (20.0 ml) was provided. Then DIPEA (522 µl, 3 mmol), HATU (86.0 mg, 3 mmol) and tert-butyl 4-aminopiperazine-1-carboxylate (0.20 g, 1 mmol) were added to the solution, the mixture was stirred for 2 h at room temperature. After the reaction was completed, ethyl acetate and water were added, the organic layers were separated and evaporated under reduced pressure to afford the crude product tert-butyl (s)-4-(2-(4-(4-(4-chlorophenyl)-2,3,9-trimethyl-6H-thieno[3,2-f][1,2,4]triazolo[4,3-a][1,4]diaza-6-yl)acetamido)piperazine-1-carboxylate. The product is directly subjected to the next step without purification.

Step 2: Preparation of (S)-2-(4-(4-chlorophenyl)-2,3,9-trimethyl-6H-thieno[3,2-f][1,2,4]triazolo[4,3-a][1,4]diaza-6-yl)-N-(piperazin-1-yl)acetamide In a 100 ml reaction flask, Tert-butyl (s)-4-(2-(4-(4-(4-chlorophenyl)-2,3,9-trimethyl-6H-thieno[3,2-f][1,2,4]triazolo[4,3-a][1,4]diaza-6-yl) acetamido)piperazine-1-carboxylate (0.50 g, 0.86 mmol) was dissolved in DCM (100 ml), and TFA (5 ml) was added to the solution. The mixture was stirred for 4 h at room temperature, and then evaporated under reduced pressure to afford 0.40 g of (S)-2-(4-(4-chlorophenyl)-2,3,9-trimethyl-6H-thieno[3,2-f][1,2,4]triazolo[4,3-a][1,4]diaza-6-yl)-N-(piperazin-1-yl)acetamide (compound (M-1)), the product was used to the next step without purification.

Preparation Example 3: Preparation of (S)-1-(4-aminopiperazin-1-yl)-2-(4-(4-chlorophenyl)-2,3,9-trimethyl-6H-thieno[3,2-f][1,2,4]triazole[4,3-a][1,4]diaza-6-yl)ethanone (Compound (M-2))

(S)-1-(4-aminopiperazine-1-yl)-2-(4-(4-chlorophenyl)-2,3,9-trimethyl-6H-thieno[3,2-f][1,2,4]triazole[4,3-a][1,4]diaza-6-yl)ethanone (compound (M-2), 0.40 g) was prepared in a similar to that in Example 2, except that 4-amino piperazine-1-tert-butyl carbamate was replaced with piperazine-1-tert-butyl carboxylate.

Preparation Example 4: Preparation of (S)-2-(4-(4-chlorophenyl)-2,3,9-trimethyl-6H-thiophene[3,2-f][1,2,4]triazole[4,3-a][1,4]diazapine-6-yl)acethydrazine (Compound (M-3))

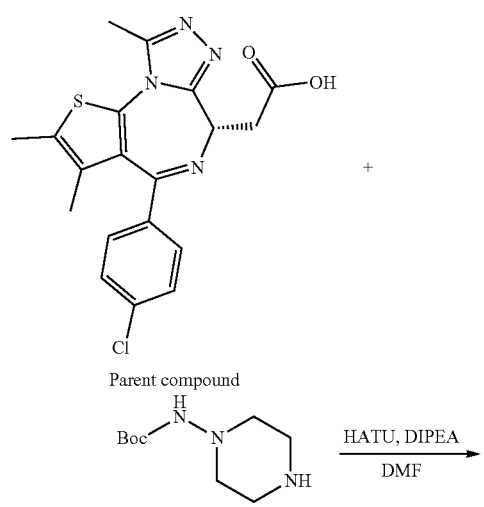

-continued

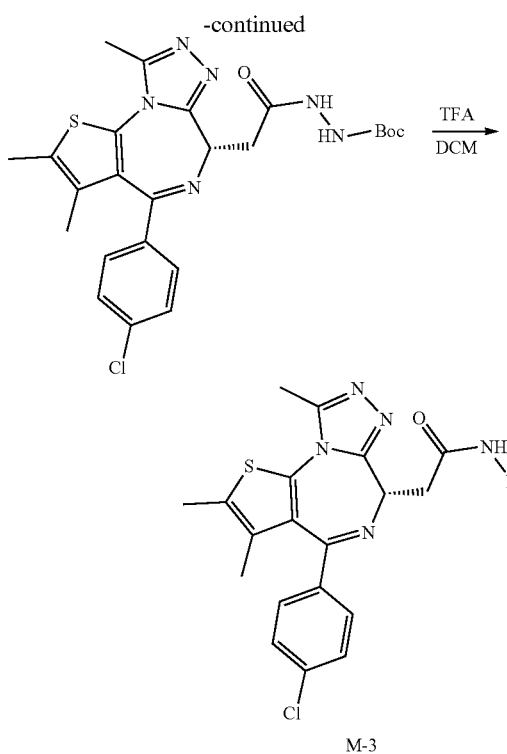

M-3

(S)-2-(4-(4-chlorophenyl)-2,3,9-trimethyl-6H-thiophene[3,2-f][1,2,4]triazole[4,3-a][1,4]diazapine-6-yl)acetylhydrazine (compound (M-3), 0.35 g) was prepared in a similar to that in Example 3, except that tert-butyl 4-aminopiperazine-1-carbamate was replaced by tert-butyl carbazate.

Preparation Example 5: Preparation of 4-(2-(2,6-dioxapiperidin-3-yl)-1-oxoisoindolin-4-yl)amino)-4-oxobutanoic Acid (Compound (C-1))

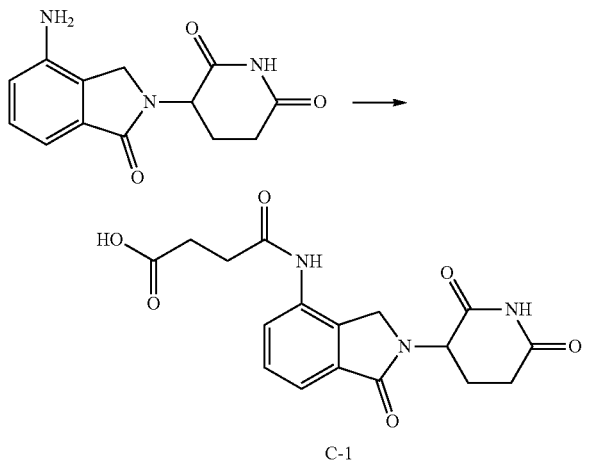

C-1

In a 250 ml reaction flask, a solution of Lenalidomide (1.28 g, 4.9 mmol) and succinic anhydride (0.64 g, 6.4 mmol) were dissolved in toluene (100 ml). The mixture was heated to 125° C. and reacted for 5.0 h, and then cooled to room temperature. The mixture was vacuum filtered and dried to obtain 1.70 g of 4-(2-(2,6-dioxapiperidin-3-yl)-1-oxoisoindolin-4-yl)amino)-4-oxobutyric acid (compound (C-1)).

Preparation Example 6: Preparation of 5-(2-(2,6-dioxapiperidin-3-yl)-1-oxoisoindolin-4-yl)amino)-5-oxopentanoic Acid (Compound (C-2))

5-(2-(2,6-dioxapiperidin-3-yl)-1-oxoisoindolin-4-yl)amino)-5-oxopentanoic acid (compound (C-2), 1.65 g) was prepared in a similar to that in Example 5, except that succinic anhydride was replaced with glutaric anhydride.

Preparation Example 7: Preparation of 6-(2-(2,6-dioxapiperidin-3-yl)-1-oxoisoindolin-4-yl)amino)-6-oxohexanoic Acid (Compound (C-3))

6-(2-(2,6-dioxapiperidin-3-yl)-1-oxoisoindolin-4-yl)amino)-6-oxohexanoic acid (compound of formula (C-3), 1.21 g) was prepared in a similar to that in Example 5, except that succinic anhydride was replaced with adipic anhydride.

Preparation Example 8: Preparation of 2-((2-(2,6-dioxapiperazin-3-yl)-1,3-dioxaindol-4-yl)amino) acetic Acid (Compound (C-4))

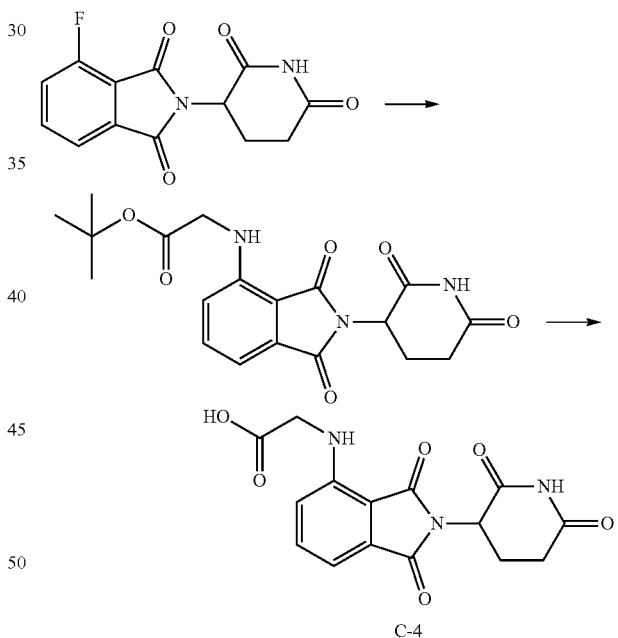

C-4

Step 1: preparation of tert-butyl 2-((2-(2,6-dioxopiperidin-3-yl)-1,3-dioxoindolin-4-yl)amino) acetate In a 100 ml reaction flask, a solution of 2-(2,6-dioxopiperidin-3-yl)-4-fluoroisoindoline-1,3-dione (0.30 g, 1.1 mmol) was dissolved in DMF, DIPEA (3841, 2.2 mmol), tert-butyl glycine (0.17 g, 1.3 mmol) was added to the solution, and then the mixture was heated to 90° C. for 2 h. The mixture was cooled to room temperature, water and ethyl acetate were added to the mixture. The organic phase was separated and evaporated under reduced pressure to afford tert-butyl 2-((2-(2,6-dioxopiperidin-3-yl)-1,3-dioxoisoindolin-4-yl)amino) acetate (0.38 g). The product was used to the next step without purification.

Step 2: preparation of 2-((2-(2,6-dioxopiperidin-3-yl)-1,3-dioxoisoindolin-4-yl)amino)acetic acid (compound (C-4))

In a 100 ml reaction flask, a solution of Tert-butyl 2-((2-(2,6-dioxopiperidin-3-yl)-1,3-dioxoisoindolin-4-yl) amino) acetate (0.38 g, 0.98 mmol) was dissolved in DCM (100 ml), and TFA (5 ml) was added to the solution. The mixture was stirring for 4 h at room temperature, and then evaporated under reduced pressure to afford of 2-((2-(2,6-dioxopiperidin-3-yl)-1,3-dioxoisoindolin-4-yl)amino)acetic acid (compound (C-4), 0.30 g). The product was used to the next step without purification.

Preparation Example 9: Preparation of 3-((2-(2,6-dioxapiperazin-3-yl)-1,3-dioxaindol-4-yl)amino) propionic Acid (Compound (C-5))

3-((2-(2,6-dioxopiperidin-3-yl)-1,3-dioxoisoindolin-4-yl) amino)propionic acid (compound (C-5), 0.42 g) was prepared in a similar to that in Example 8, except that tert-butyl glycine was replaced with tert-butyl alanine. The product was used to the next step without purification.

Preparation Example 10: Preparation of 4-((2-(2,6-dioxapiperazin-3-yl)-1,3-dioxaindol-4-yl)amino) butanoic Acid (Compound (C-6))

4-((2-(2,6-dioxopiperidin-3-yl)-1,3-dioxoisoindolin-4-yl) amino)butyric acid (compound of formula (C-6), 0.25 g) was prepared in a similar to that in Example 8, except that tert-butyl glycine was replaced with tert-butyl butyrate, The product was used to the next step without purification.

Preparation Example 11: Preparation of 5-((2-(2,6-dioxapiperazin-3-yl)-1,3-dioxaindol-4-yl)amino) pentanoic Acid (Compound (C-7))

5-((2-(2,6-dioxopiperidin-3-yl)-1,3-dioxoisoindolin-4-yl) amino)pentanoic acid (compound (C-7), 0.12 g) was prepared in a similar to that in Example 8, except that tert-butyl glycine was replaced with tert-butyl pentanoate. The product was used to the next step without purification.

Preparation Example 12: Preparation of 3-(2-(2-((2-(2,6-dioxopiperidin-3-yl)-1,3-dioxoisoindolin-4-yl) amino)ethoxy)ethoxy)propionic Acid (Compound (C-8))

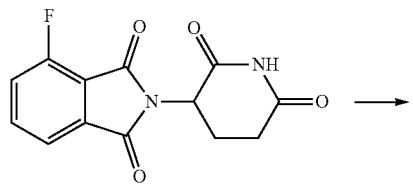

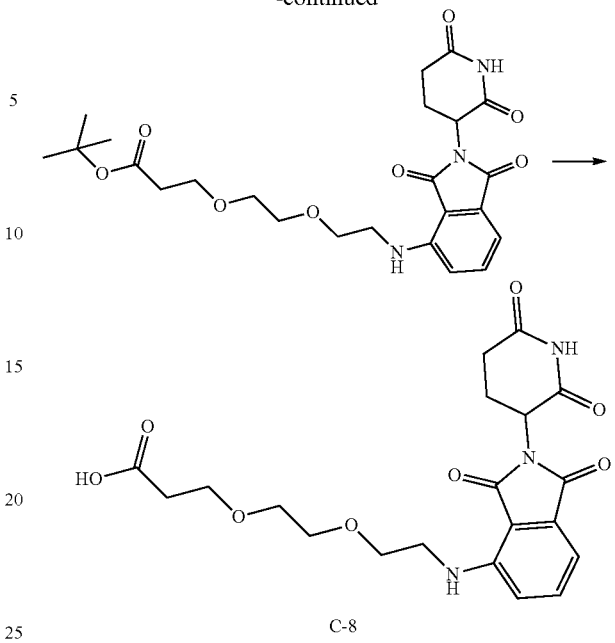

3-(2-(2-((2-(2,6-dioxopiperidin-3-yl)-1,3-dioxoisoindolin-4-yl)amino)ethoxy)ethoxy)propionic acid (compound (C-8), 0.30 g) was prepared in a similar to that in Example 8, except that tert-butyl glycine was replaced with tert-butyl 3-[2-(2-aminoethoxy)ethoxy]propionate.

Preparation Example 13: Preparation of 3-(2-(2-(2-(2-(2,6-dioxopiperidin-3-yl)-1,3-dioxoisoindolin-4-yl)amino)ethoxy)ethoxy)ethoxypropionic acid (compound of formula (C-9))

3-(2-(2-(2-(2-(2,6-dioxopiperidin-3-yl)-1,3-dioxisoindolin-4-yl)amino)ethoxy)ethoxy)ethoxypropionic acid (compound (C-9), 0.37 g) was prepared in a similar to that in Example 12, except that tert-butyl 3-[2-(2-aminoethoxy) ethoxy]propionate was replaced with tert-butyl 3-[2-[2-(2-aminoethoxy)ethoxy]ethoxy]propionate.

Preparation Example 14: Preparation of 1-((2-(2,6-dioxapiperazin-3-yl)-1,3-dioxaindol-4-yl)amino)-3, 6,9,12-tetraoxapentadecane-15-Acid (Compound (C-10))

1-((2-(2,6-dioxapiperazin-3-yl)-1,3-dioxa indol-4-yl) amino)-3,6,9,12-tetraoxapentadecane-15-acid (compound of formula (C-10), 0.26 g) was prepared in a similar to that in Example 12, except that tert-butyl 3-[2-(2-aminoethoxy) ethoxy]propionate was replaced with 2-[2-[2-[2-(2-tert-butoxy carbonylethoxy)ethoxy]ethoxy]ethoxy]ethylamine.

Preparation Example 15: Preparation of 2-((2-(2,6-dioxopiperidin-3-yl)-1-oxoisoindol-4-yl)amino)acetic Acid (Compound (C-11))

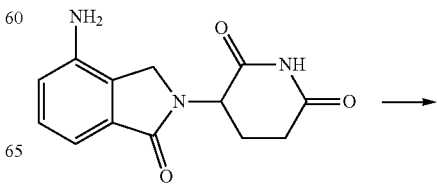

-continued

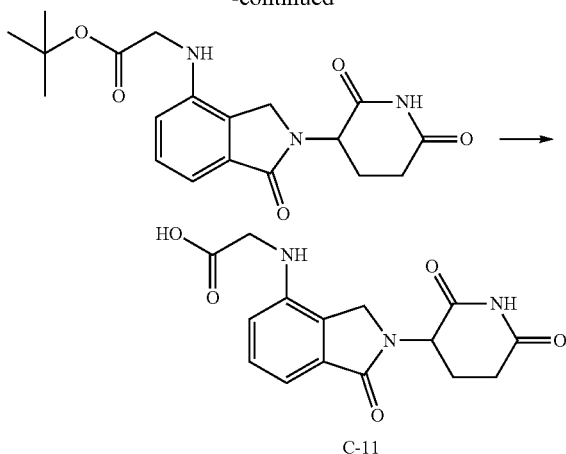

C-11

Step 1: Preparation of tert-butyl 2-((2-(2,6-dioxopiperidin-3-yl)-1-oxoisoindol-4-yl)amino) acetate A solution of Lenalidomide (259 mg, 1.0 mmol) dissolved in N,N-dimethylformamide (20 ml) was provided, and tert-butyl bromoacetate (234 mg, 1.2 mmol), and potassium carbonate (276 mg, 2.0 mmol), potassium iodide (8 mg, 0.05 mmol) were added to the solution. The mixture was stirred at 80° C. After the reaction was completed, ethyl acetate and water were added, and the organic phase was washed with water for twice. The organic phase was separated, and purified by silica gel chromatography to obtain tert-butyl 2-((2-(2,6-dioxopiperidine-3-yl)-1-oxoisoindol-4-yl)amino) acetate (150 mg).

Step 2: Preparation of 2-((2-(2,6-dioxopiperidin-3-yl)-1-oxoisoindol-4-yl)amino)acetic Acid (Compound (C-11))

A solution of Tert-butyl 2-((2-(2,6-dioxopiperidin-3-yl)-1-oxoisoindol-4-yl)amino) acetate (0.15 g, 0.40 mmol) dissolved in DCM (20 ml) was provided, and trifluoroacetic acid (7 ml) was added to the solution. The mixture was stirred at room temperature. After the reaction was completed, the mixture was distilled under reduced pressure to obtain 2-((2-(2,6-dioxopiperidin-3-yl)-1-oxoisoindol-4-yl)amino)acetic acid (compound (C-11), 0.10 g, oil). The product was used to the next step without purification.

Preparation Example 16: Preparation of 3-((2-(2,6-dioxopiperidin-3-yl)-1-oxoisoindol-4-yl)amino)propionic Acid (Compound (C-12))

3-((2-(2,6-dioxopiperidin-3-yl)-1-oxoisoindol-4-yl)amino)propionic acid (compound (C-12), 0.05 g, oil) was prepared in a similar to that in Example 15, except that tert-butyl bromoacetate was replaced with tert-butyl bromopropionate, the product is directly used to the next step without purification.

Preparation Example 17: Preparation of 4-((2-(2,6-dioxopiperidin-3-yl)-1-oxoisoindol-4-yl)amino)butanoic Acid (Compound (C-13))

4-((2-(2,6-dioxopiperidin-3-yl)-1-oxoisoindol-4-yl)amino)butyric acid (compound (C-13), 0.13 g, oil) was prepared in a similar to that in Example 15, except that tert-butyl bromoacetate was replaced with tert-butyl bromobutyrate. The product was directly used to the next step without purification.

Preparation Example 18: Preparation of 5-((2-(2,6-dioxopiperidin-3-yl)-1-oxoisoindol-4-yl)amino)pentanoic Acid (Compound (C-14))

5-((2-(2,6-dioxopiperidin-3-yl)-1-oxoisoindol-4-yl)amino)pentanoic acid (compound of formula (C-14), 0.13 g, oil) was prepared in a similar to that in Example 15, except that tert-butyl bromoacetate was replaced with tert-butyl bromovalerate. The product was directly used to the next step without purification.

Preparation Example 19: Preparation of 2-((2-(2,6-dioxopiperidin-3-yl)-1,3-dioxoisoindolin-4-yl)oxy) acetic Acid (compound (C-15))

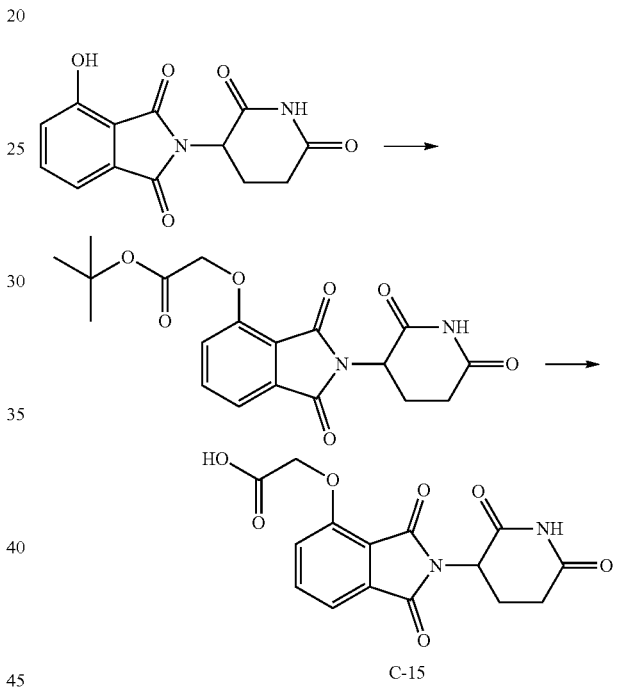

C-15

Step 1: Preparation of tert-butyl 2-((2-(2,6-dioxopiperidin-3-yl)-1,3-dioxoisoindolin-4-yl)oxy) acetate A solution of 2-(2,6-Dioxopiperidin-3-yl)-4-hydroxyisoindoline-1,3-dione (274 mg, 1.0 mmol) dissolved in N,N-dimethylformamide (20 ml) was provided, then tert-butyl bromoacetate (234 mg, 1.2 mmol), potassium carbonate (276 mg, 2.0 mmol) and potassium iodide (8 mg, 0.05 mmol) were added to the solution and stirred at 80° C. After the reaction was completed, ethyl acetate and water were added, and the organic phase was washed twice with water. The organic phase was separated, and purified by column chromatography to obtain 2-((2-(2,6-dioxopiperidin-3-yl)-1,3-dioxoisoindolin-4-yl)oxy) tert-butyl acetate (150 mg).

Step 2: Preparation of 2-((2-(2,6-dioxopiperidin-3-yl)-1,3-dioxoisoindolin-4-yl)oxy)acetic Acid (Compound of Formula (C-6))

A solution of Tert-butyl 2-((2-(2,6-dioxopiperidin-3-yl)-1,3-dioxoisoindolin-4-yl)oxy) acetate (0.15 g, 0.37 mmol)

dissolved in dichloromethane (20 ml) was provided, then TFA (7 ml) was added to the solution. The mixture was stirred at room temperature. After the reaction was completed, the mixture was distilled under reduced pressure to obtain 2-((2-(2,6-dioxopiperidine)-3-yl)-1,3-dioxoisoindolin-4-yl)oxy)acetic acid (compound of formula (C-15), 0.10 g, oil), the product was directly used to the next step without purification.

Example 1: Preparation of 4-(4-(2-((S)-4-(4-chlorophenyl)-2,3,9-trimethyl-6H-thieno[3,2-f][1,2,4]triazolo[4,3-a][1,4]diaza-6-yl)acetamido)piperazin-1-yl)-N-(2-(2,6-dioxpiperazin-3-yl)-1-oxoisoindolin-4-yl)-4-oxobutanamide In a 100 ml reaction flask, a solution of the compound of formula M-1 (53 mg, 0.11 mmol) dissolved in DMF (10.0 ml) was provided, and then HATU (40 μl, 0.23 mmol) and the compound C-1 (39 mg, 0.11 mmol) were added to the solution. The mixture was stirred for 2.0 h at room temperature. TLC showed that raw material was consumed. The reaction solution was poured into water (100.0 ml), extracted with DCM, dried over anhydrous sodium sulfate, evaporated under reduced pressure, and purified and separated by preparative liquid chromatography (dichloromethane:methanol=30:1) to afford 4-(4-(2-((S)-4-(4-chlorophenyl)-2,3,9-trimethyl-6H-thieno[3,2-f][1,2,4]triazolo[4,3-a][1,4]diaza-6-yl)acetamido)piperazin-1-yl)-N-(2-(2,6-dioxopiperazin-3-yl)-1-oxoisoindolin-4-yl)-4-oxobutanamide 30 mg, the yield was 33%.

Example 2-45: Preparation of the Compound of Example 2-45

The products were prepared in a similar to that in Example 1, except that the compound of formula M1 and the compound of formula C1 were replaced with corresponding M-1-M-3 and C-1-C-15 respectively, the detailed are shown below:

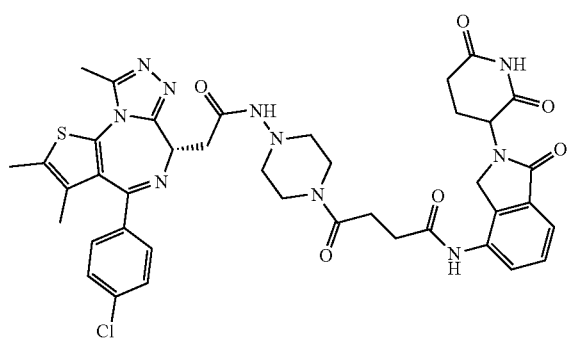 [SMILES: Cc1sc2c(c1C)C(c1ccc(Cl)cc1)=N[C@@H](CC(=O)NN1CCN(C(=O)CCC(=O)Nc3cccc4c3CN(C3CCC(=O)NC3=O)C4=O)CC1)c1nnc(C)n1-2]

| Example | Compound M | Compound C | Product Compound |
|---|---|---|---|
| 2 | M-1 | C-2 | |
| 3 | M-1 | C-3 | |

| Example | Compound M | Compound C | Product Compound |
|---|---|---|---|
| 4 | M-1 | C-4 | 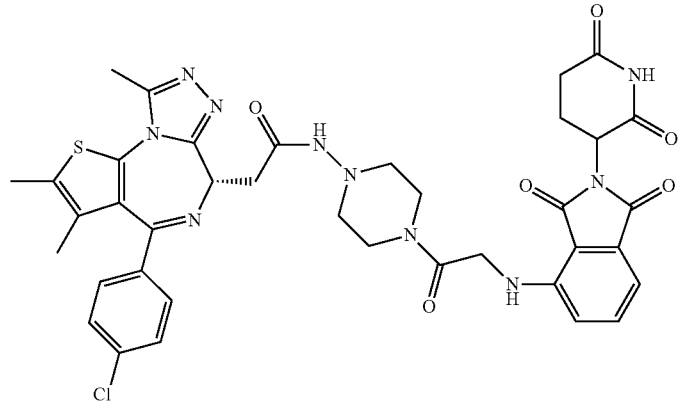 [SMILES: Cc1sc2c(c1C)C(c1ccc(Cl)cc1)=N[C@@H](CC(=O)NN1CCN(C(=O)CNc3cccc4c3C(=O)N(C3CCC(=O)NC3=O)C4=O)CC1)c1nnc(C)n1-2] |
| 5 | M-1 | C-5 | 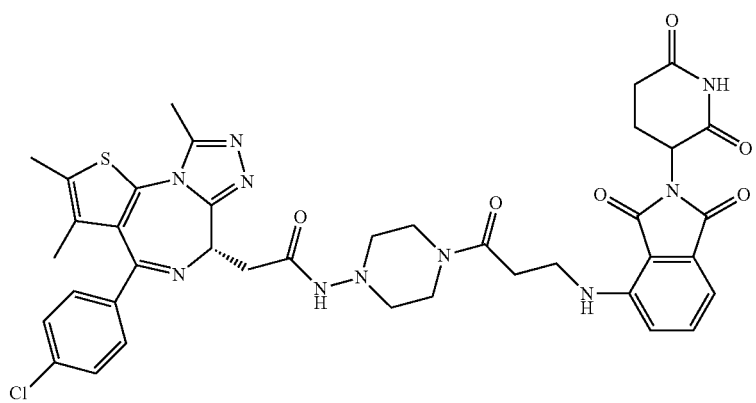 [SMILES: Cc1sc2c(c1C)C(c1ccc(Cl)cc1)=N[C@@H](CC(=O)NN1CCN(C(=O)CCNc3cccc4c3C(=O)N(C3CCC(=O)NC3=O)C4=O)CC1)c1nnc(C)n1-2] |
| 6 | M-1 | C-6 | 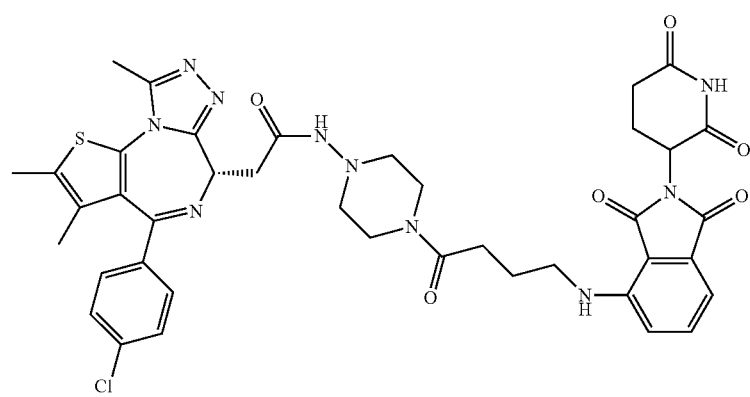 [SMILES: Cc1sc2c(c1C)C(c1ccc(Cl)cc1)=N[C@@H](CC(=O)NN1CCN(C(=O)CCCNc3cccc4c3C(=O)N(C3CCC(=O)NC3=O)C4=O)CC1)c1nnc(C)n1-2] |
| 7 | M-1 | C-7 | 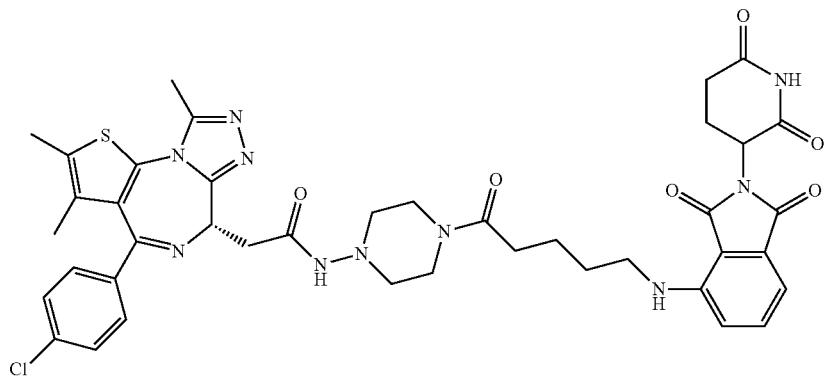 [SMILES: Cc1sc2c(c1C)C(c1ccc(Cl)cc1)=N[C@@H](CC(=O)NN1CCN(C(=O)CCCCNc3cccc4c3C(=O)N(C3CCC(=O)NC3=O)C4=O)CC1)c1nnc(C)n1-2] |

| Example | Compound M | Compound C | Product Compound |
|---|---|---|---|
| 8 | M-1 | C-8 | |
| 9 | M-1 | C-9 | MC-9 |
| 10 | M-1 | C-10 | |
| 11 | M-1 | C-11 | |

-continued
| Example | Compound M | Compound C | Product Compound |
|---|---|---|---|
| 12 | M-1 | C-12 | 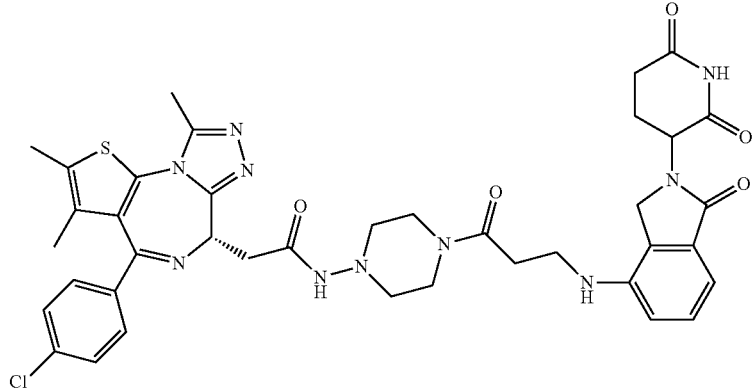 [SMILES: Cc1sc2c(c1C)C(c1ccc(Cl)cc1)=N[C@@H](CC(=O)NN1CCN(C(=O)CCNc3cccc4c3CN(C3CCC(=O)NC3=O)C4=O)CC1)c1nnc(C)n1-2] |
| 13 | M | C-13 | 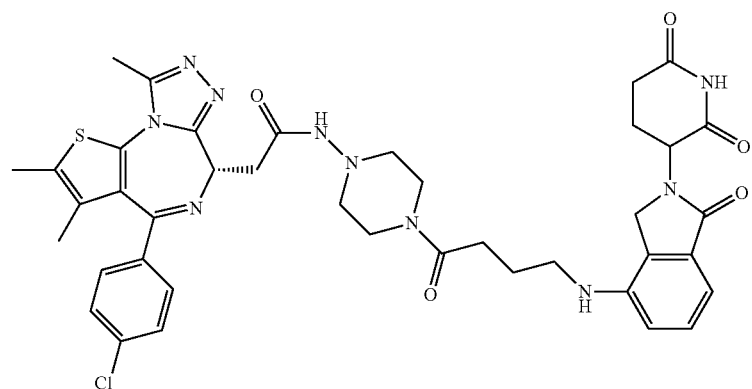 [SMILES: Cc1sc2c(c1C)C(c1ccc(Cl)cc1)=N[C@@H](CC(=O)NN1CCN(C(=O)CCCNc3cccc4c3CN(C3CCC(=O)NC3=O)C4=O)CC1)c1nnc(C)n1-2] |
| 14 | M-1 | C-14 | 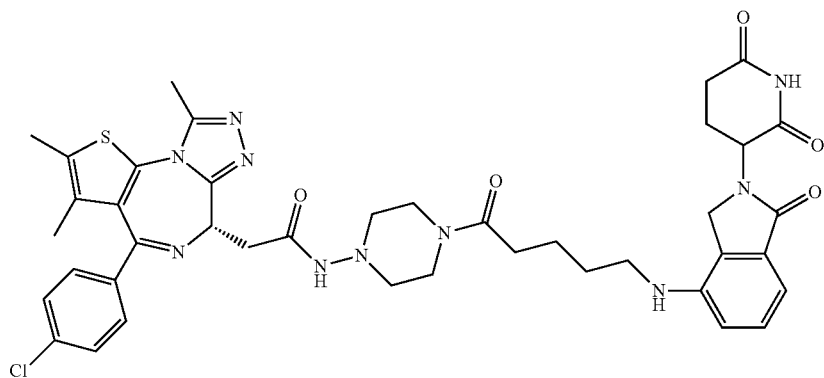 [SMILES: Cc1sc2c(c1C)C(c1ccc(Cl)cc1)=N[C@@H](CC(=O)NN1CCN(C(=O)CCCCNc3cccc4c3CN(C3CCC(=O)NC3=O)C4=O)CC1)c1nnc(C)n1-2] |
| 15 | M-1 | C-15 | 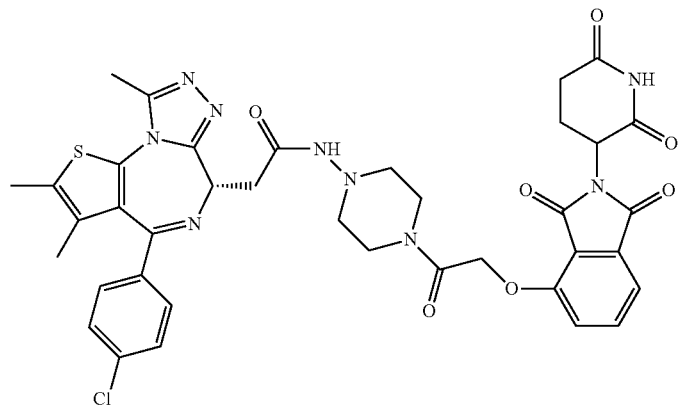 [SMILES: Cc1sc2c(c1C)C(c1ccc(Cl)cc1)=N[C@@H](CC(=O)NN1CCN(C(=O)COc3cccc4c3C(=O)N(C3CCC(=O)NC3=O)C4=O)CC1)c1nnc(C)n1-2] |

| Example | Compound M | Compound C | Product Compound |
|---|---|---|---|
| 16 | M-2 | C-1 | 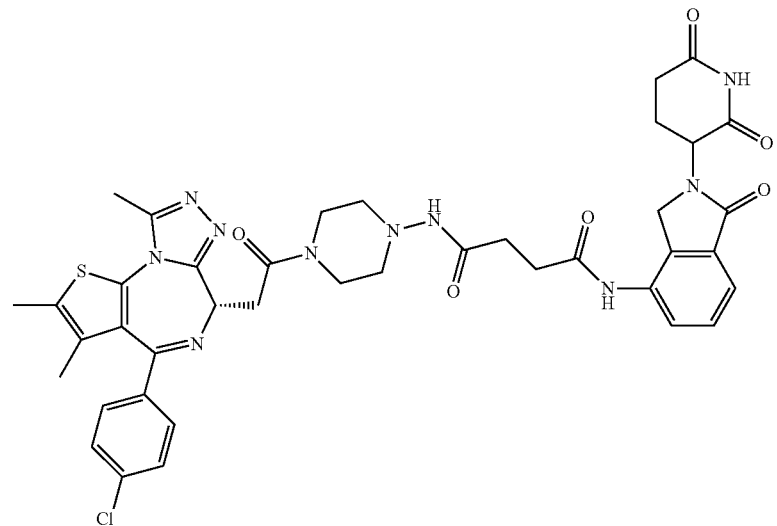 [SMILES: Cc1sc2c(c1C)C(c1ccc(Cl)cc1)=N[C@@H](CC(=O)N1CCN(NC(=O)CCC(=O)Nc3cccc4c3CN(C3CCC(=O)NC3=O)C4=O)CC1)c1nnc(C)n1-2] |
| 17 | M-2 | C-2 | 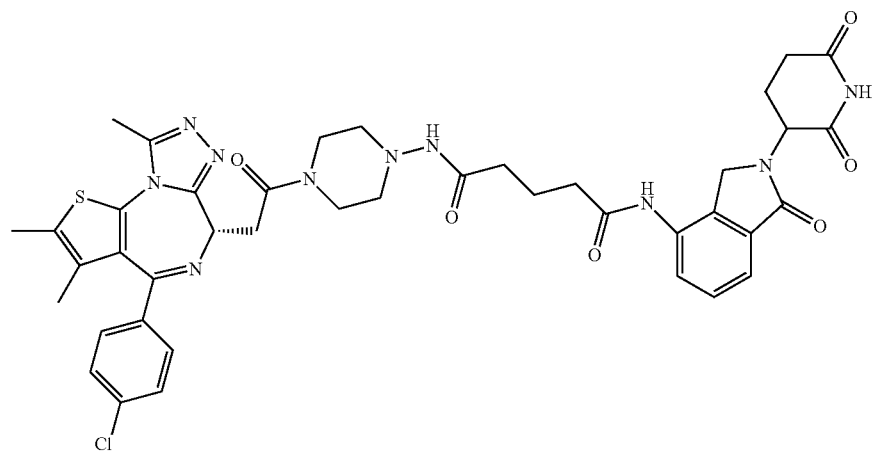 [SMILES: Cc1sc2c(c1C)C(c1ccc(Cl)cc1)=N[C@@H](CC(=O)N1CCN(NC(=O)CCCC(=O)Nc3cccc4c3CN(C3CCC(=O)NC3=O)C4=O)CC1)c1nnc(C)n1-2] |
| 18 | M-2 | C-3 | 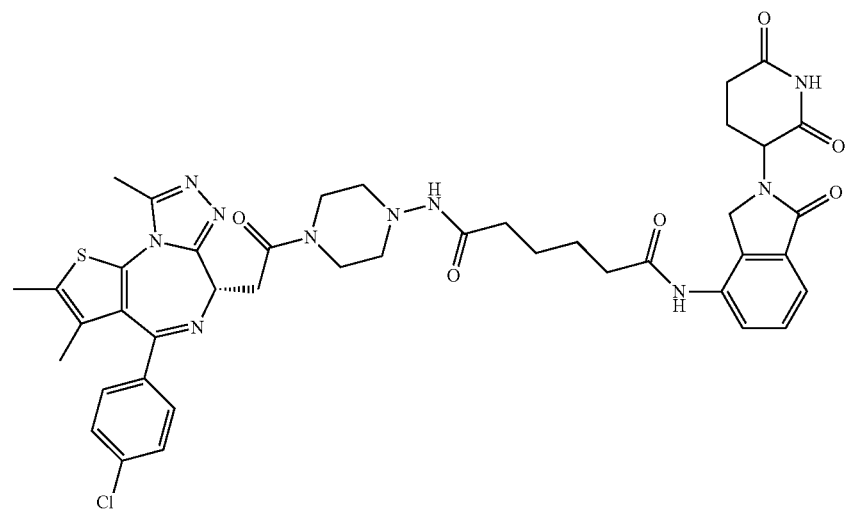 [SMILES: Cc1sc2c(c1C)C(c1ccc(Cl)cc1)=N[C@@H](CC(=O)N1CCN(NC(=O)CCCCC(=O)Nc3cccc4c3CN(C3CCC(=O)NC3=O)C4=O)CC1)c1nnc(C)n1-2] |

| Example | Compound M | Compound C | Product Compound |
|---|---|---|---|
| 19 | M-2 | C-4 | 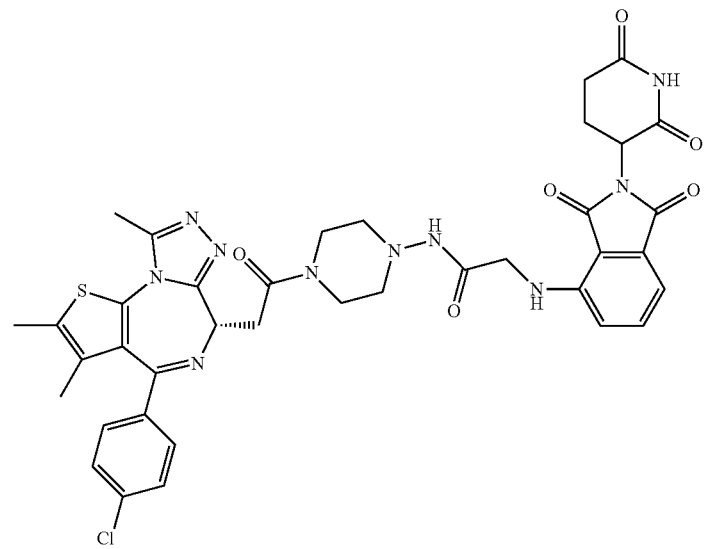 [SMILES: Cc1sc2c(c1C)C(c1ccc(Cl)cc1)=N[C@@H](CC(=O)N1CCN(NC(=O)CNc3cccc4c3C(=O)N(C3CCC(=O)NC3=O)C4=O)CC1)c1nnc(C)n1-2] |
| 20 | M-2 | C-5 | 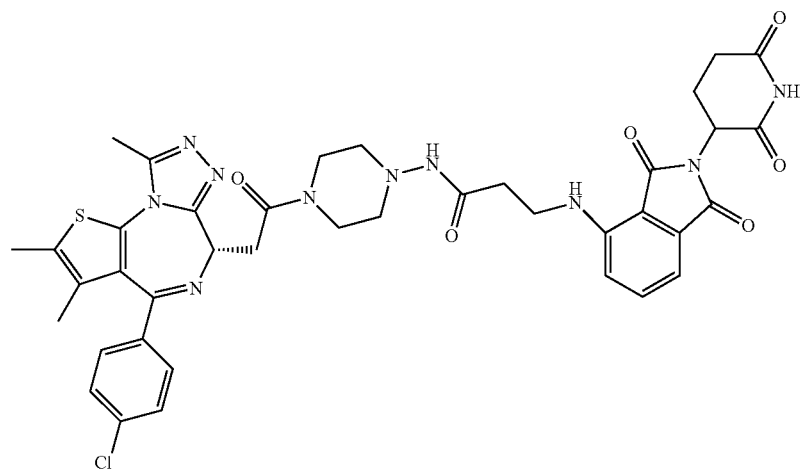 [SMILES: Cc1sc2c(c1C)C(c1ccc(Cl)cc1)=N[C@@H](CC(=O)N1CCN(NC(=O)CCNc3cccc4c3C(=O)N(C3CCC(=O)NC3=O)C4=O)CC1)c1nnc(C)n1-2] |
| 21 | M-2 | C-6 | 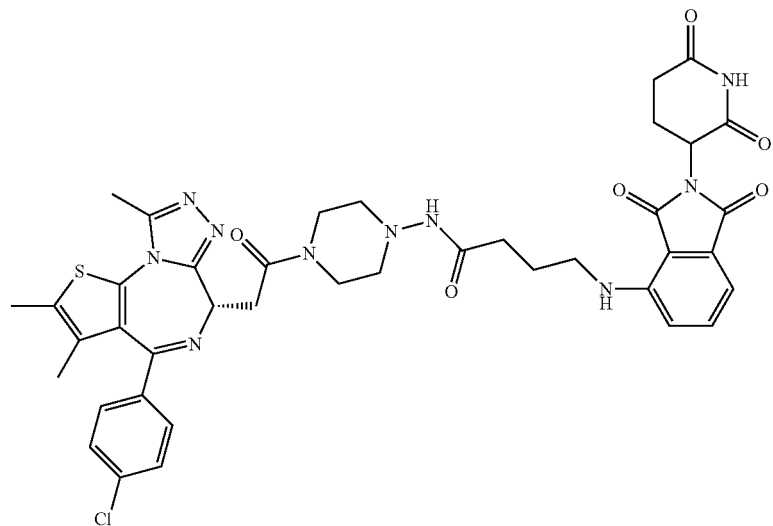 [SMILES: Cc1sc2c(c1C)C(c1ccc(Cl)cc1)=N[C@@H](CC(=O)N1CCN(NC(=O)CCCNc3cccc4c3C(=O)N(C3CCC(=O)NC3=O)C4=O)CC1)c1nnc(C)n1-2] |

| Example | Compound M | Compound C | Product Compound |
|---|---|---|---|
| 22 | M-2 | C-7 | 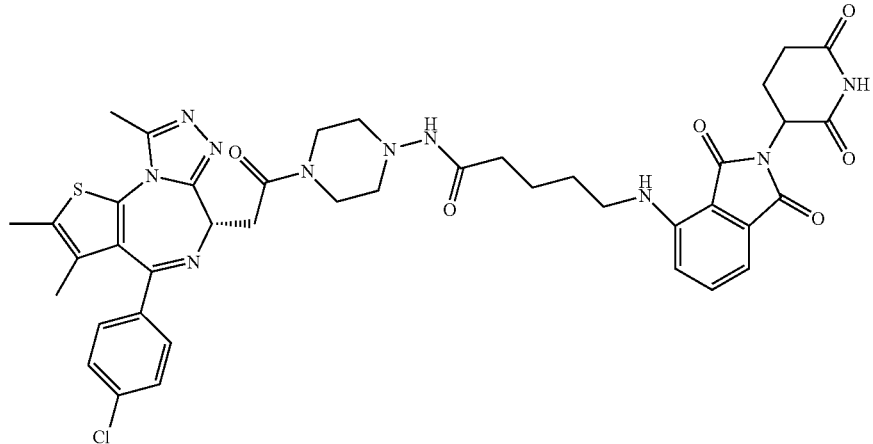 [SMILES: Cc1sc2c(c1C)C(c1ccc(Cl)cc1)=N[C@@H](CC(=O)N1CCN(NC(=O)CCCCNc3cccc4c3C(=O)N(C3CCC(=O)NC3=O)C4=O)CC1)c1nnc(C)n1-2] |
| 23 | M-2 | C-8 | 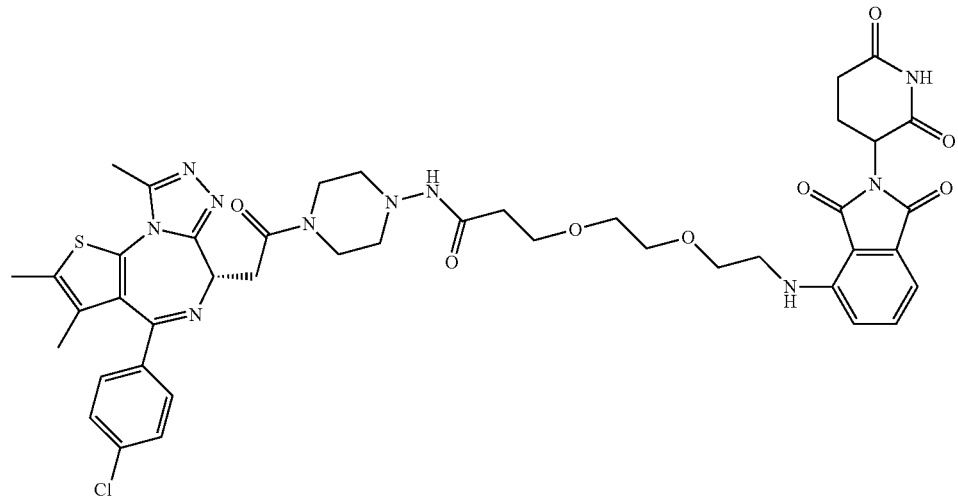 [SMILES: Cc1sc2c(c1C)C(c1ccc(Cl)cc1)=N[C@@H](CC(=O)N1CCN(NC(=O)CCOCCOCCNc3cccc4c3C(=O)N(C3CCC(=O)NC3=O)C4=O)CC1)c1nnc(C)n1-2] |
| 24 | M-2 | C-9 | 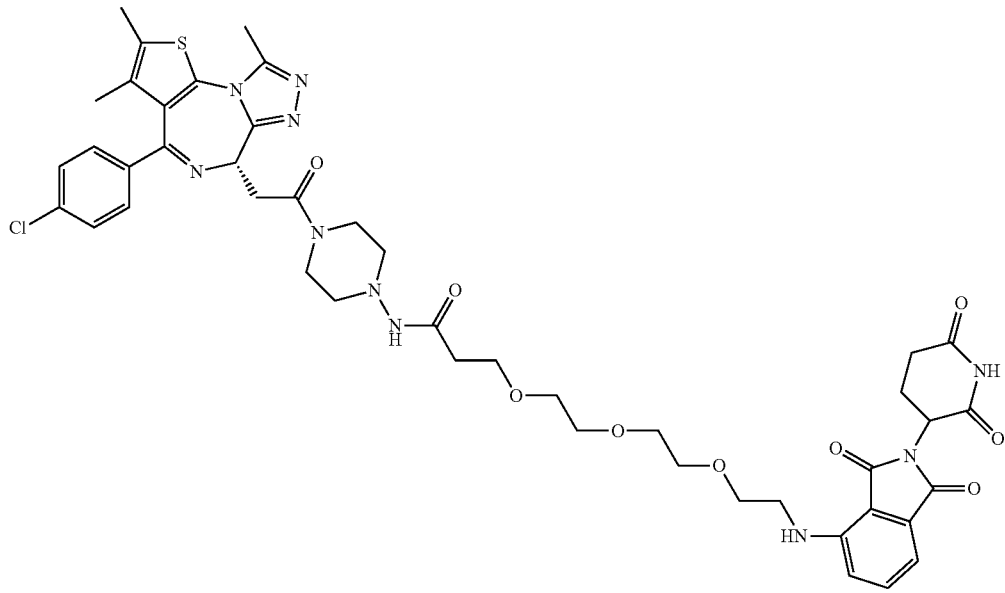 [SMILES: Cc1sc2c(c1C)C(c1ccc(Cl)cc1)=N[C@@H](CC(=O)N1CCN(NC(=O)CCOCCOCCOCCNc3cccc4c3C(=O)N(C3CCC(=O)NC3=O)C4=O)CC1)c1nnc(C)n1-2] |

-continued
| Example | Compound M | Compound C | Product Compound |
|---|---|---|---|
| 25 | M-2 | C-10 | 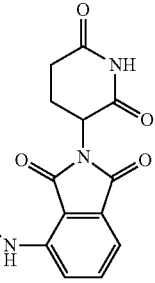 |
| 26 | M-2 | C-11 | 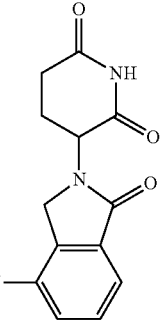 |
| 27 | M-2 | C-12 | 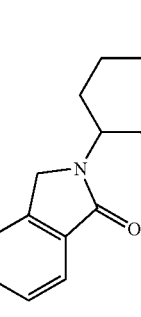 |

| Example | Compound M | Compound C | Product Compound |
|---|---|---|---|
| 28 | M-2 | C-13 | 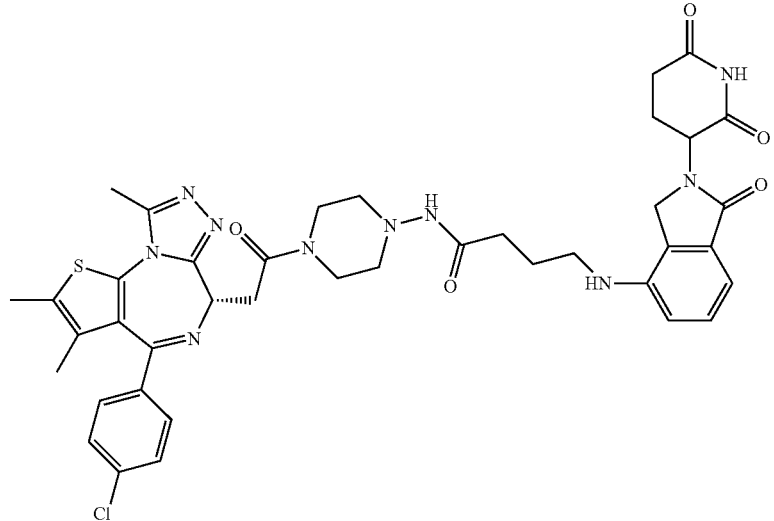 [SMILES: Cc1sc2c(c1C)C(c1ccc(Cl)cc1)=N[C@@H](CC(=O)N1CCN(NC(=O)CCCNc3cccc4c3CN(C3CCC(=O)NC3=O)C4=O)CC1)c1nnc(C)n1-2] |
| 29 | M-2 | C-14 | 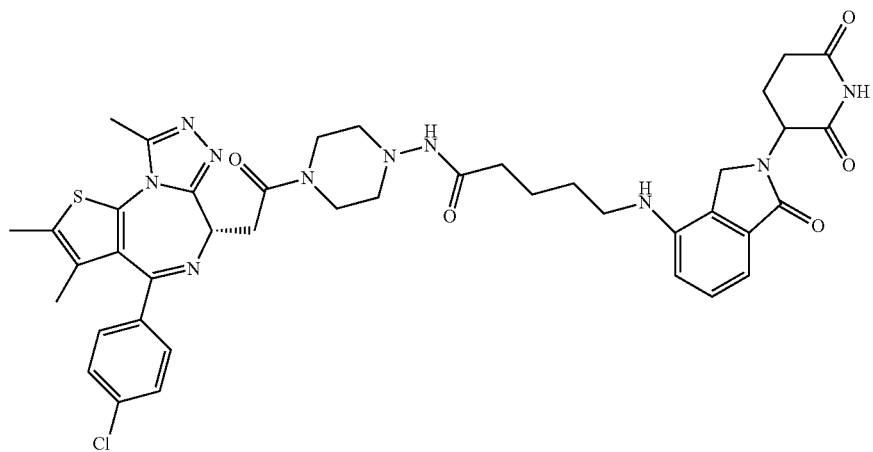 [SMILES: Cc1sc2c(c1C)C(c1ccc(Cl)cc1)=N[C@@H](CC(=O)N1CCN(NC(=O)CCCCNc3cccc4c3CN(C3CCC(=O)NC3=O)C4=O)CC1)c1nnc(C)n1-2] |
| 30 | M-2 | C-15 | 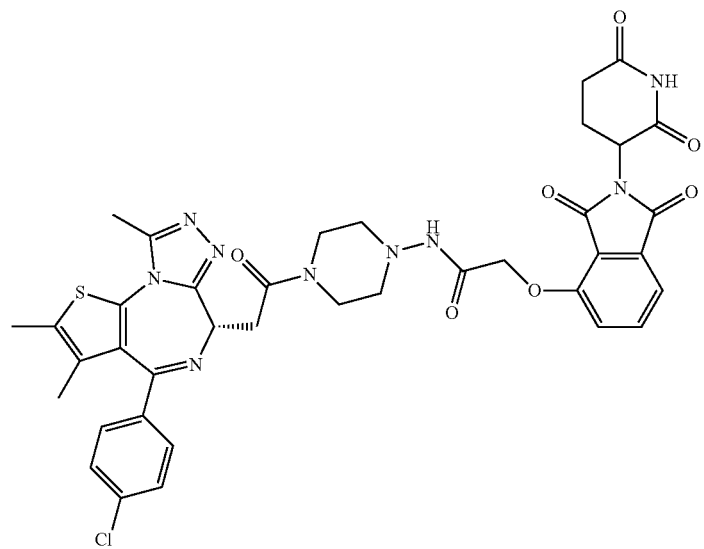 [SMILES: Cc1sc2c(c1C)C(c1ccc(Cl)cc1)=N[C@@H](CC(=O)N1CCN(NC(=O)COc3cccc4c3C(=O)N(C3CCC(=O)NC3=O)C4=O)CC1)c1nnc(C)n1-2] |

| Example | Compound M | Compound C | Product Compound |
|---|---|---|---|
| 31 | M-3 | C-1 | 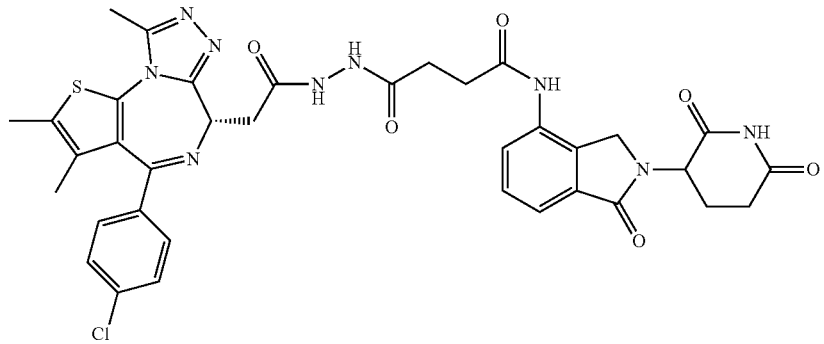 [SMILES: Cc1sc2c(c1C)C(c1ccc(Cl)cc1)=N[C@@H](CC(=O)NNC(=O)CCC(=O)Nc1cccc3c1CN(C1CCC(=O)NC1=O)C3=O)c1nnc(C)n1-2] |
| 32 | M-3 | C-2 | 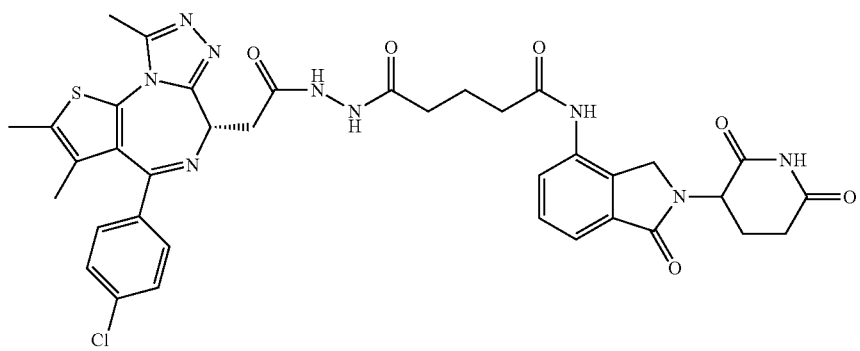 [SMILES: Cc1sc2c(c1C)C(c1ccc(Cl)cc1)=N[C@@H](CC(=O)NNC(=O)CCCC(=O)Nc1cccc3c1CN(C1CCC(=O)NC1=O)C3=O)c1nnc(C)n1-2] |
| 33 | M-3 | C-3 | 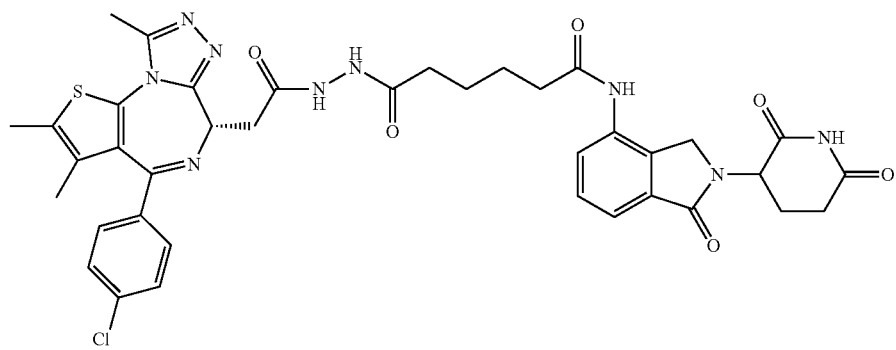 [SMILES: Cc1sc2c(c1C)C(c1ccc(Cl)cc1)=N[C@@H](CC(=O)NNC(=O)CCCCC(=O)Nc1cccc3c1CN(C1CCC(=O)NC1=O)C3=O)c1nnc(C)n1-2] |
| 34 | M-3 | C-4 | 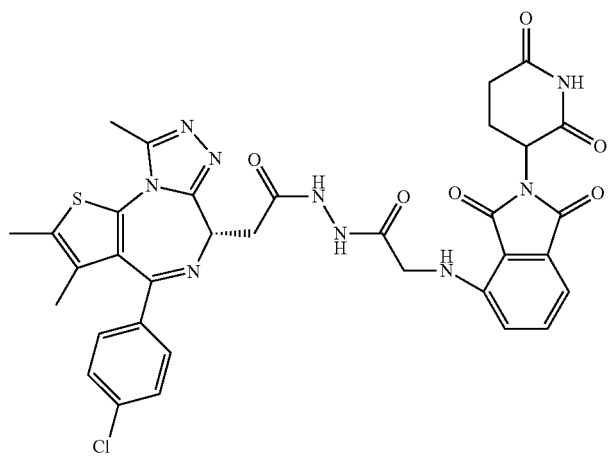 [SMILES: Cc1sc2c(c1C)C(c1ccc(Cl)cc1)=N[C@@H](CC(=O)NNC(=O)CNc1cccc3c1C(=O)N(C1CCC(=O)NC1=O)C3=O)c1nnc(C)n1-2] |

| Example | Compound M | Compound C | Product Compound |
|---|---|---|---|
| 35 | M-3 | C-5 | 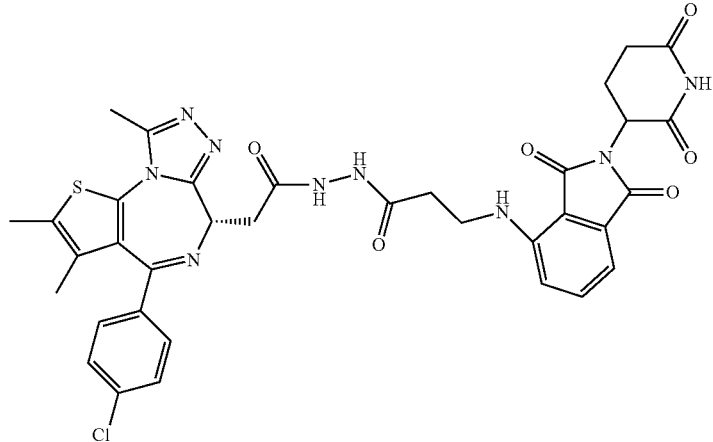 [SMILES: Cc1sc2c(c1C)C(c1ccc(Cl)cc1)=N[C@@H](CC(=O)NNC(=O)CCNc1cccc3c1C(=O)N(C1CCC(=O)NC1=O)C3=O)c1nnc(C)n1-2] |
| 36 | M-3 | C-6 | 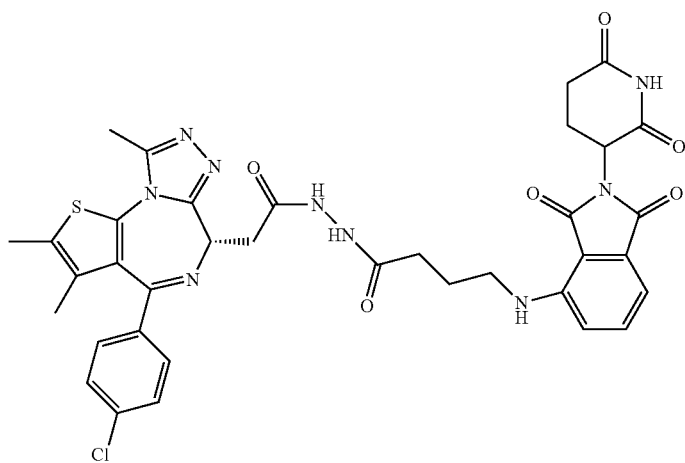 [SMILES: Cc1sc2c(c1C)C(c1ccc(Cl)cc1)=N[C@@H](CC(=O)NNC(=O)CCCNc1cccc3c1C(=O)N(C1CCC(=O)NC1=O)C3=O)c1nnc(C)n1-2] |
| 37 | M-3 | C-7 | 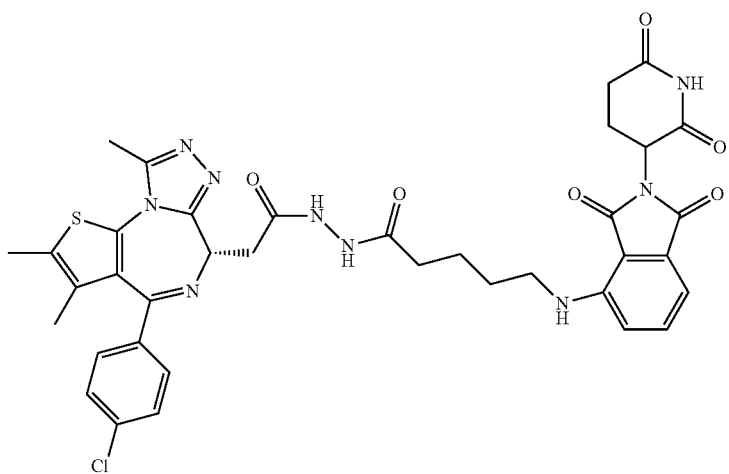 [SMILES: Cc1sc2c(c1C)C(c1ccc(Cl)cc1)=N[C@@H](CC(=O)NNC(=O)CCCCNc1cccc3c1C(=O)N(C1CCC(=O)NC1=O)C3=O)c1nnc(C)n1-2] |

-continued
| Example | Compound M | Compound C | Product Compound |
|---|---|---|---|
| 38 | M-3 | C-8 | 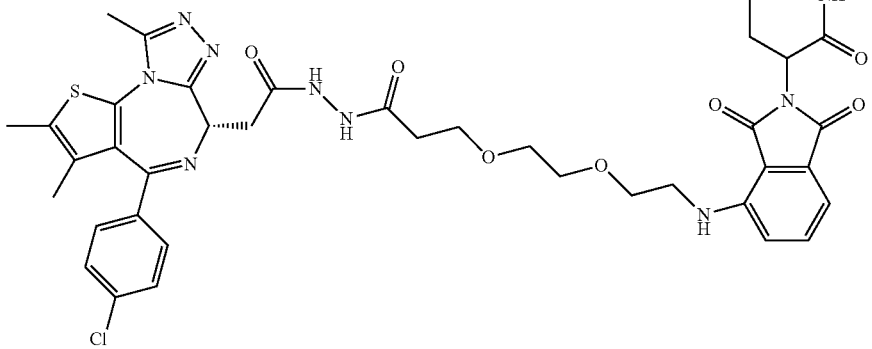 |
| 39 | M-3 | C-9 | 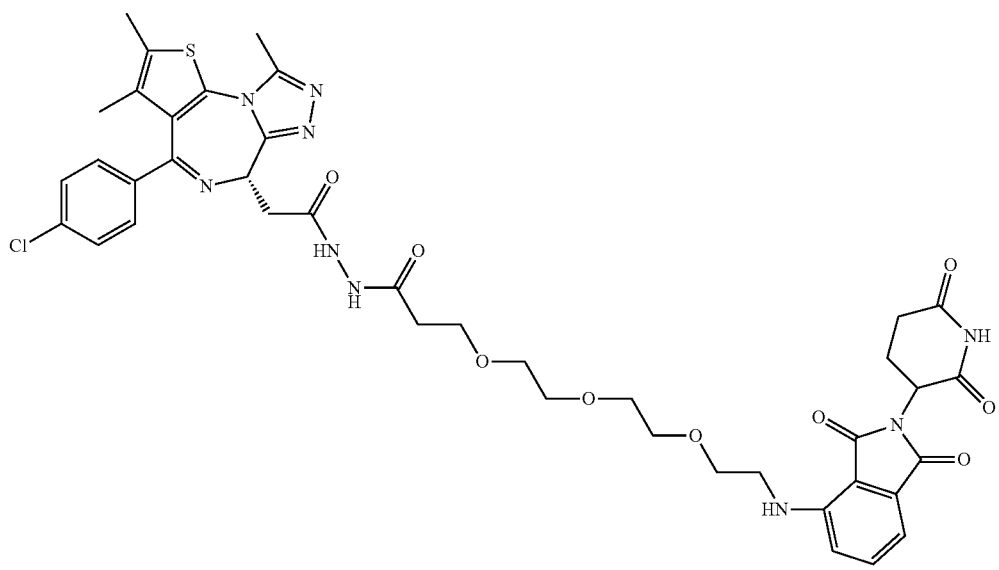 [SMILES: Cc1sc2c(c1C)C(c1ccc(Cl)cc1)=N[C@@H](CC(=O)NNC(=O)CCOCCOCCOCCNc1cccc3c1C(=O)N(C1CCC(=O)NC1=O)C3=O)c1nnc(C)n1-2] |
| 40 | M-3 | C-10 | 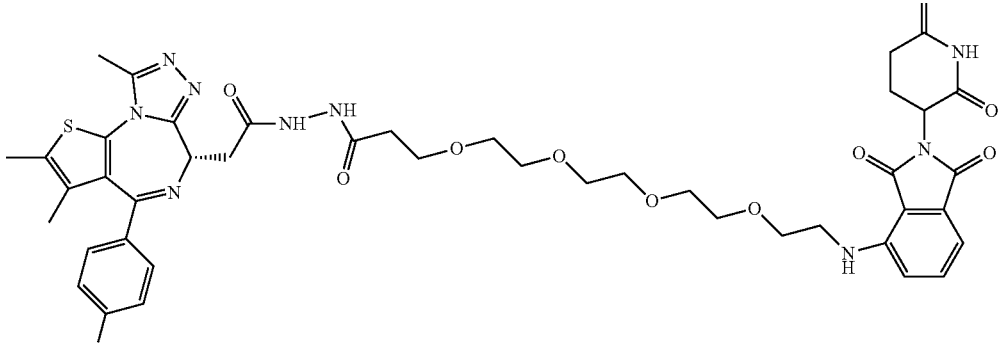 |

-continued
| Example | Compound M | Compound C | Product Compound |
|---|---|---|---|
| 41 | M-3 | C-11 | 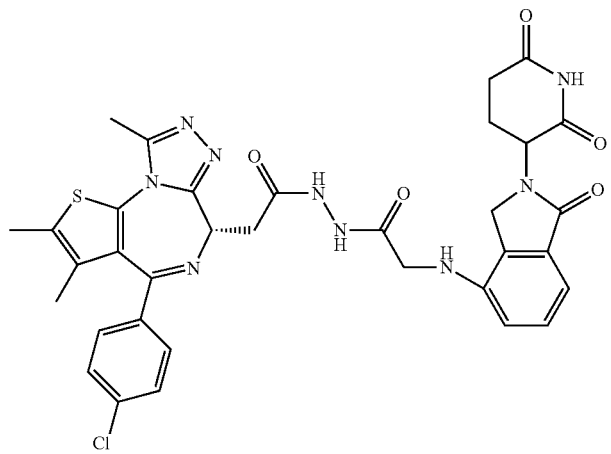 [SMILES: Cc1sc2c(c1C)C(c1ccc(Cl)cc1)=N[C@@H](CC(=O)NNC(=O)CNc1cccc3c1CN(C1CCC(=O)NC1=O)C3=O)c1nnc(C)n1-2] |
| 42 | M-3 | C-12 | 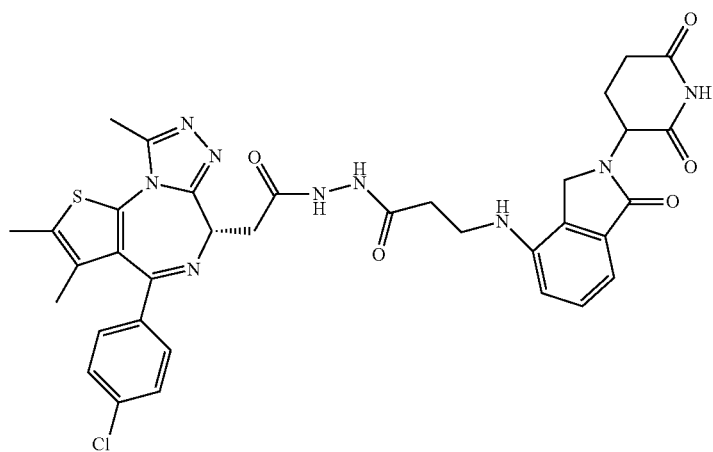 [SMILES: Cc1sc2c(c1C)C(c1ccc(Cl)cc1)=N[C@@H](CC(=O)NNC(=O)CCNc1cccc3c1CN(C1CCC(=O)NC1=O)C3=O)c1nnc(C)n1-2] |
| 43 | M-3 | C-13 | 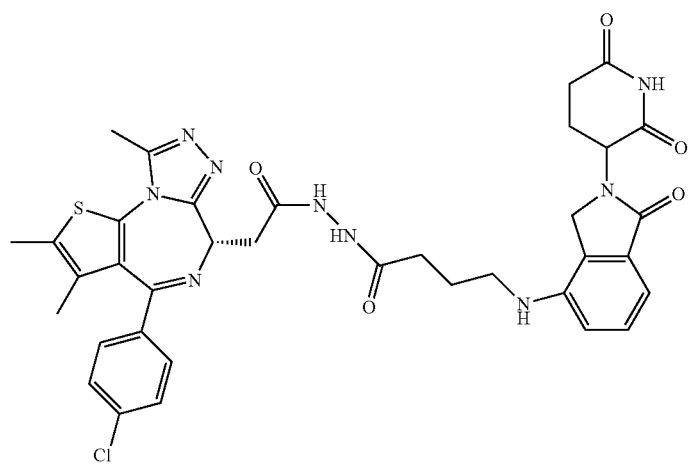 [SMILES: Cc1sc2c(c1C)C(c1ccc(Cl)cc1)=N[C@@H](CC(=O)NNC(=O)CCCNc1cccc3c1CN(C1CCC(=O)NC1=O)C3=O)c1nnc(C)n1-2] |

| Example | Compound M | Compound C | Product Compound |
|---|---|---|---|
| 44 | M-3 | C-14 | 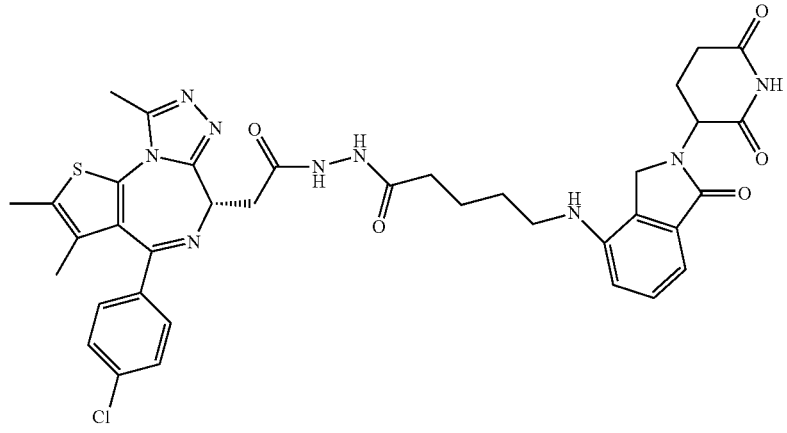 [SMILES: Cc1sc2c(c1C)C(c1ccc(Cl)cc1)=N[C@@H](CC(=O)NNC(=O)CCCCNc1cccc3c1CN(C1CCC(=O)NC1=O)C3=O)c1nnc(C)n1-2] |
| 45 | M-3 | C-15 | 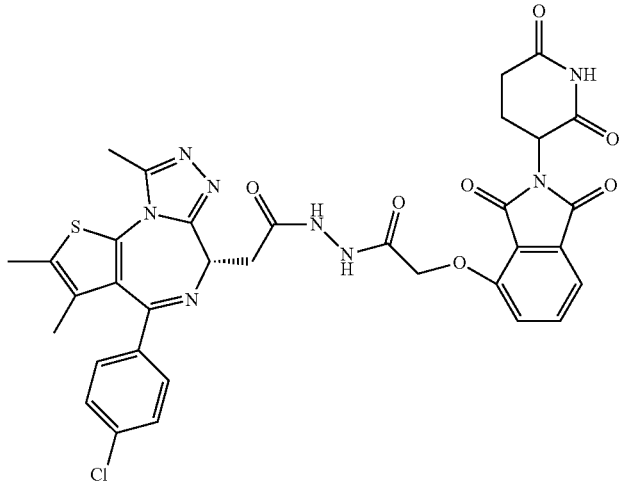 [SMILES: Cc1sc2c(c1C)C(c1ccc(Cl)cc1)=N[C@@H](CC(=O)NNC(=O)COc1cccc3c1C(=O)N(C1CCC(=O)NC1=O)C3=O)c1nnc(C)n1-2] |

Physical characterization of specific compounds were as follows:

| Example | $^{1}$H NMR(600 MHz, DMSO)δ | MS[M + H]$^{+}$ |
|---|---|---|
| 1 | $^{1}$H NMR (600 MHz, DMSO-d$_{6}$) δ: 1.044-1.067 (m, 1H), 1.625-1.633 (m, 3H), 2.043-2.052 (m, 1H), 2.301-2.384(m, 1H), 2.412(s, 3H), 2.596-2.749 (m, 10H), 2.823-2.923(m, 1H), 3.085-3.150(m, 1H) 3.170-3.230 (m, 1H), 3.431-3.451(m, 1H), 3.529-3.556 (m, 3H), 4.321-4.388(m, 3H), 4.417-4.548 (m, 1H), 5.137-5.167 (m, 1H), 7.417-7.454(m, 2H), 7.485-7.512 (m, 4H), , 7.837-7.848(m, 1H), 9.367 (s, 1H) 9.858(s, 1H), 11.028(s, 1H) | 825.3 |
| 4 | $^{1}$H NMR (600 MHz, CDCl$_{3}$) δ: 0.903-0.941 (m, 1H), 1.266-1.277 (m, 2H), 1.323-1.359 (m, 1H), 1.444-1.573 (m, 1H), 1.613-1.923 (m, 3H), 2.127(s, 1H), 2.451-2.521(s, 3H) 2.687-2.728 (m, 3H), 2.807-2.921 (m, 3H), 3.089-3.108 (m, 1H), 3.457-3.864(m, 4H), 4.074-4.235 (m, 2H), 4.651-4.680 (m, 1H), 4.937 (s, 1H), 6.811-6.825 (m, 1H), , 7.027-7.217(m, 2H), 7.344-7.500 (m, 5H) 8.002-8.164(m, 1H), 8.780-9.197(m, 1H) | 797.3 |
| 8 | $^{1}$H NMR (600 MHz, CDCl$_{3}$) δ: 0.892-0.923 (m, 1H), 1.244-1.286 (m, 2H), 1.352-1.386 (m, 1H), 1.444-1.573 (m, 1H), 1.656-1.989 (m, 3H), 2.125(s, 1H), 2.441-2.521(s, 3H) 2.677-2.725 (m, 3H), 2.827-2.931 (m, 3H), 3.089-3.108 (m, 1H), 3.457-3.864(m, 4H), 4.074-4.235 (m, 2H), 4.281-4.305 (m, 2H), 4.651-4.680 (m, 1H), 4.937 (s, 1H), 6.861-6.885 (m, 1H), , 7.037-7.214(m, 2H), 7.344-7.500 (m, 5H) 8.012-8.163(m, 1H), 8.770-9.195(m, 1H) | 899.3 |

-continued

| Example | ¹H NMR(600 MHz, DMSO)δ | MS[M + H]⁺ |
|---|---|---|
| 9 | ¹H NMR (600 MHz, CDCl₃) δ: 0.812-0.911 (m, 1H), 1.218-1.237 (m, 2H), 1.325-1.355 (m, 3H), 1.414-1.493 (m, 1H), 1.642-1.943 (m, 3H), 2.337(s, 1H), 2.451-2.521(s, 3H), 2.637-2.768 (m, 3H), 2.827-2.926 (m, 3H), 3.089-3.138 (m, 1H), 3.257-3.364(m, 4H), 4.251-4.568 (m, 1H), 4.737 (s, 1H), 6.795-6.845 (m, 1H), , 7.127-7.257(m, 2H), 7.374-7.615 (m, 5H) 8.015-8.189(m, 1H), 8.475-9.082(m, 1H) | 943.5 |
| 11 | ¹H NMR (600 MHz, CDCl₃) δ: 0.803-0.941 (m, 1H), 1.216-1.247 (m, 2H), 1.323-1.359 (m, 3H), 1.434-1.503 (m, 1H), 1.643-1.933 (m, 3H), 2.327(s, 1H), 2.451-2.521(s, 3H) 2.637-2.768 (m, 3H), 2.827-2.926 (m, 3H), 3.089-3.138 (m, 1H), 3.257-3.364(m, 4H), 3.894-4.235 (m, 2H), 4.251-4.568 (m, 1H), 4.737 (s, 1H), 6.791-6.835 (m, 1H), , 7.127-7.257(m, 2H), 7.384-7.610 (m, 5H) 8.012-8.174(m, 1H), 8.480-9.097(m, 1H) | 783.2 |
| 15 | ¹H NMR (600 MHz, CDCl₃) δ: 0.952-0.974 (m, 1H), 1.236-1.257 (m, 2H), 1.303-1.338 (m, 1H), 1.432-1.536 (m, 1H), 1.643-1.923 (m, 3H), 2.031(s, 1H), 2.341-2.601(s, 3H) 2.687-2.752 (m, 3H), 2.832-2.921 (m, 3H), 3.189-3.258 (m, 1H), 3.457-3.654 (m, 4H), 4.174-4.229 (m, 2H), 4.551-4.647 (m, 1H), 4.877 (s, 1H), 6.741-6.830 (m, 1H), 7.127-7.257(m, 2H), 7.484-7.596 (m, 4H) 8.102-8.234(m, 1H), 8.880-9.267(m, 1H) | 798.1 |
| 16 | ¹H NMR (600 MHz, DMSO-d₆) δ: 1.154-1.237 (m, 1H), 1.575-1.603 (m, 3H), 2.043-2.152 (m, 1H), 2.321-2.414(m, 1H), 2.475(s, 3H), 2.536-2.751 (m, 10H), 2.825-2.931(m, 1H), 3.089-3.169(m, 1H) 3.241-3.301 (m, 1H), 3.446-3.473(m, 1H), 3.560-3.654 (m, 3H), 4.171-4.296(m, 3H), 4.452-4.618 (m, 1H), 5.037-5.567 (m, 1H), 7.467-7.514(m, 2H), 7.585-7.691 (m, 4H), 7.837-7.948(m, 1H), 9.351 (s, 1H) 9.889(s, 1H), 11.008(s, 1H) | 825.2 |
| 19 | ¹H NMR (600 MHz, CDCl₃) δ: 0.913-0.953 (m, 1H), 1.281-1.291 (m, 2H), 1.343-1.369 (m, 1H), 1.464-1.532 (m, 1H), 1.599-1.923 (m, 3H), 2.139(s, 1H), 2.449-2.521(s, 3H) 2.675-2.726 (m, 3H), 2.843-2.964 (m, 3H), 3.034-3.112 (m, 1H), 3.507-3.844(m, 4H), 4.024-4.221 (m, 2H), 4.632-4.655 (m, 1H), 4.926 (s, 1H), 6.821-6.845 (m, 1H), , 7.104-7.209(m, 2H), 7.384-7.560 (m, 5H) 8.022-8.164(m, 1H), 8.810-9.167(m, 1H) | 797.1 |
| 23 | ¹H NMR (600 MHz, CDCl₃) δ: 0.947-0.968 (m, 1H), 1.281-1.291 (m, 2H), 1.383-1.412 (m, 1H), 1.454-1.539 (m, 1H), 1.588-1.963 (m, 3H), 2.126(s, 1H), 2.449-2.521(s, 3H) 2.675-2.726 (m, 3H), 2.843-2.964 (m, 3H), 3.034-3.112 (m, 1H), 3.221-3.335 (m, 2H), 3.507-3.844(m, 4H), 4.024-4.221 (m, 2H), 4.228-4.442 (m, 2H), 4.542-4.642 (m, 1H), 4.937 (s, 1H), 6.837-6.853 (m, 1H), , 7.254-7.279(m, 2H), 7.354-7.460 (m, 5H) 8.032-8.154(m, 1H), 8.826-9.187(m, 1H) | 899.5 |
| 24 | ¹H NMR (600 MHz, CDCl₃) δ: 0.945-0.997 (m, 1H), 1.301-1.331 (m, 2H), 1.353-1.369 (m, 1H), 1.464-1.532 (m, 1H), 1.599-1.923 (m, 3H), 2.329(s, 1H), 2.449-2.521(s, 3H) 2.675-2.726 (m, 3H), 2.843-2.964 (m, 3H), 3.034-3.112 (m, 1H), 3.221-3.335 (m, 2H), 3.507-3.844(m, 4H), 4.024-4.221 (m, 2H), 4.229-4.310 (m, 2H), 4.328-4.452 (m, 2H), 4.510-4.610 (m, 2H), 4.632-4.655 (m, 1H), 4.886 (s, 1H), 6.821-6.845 (m, 1H), , 7.204-7.269(m, 2H), 7.394-7.540 (m, 5H) 8.055-8.184(m, 1H), 8.890-9.163(m, 1H) | 943.3 |
| 26 | ¹H NMR (600 MHz, CDCl₃) δ: 0.899-0.921 (m, 1H), 1.248-1.297 (m, 2H), 1.330-1.401 (m, 1H), 1.431-1.521 (m, 3H), 1.579-1.873 (m, 3H), 2.089(s, 1H), 2.348-2.497(s, 3H) 2.535-2.716 (m, 3H), 2.823-2.924 (m, 3H), 3.024-3.212 (m, 1H), 3.497-3.794(m, 4H), 3.978-4.191 (m, 2H), 4.602-4.648 (m, 1H), 4.906 (s, 1H), 6.811-6.865 (m, 1H), 7.104-7.213(m, 2H), 7.352-7.592 (m, 5H) 8.021-8.163(m, 1H), 8.812-9.155(m, 1H) | 783.3 |
| 30 | ¹H NMR (600 MHz, CDCl₃) δ: 0.940-0.977 (m, 1H), 1.201-1.242 (m, 2H), 1.313-1.333 (m, 1H), 1.421-1.537 (m, 1H), 1.655-1.903 (m, 3H), 2.021(s, 1H), 2.348-2.597(s, 3H) 2.656-2.749 (m, 3H), 2.803-2.926 (m, 3H), 3.181-3.268 (m, 1H), 3.447-3.616 (m, 4H), 4.141-4.222 (m, 2H), 4.534-4.638 (m, 1H), 4.871 (s, 1H), 6.741-6.841 (m, 1H), 7.127-7.327(m, 2H), 7.484-7.656 (m, 4H) 8.112-8.244(m, 1H), 8.892-9.272(m, 1H) | 798.2 |
| 31 | ¹H NMR (600 MHz, DMSO-d₆) δ: 1.609-1.628 (m, 3H), 1.988-2.007 (m, 1H), 2.333-2.407(m, 4H), 2.501-2.598 (m, 5H), 2.647-2.671 (m, 2H), 2.275-2.291 (m, 1H), 3..154-3.172 (m, 2H), 3.323-3.354 (m, 1H), 4.326-4.394 (m, 2H), 4.501-4.521 (m, 1H), 5.119-5.149 (m, 1H), 7.423-7.452 (m, 6H), 7.830-7.880 (m, 1H), 9.898-9.943(d, 2H), 10.143(s, 1H), 10.995-11.007(m, 1H). | 756.5 |
| 34 | ¹H NMR (600 MHz, CDCl₃) δ: 0.853-0.907 (m, 1H), 1.264 (s, 3H), 1.668-1.685 (m, 3H), 2.088 (m, 2H), 2.414 (s, 3H), 2.549-2.569 (m, 2H), 2.682-2.691 (m, 2H), 2.728-2.741(m, 2H), 3.443-3.506 (m, 3H), 3.572-3.584 (m, 1H), 3.644-3.685 (m, 3H), 3.733-3.789 (m, 3H), 4.612-4.622 (m, 1H), 4.934-4.978 (m, 1H), 6.569 (s, 1H), 6.893-6.907 (m, 1H), 7.098-7.110 (m, 1H), 7.315-7.347 (m, 2H), 7.435-7.503(m, 3H), 9.041-9.241(m, 2H), 9.450-9.650(m, 1H). | 830.5 |

Biological Example 1: Effects of Compounds on the Proliferation of RS4; 11 and MM.1S Cells Cell lines for test: acute leukemia cell line RS4; 11 and multiple myeloma cell line MM.1S Test method: MTT (thiazole blue) method, which was also called MTT colorimetry assay, was a method used to detect cell survival and growth. The principle of the assay was that the succinate dehydrogenase in mitochondria of living cells could reduce the exogenous MTT to waterinsoluble blue-purple crystal formazan and deposit it in the cells, while dead cells have no such function. Dimethyl sulfoxide (DMSO) could dissolve formazan in cells, and its light absorption value was measured at 550 nm wavelength by enzyme-linked immunoassay, which could indirectly reflect the number of living cells. Within a certain range of cell numbers, the amount of MTT crystal formation is proportional to the number of cells. This method has been widely used in the activity detection of some biologically active factors, large-scale anti-tumor drug screening, cytotoxicity test, and tumor radiosensitivity determination.

Experiment Procedure:
Dosage Design

The concentration gradient of the compound was as follows: 0-25.6 pM-128 pM-640 pM-3.2 nm-16 nM-80 nM-400 nM-2 μM-10 μM; (n=3)

Detection and Calculation 72 h after drug administration, 20 μl per well of MTT working solution (5 mg/ml) was added, and incubated at 37° C. for 4 h, centrifuged in plate centrifuge at 1000 rpm/min for 5 min. 180 μl of medium was aspirated and 150 μl DMSO was added in RS4; 11 groups; 200 μl of medium was aspirated and 150 μl DMSO was added in MM.1S group; the mixture was shaken and mixed on microwell shaker, and the bottom of the plate was wiped, and the optical density (OD) was measured at 550 nm by microplate reader. The $IC_{50}$ of the half inhibitory concentration was calculated by LOGIT method.

Experimental Results:

| Medicine | $IC_{50}$ (nM) | |
| --- | --- | --- |
|  | RS4; 11 | MM.1S |
| JQ1 | C | C |
| dBET1 | C | C |
| ARV-825 | B | B |
| The compound in Example 1 | A | A |
| The compound in Example 4 | A | A |
| The compound in Example 5 | A | A |
| The compound in Example 8 | B | A |
| The compound in Example 9 | A | B |
| The compound in Example 11 | A | A |
| The compound in Example 12 | A | A |
| The compound in Example 15 | A | A |
| The compound in Example 16 | A | A |
| The compound in Example 19 | A | A |
| The compound in Example 20 | A | A |
| The compound in Example 26 | B | B |
| The compound in Example 31 | B | B |
| The compound in Example 34 | A | A |

C: $IC_{50} \geq 100$ nM, B: 20 nM $\leq IC_{50} < 100$ nM, A: $IC_{50} < 20$ nM.

The experimental results showed that the compound of present invention has good anti-tumor activity. Compared with JQ1, dBET1 and ARV-825, the compound of present invention showed better inhibitory activity, anti-proliferation and apoptosis-inducing ability.

Biological Example 2: Study on the Degradation Mechanism of BRD4-PROTAC Protein

The purpose of the experiment: the influence of BRD4-PROTAC on the degradation of the target protein was observed by MG132 pretreatment to study whether the test compound degrade the target protein through the protease degradation pathway.

Experiment Method:

RS4; 11 and MM.1S cells were cultured in vitro and inoculated in 6-well plate. When the cells were grown to about 80%, MG132 was added to a final concentration of 50 uM. 2 Hours later, the compound of Example 1 and the compound of Example 16 were added to a concentration of 100 nM, and the cells was collected after treated for 4 h. The protein was extracted, and Westing Bloting was performed to detect the BRD4 protein level.

Figure 2:
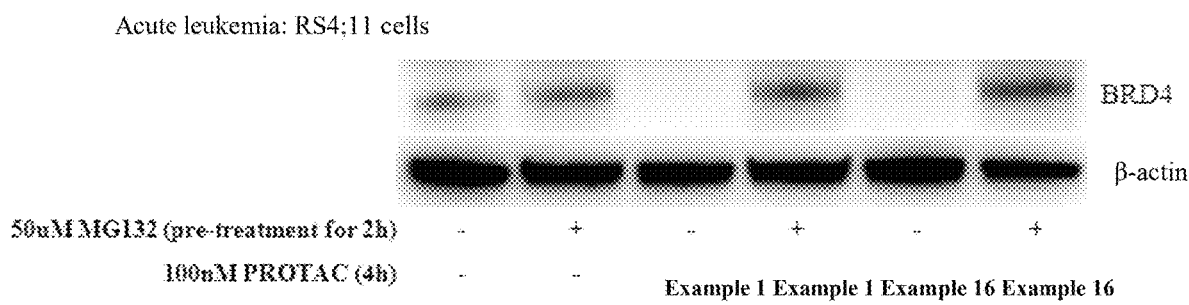
FIG. 2 shows the BRD4-PROTAC protein degradation mechanism of the compound of the present invention.
Figure 2:
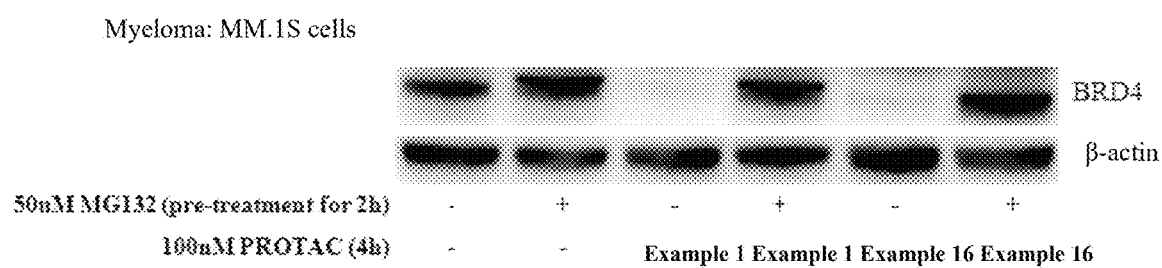

The experimental results were shown in FIG. 2.

The experimental results showed that the compound of the present invention could effectively degrade various tumor cell target protein BRD4; and the protein degradation could be blocked by MG-132, which indicates that the protein degradation of the compound of the present invention was dependent on the ubiquitination-proteasome pathway.

The embodiments of the present invention have been described above. However, the present invention is not limited to the above-mentioned embodiment. Any modification, equivalent replacement, or improvement made within the spirit and principle of the present invention should be included in the protection scope of the present invention.

The invention claimed is:

1. A compound of formula (I) or a tautomer, optical isomer, solvate, or pharmaceutically acceptable salt thereof;

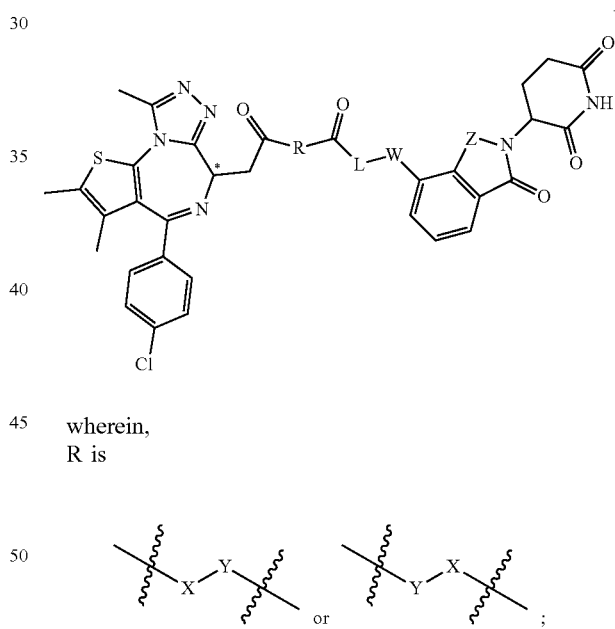

I wherein,
R is

X is amino or substituted amino, wherein the substituent is $C_{1-6}$ alkyl and $C_{1-6}$ alkoxy;
Y is amino, substituted or unsubstituted saturated 5-7 membered heterocycle, saturated heterospirocycle, 5-7 membered saturated bicyclic hetrocycle or 5-6 membered heteroaryl;
the heteroatoms of saturated 5-7 membered heterocycloalkyl is selected from O, N and S, wherein the number of N heteroatom is 1, 2, or 3, and the number of O or S heteroatom is 0, 1, or 2, the substituted saturated 5-7 membered heterocycloalkyl means that the saturated 5-7 membered heterocycloalkyl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl or $C_{5-7}$ heteroaryl;

the saturated heteromonospirocycloalkyl has heteroatoms selected from O, N and S, wherein the number of N heteroatom is 1, 2 or 3, the number of O or S heteroatoms is 0, 1, or 2, and the saturated heteromonospirocycloalkyl is selected from the group consisting of 3-membered/S-membered, 4-membered/4-membered, 4-membered/5-membered, 4-membered/6-membered, 5-membered/5-membered, and 5-membered/6-membered ring, the substituted saturated heteromonospirocycloalkyl means that the saturated heteromonospirocycloalkyl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl or $C_{5-7}$ heteroaryl;

the saturated heterofused cycloalkyl contains one or two heteroatoms independently selected from O, N and S in addition to carbon atoms, and the saturated heterofused cycloalkyl is selected from the group consisting of 5-membered/5-membered and 5-membered/6-membered bicyclic fused heterocyclic group, the substituted saturated heterofused cycloalkyl means that the saturated heterofused cycloalkyl is independently substituted with one or more substituents selected from halogen, hydroxy, cyano, nitro, amino, carbonyl, $C_{1-4}$ alkoxy, $C_{1-4}$ alkyl, $C_{3-8}$ cycloalkyl, aryl and $C_{5-7}$ heteroaryl;

the heteroaryl group contains one or two heteroatoms independently selected from O, N and S in addition to carbon atoms, the substituted heteroaryl means that the heteroaryl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;

L is —(CH$_2$)$_n$—, —CH$_2$CH$_2$(OCH$_2$CH$_2$)$_m$— or —CH$_2$R$_1$—, n is 1, 2, 3, 4, 5 or 6;

m is 1, 2, 3 or 4;

R$_1$ is selected from optionally substituted cycloalkyl, heterocycloalkyl, haloheterocycloalkyl, aryl or heteroaryl; the substituent is independently selected from one or more groups selected from halogen, hydroxyl, cyano, nitro, $C_{1-6}$ alkyl, $C_{1-6}$ alkoxy, haloheterocycloalkyl, aryl and heteroaryl;

W is —CH$_2$—, —NH—, —O—, —CONH— or —COO—;

Z is —CH$_2$— or —CO—.

2. The compound of formula (I) or a tautomer, optical isomer, solvate, or pharmaceutically acceptable salt thereof according to claim 1;

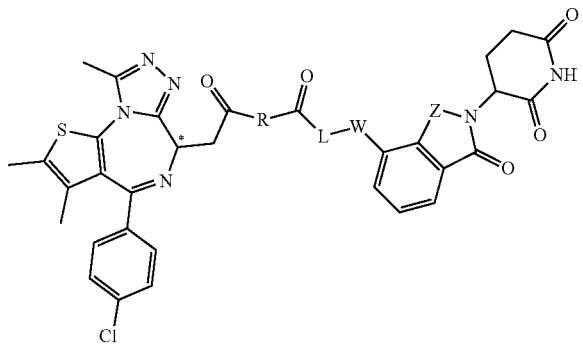

wherein,
R is

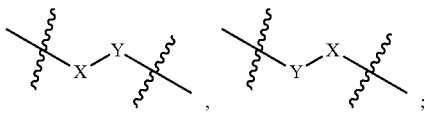

X is amino or substituted amino, and the substituent is selected from $C_{1-6}$ alkyl and $C_{1-6}$ alkoxy;

Y is amino, substituted or unsubstituted saturated 5-7 membered heterocycloalkyl, saturated heteromonospirocycloalkyl, saturated heterofused cycloalkyl or heteroaryl;

the substituted or unsubstituted saturated 5-7 membered heterocycloalkyl has heteroatoms selected from O, N and S, wherein the number of N heteroatom is 1, 2 or 3, and the number of O or S heteroatom is 1 or 2, the substituted saturated 5-7 membered heterocycloalkyl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;

the substituted or unsubstituted saturated heteromonospirocycloalkyl has heteroatoms selected from O, N and S, wherein the number of N heteroatom is 1, 2 or 3, the number of O or S heteroatoms is 1 or 2, and the saturated heteromonospirocycloalkyl is selected from the group consisting of 3-membered/5-membered, 4-membered/4-membered, 4-membered/5-membered, 4-membered/6-membered, 5-membered/5-membered, and 5-membered/6-membered ring, which is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;

the substituted or unsubstituted saturated heterofused cycloalkyl contains one or two heteroatoms independently selected from O, N and S in addition to carbon atoms, and the saturated heterofused cycloalkyl is selected from the group consisting of 5-membered/5-membered and 5-membered/6-membered bicyclic fused heterocyclic group, which is independently substituted with one or more substituents selected from halogen, hydroxy, cyano, nitro, amino, carbonyl, $C_{1-4}$ alkoxy, $C_{1-4}$ alkyl, $C_{3-8}$ cycloalkyl, aryl and $C_{5-7}$ heteroaryl;

the heteroaryl group contains one or two heteroatoms independently selected from O, N and S in addition to carbon atoms, the heteroaryl is independently substituted with one or more substituents selected from halogen, hydroxy, cyano, nitro, amino, carbonyl, $C_{1-6}$ alkoxy, $C_{1-6}$ alkyl, $C_{3-8}$ cycloalkyl, aryl and $C_{5-7}$ heteroaryl;

L is —$(CH_2)_n$—, —$CH_2CH_2(OCH_2CH_2)_m$— or —$CH_2R_1$—;

n is 1, 2, 3, 4, 5 or 6;

m is 1, 2, 3 or 4;

$R_1$ is optionally substituted cycloalkyl, heterocycloalkyl, haloheterocycloalkyl, aryl or heteroaryl; the substituent is independently selected from one or more groups consisting of halogen, hydroxyl, cyano, nitro, $C_{1-6}$ alkyl, $C_{1-6}$ alkoxy, haloheterocycloalkyl, aryl or heteroaryl;

W is —$CH_2$—, amino, —O—, —CONH— or —COO—;

Z is —$CH_2$— or —CO—.

3. The compound of formula (I) or a tautomer, optical isomer, solvate, or pharmaceutically acceptable salt thereof according to claim 1, wherein X is amino; Y is amino, or substituted or unsubstituted saturated 5-7 membered heterocycloalkyl.

4. The compound of formula (I) or a tautomer, optical isomer, solvate, or pharmaceutically acceptable salt thereof according to claim 1, wherein X is amino; Y is amino or piperazinyl.

5. The compound of formula (I) or a tautomer, optical isomer, solvate, or pharmaceutically acceptable salt thereof according to claim 1, wherein L is —$(CH_2)_n$—, —$CH_2CH_2(OCH_2CH_2)_m$—, n is 1, 2, 3, 4, 5 or 6; m is 1, 2, 3 or 4.

6. The compound of formula (I) or a tautomer, optical isomer, solvate, or pharmaceutically acceptable salt thereof according to claim 1, wherein the configuration of "*" in the compound of formula (I) is S type.

7. The compound of formula (I) or a tautomer, optical isomer, solvate, or pharmaceutically acceptable salt thereof according to claim 1, wherein the compound is selected from the following:

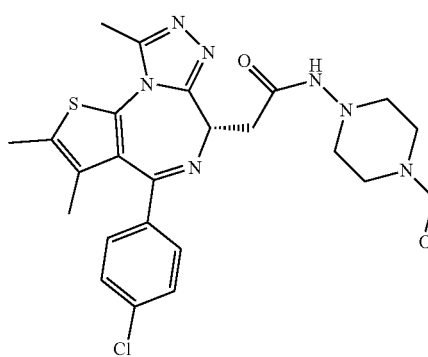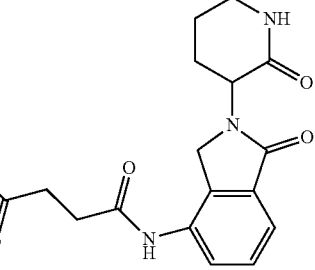

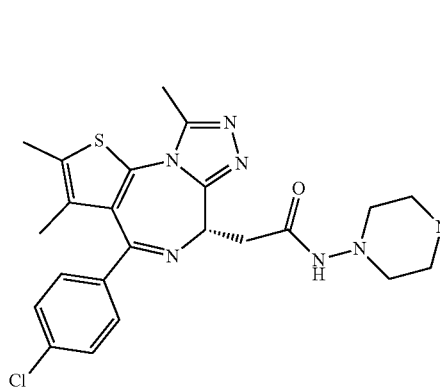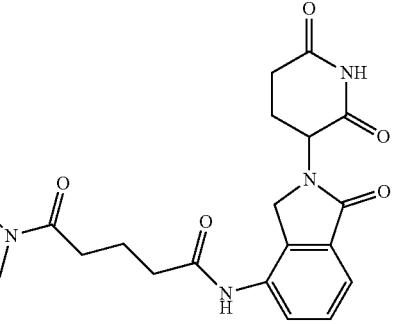

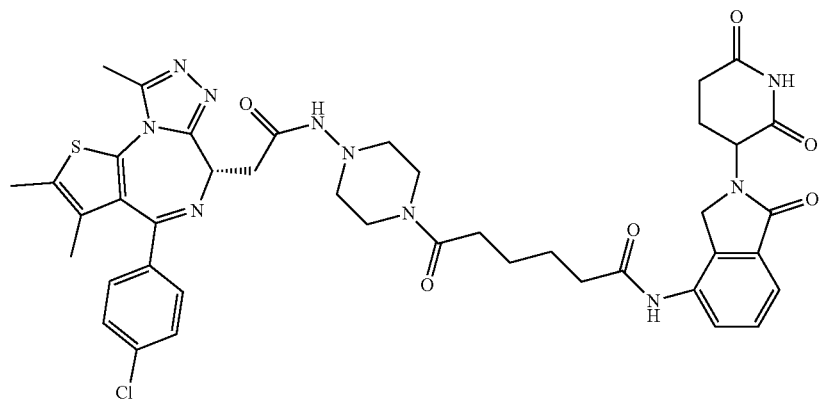
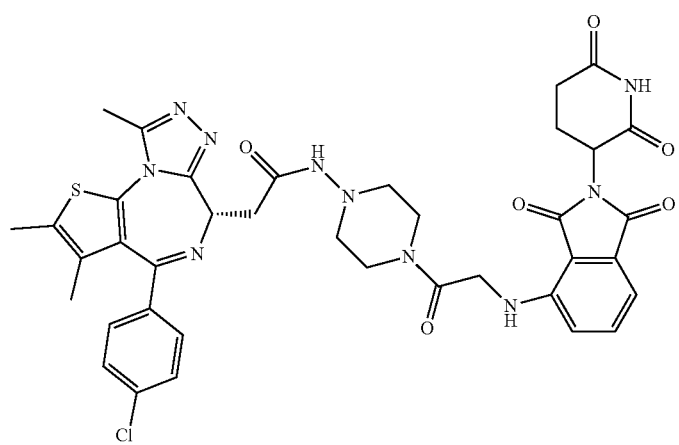
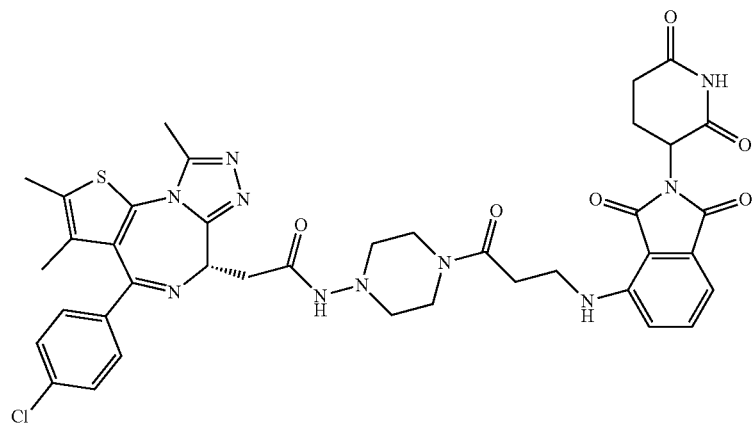
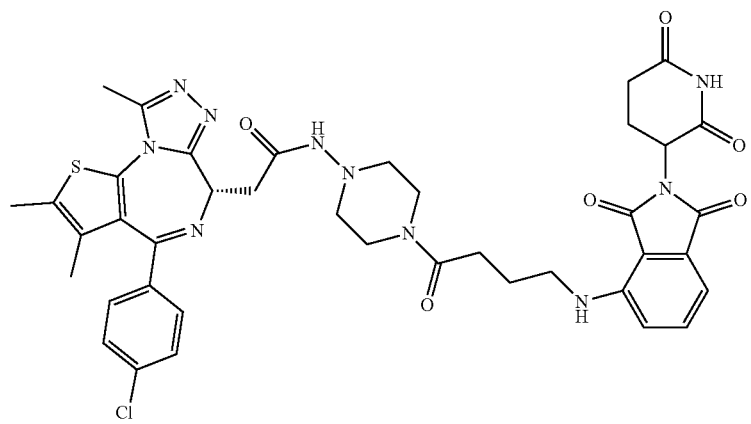

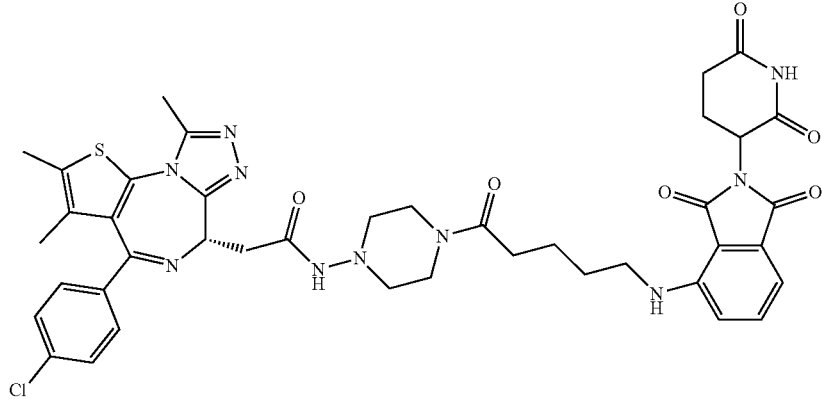
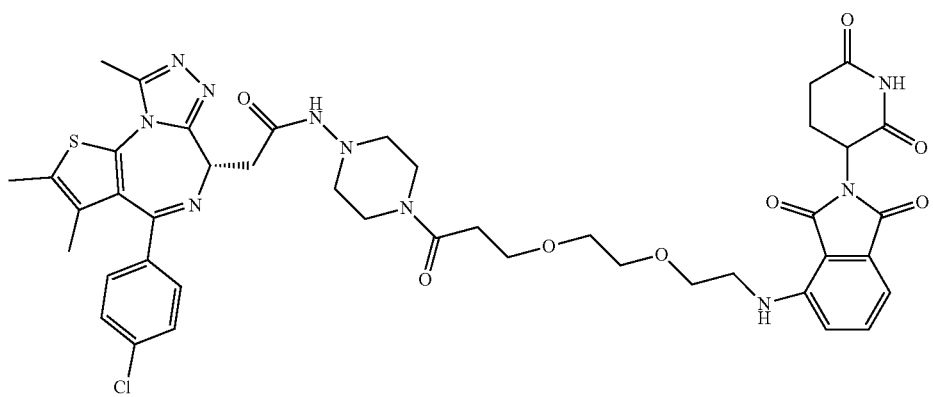
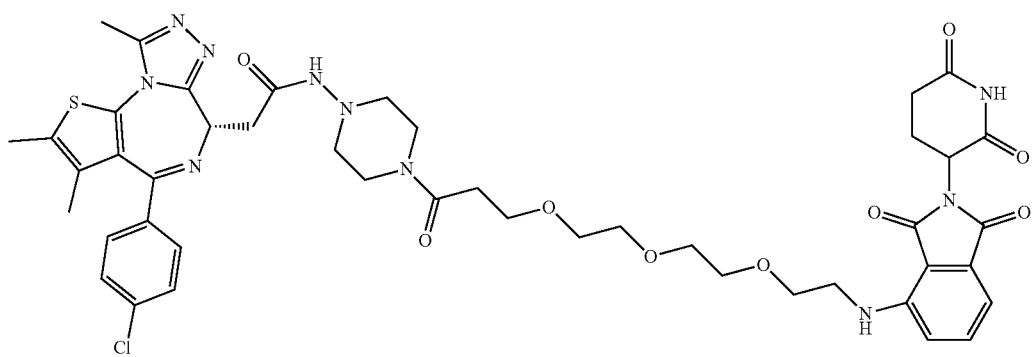
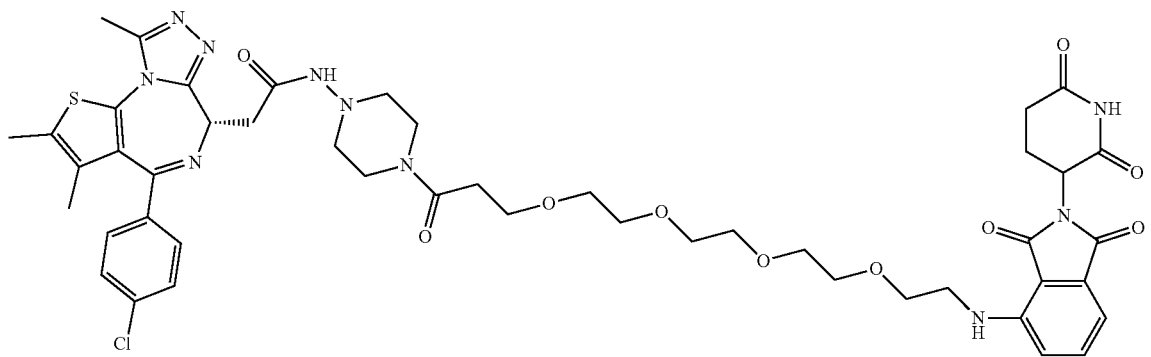

-continued
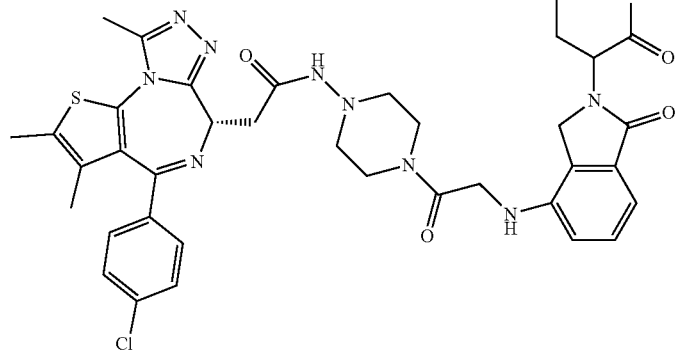
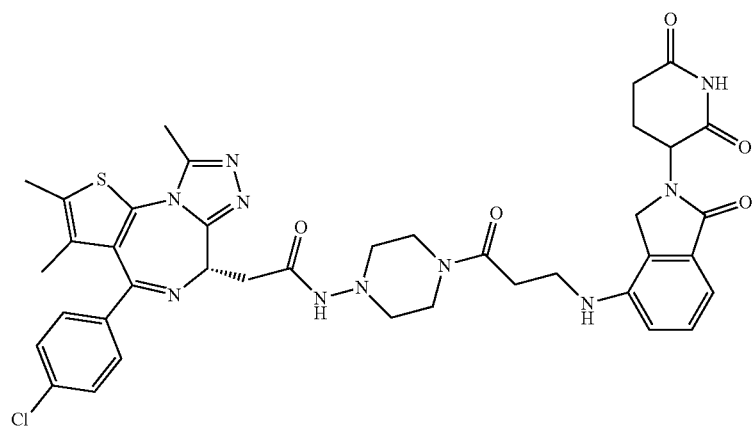
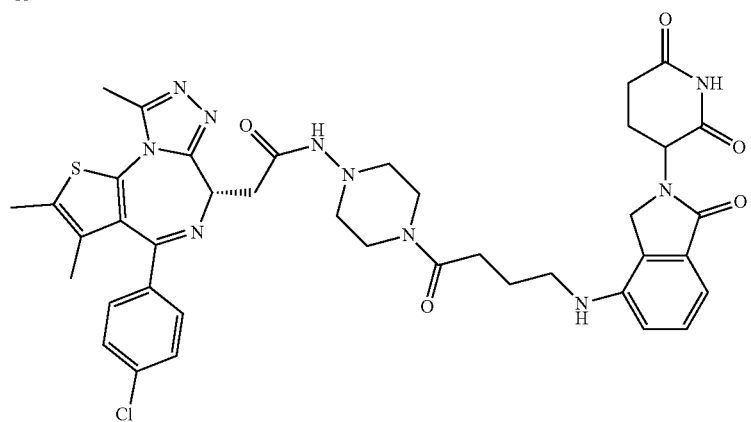
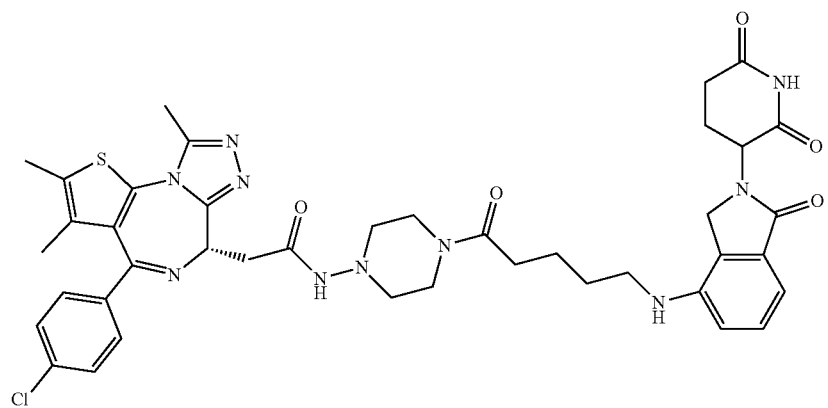

-continued
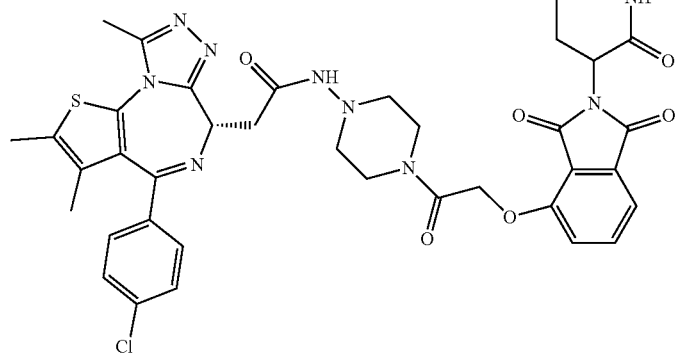
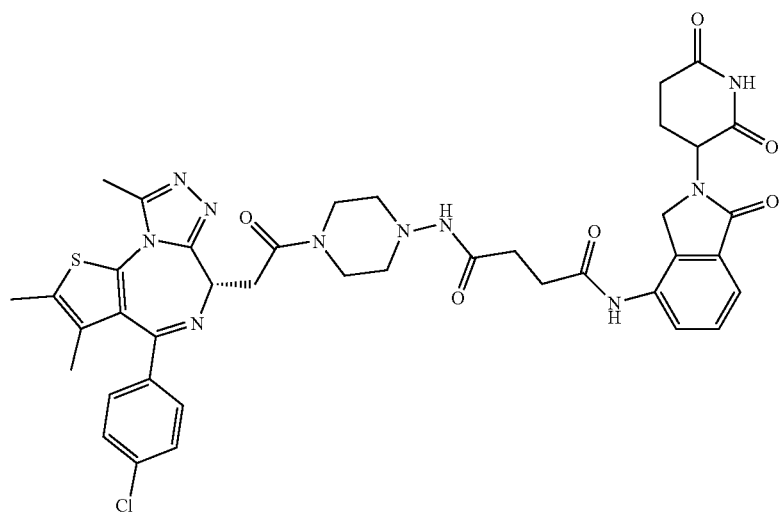
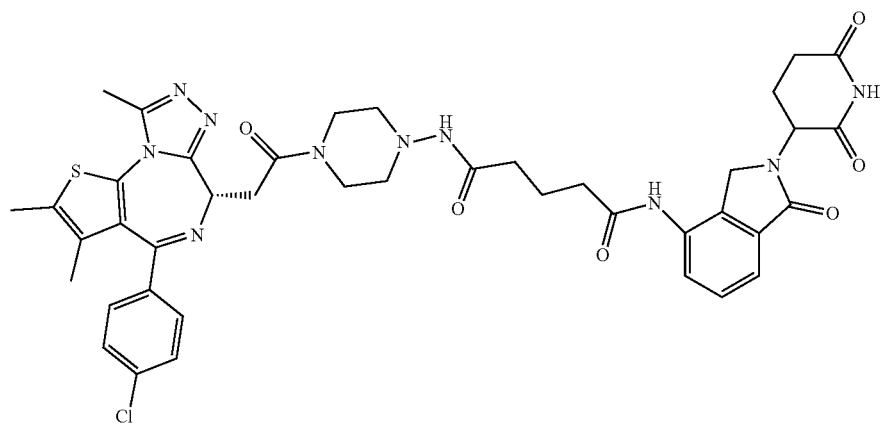

-continued
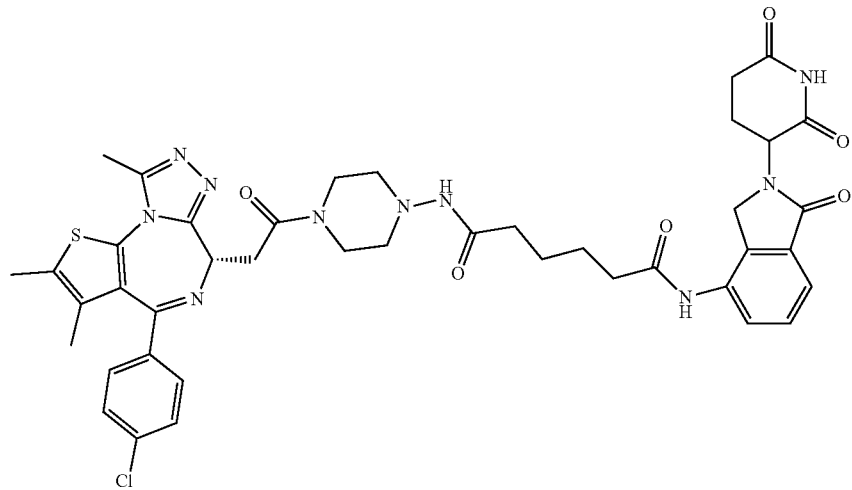
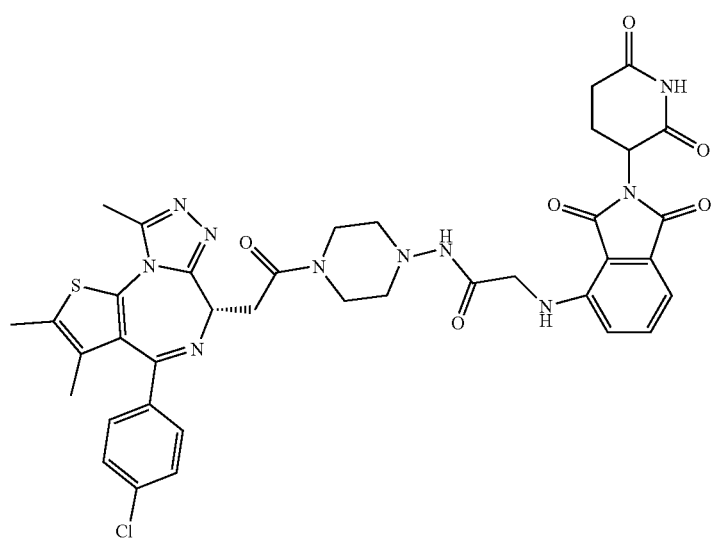
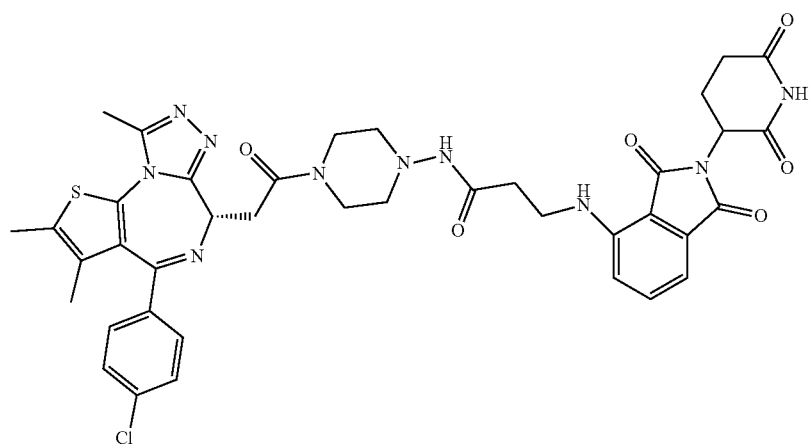

-continued
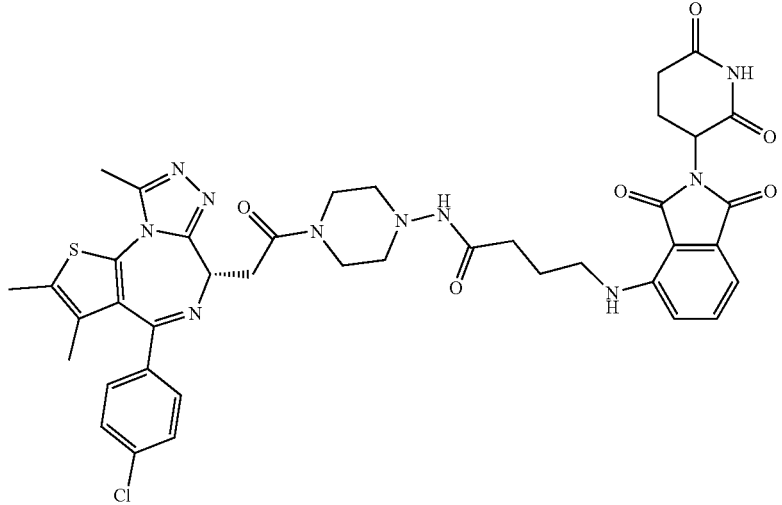
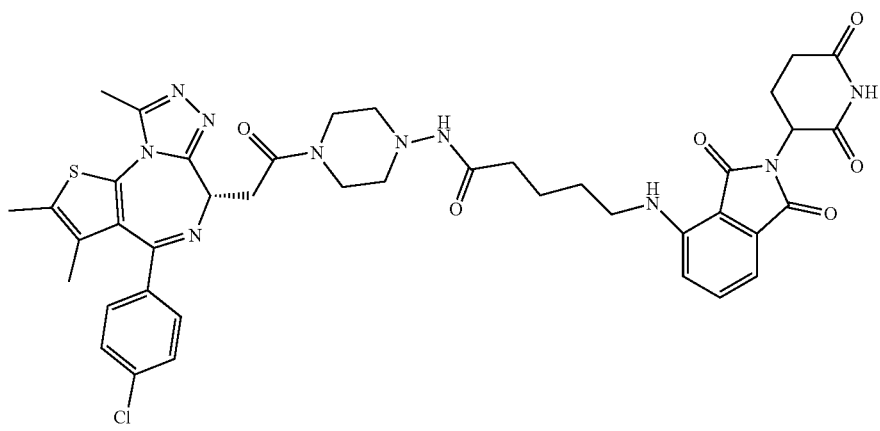
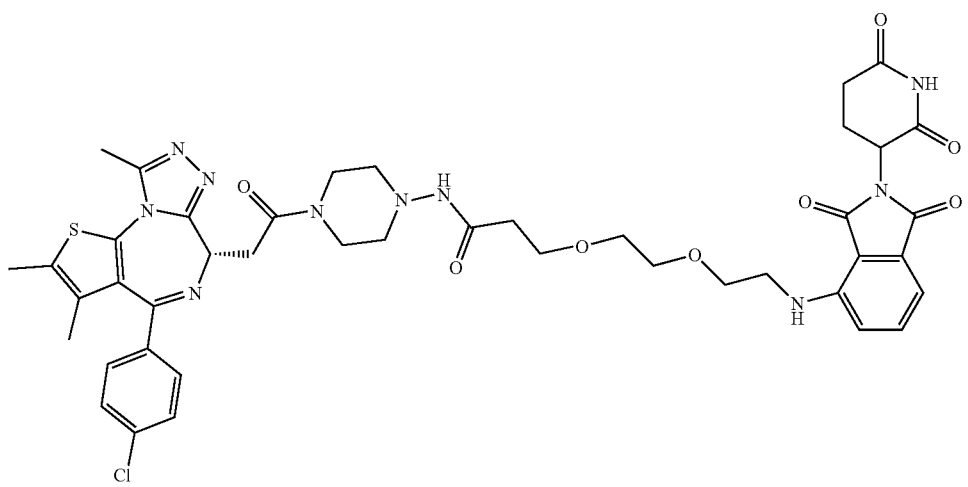

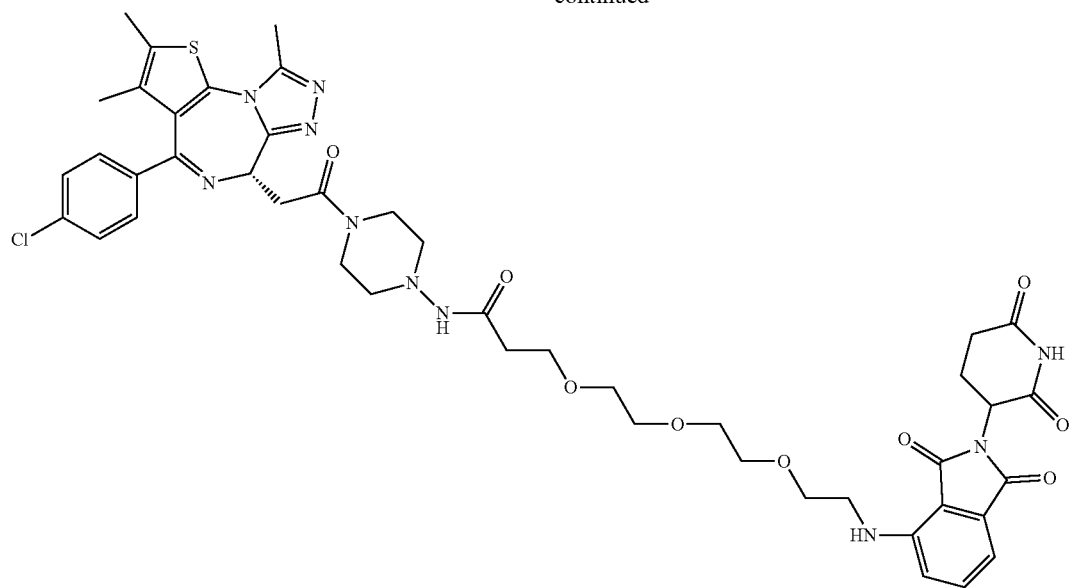
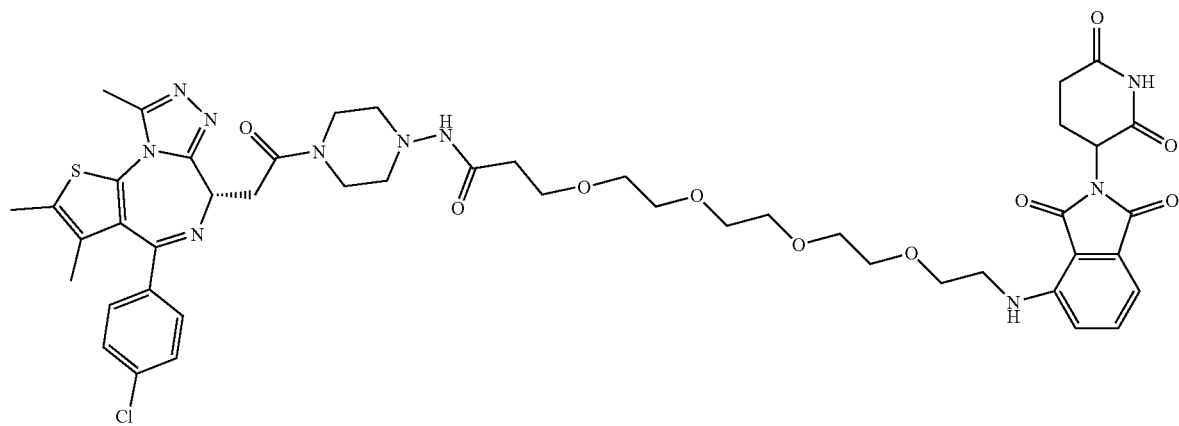
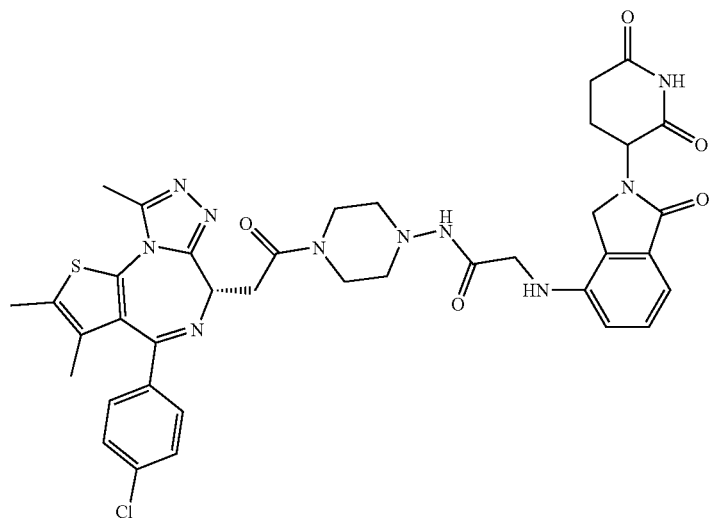

-continued
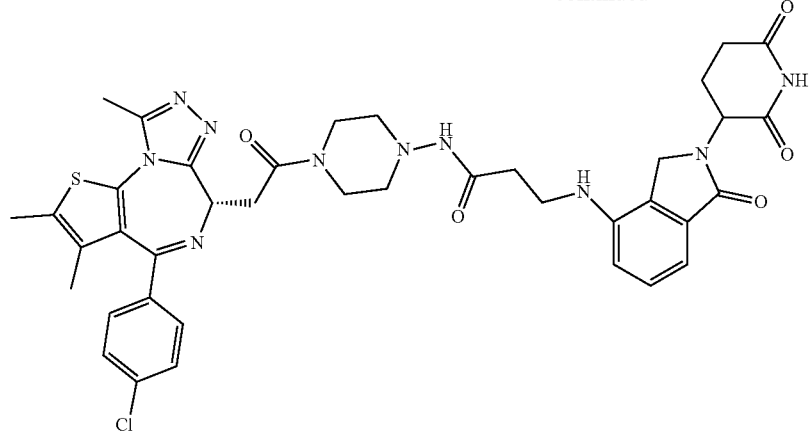
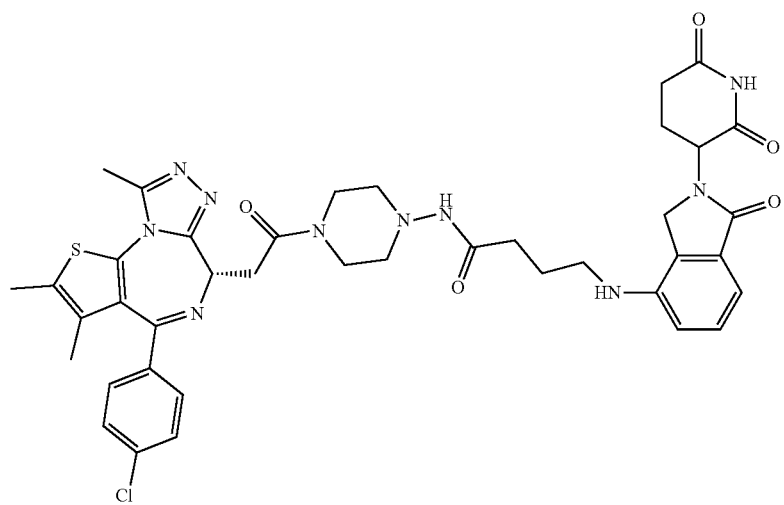
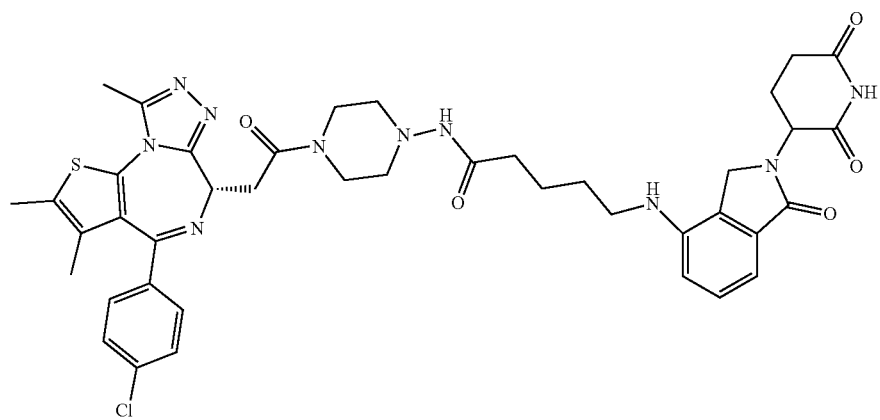

-continued
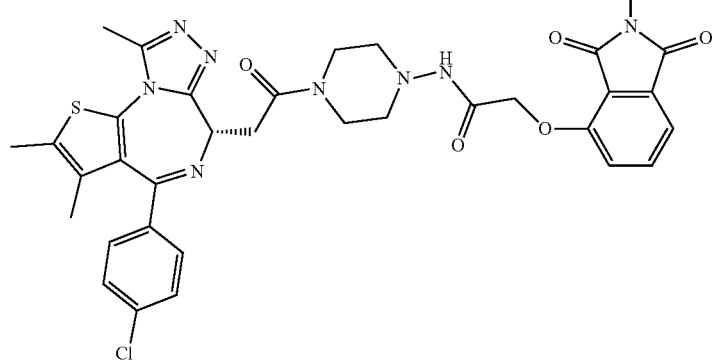
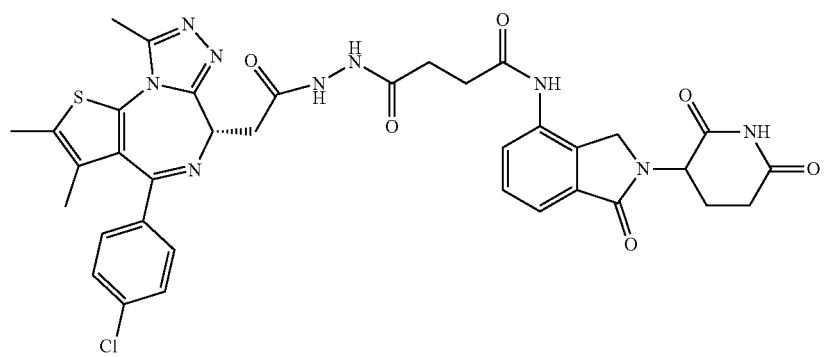
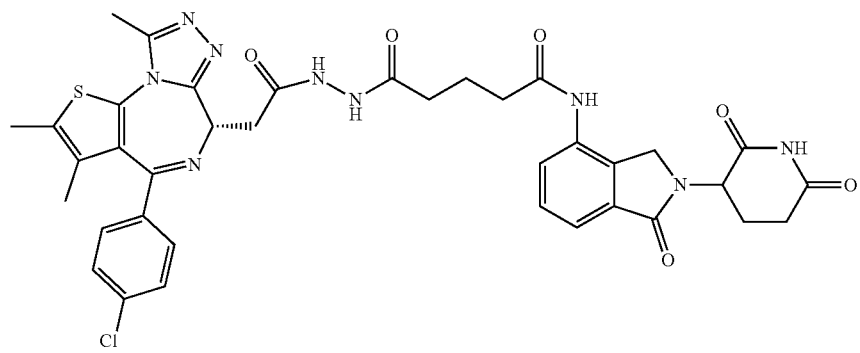
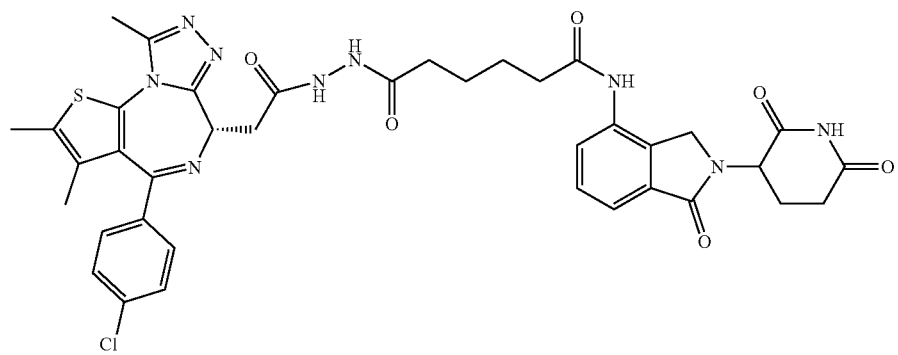

-continued
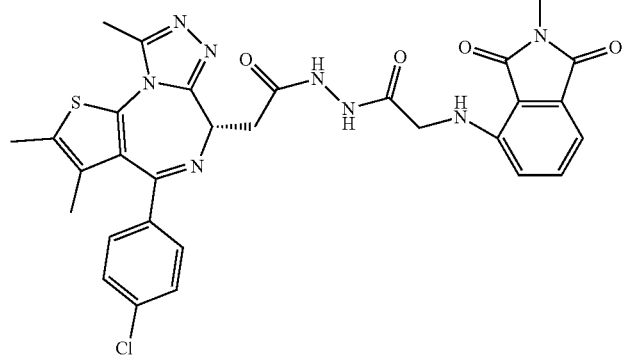
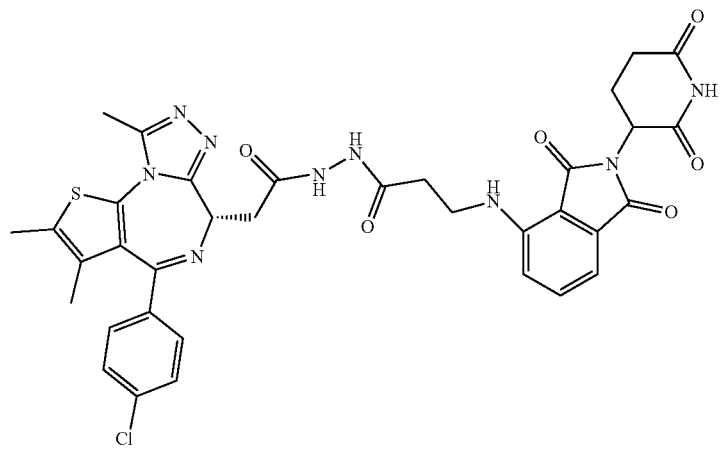
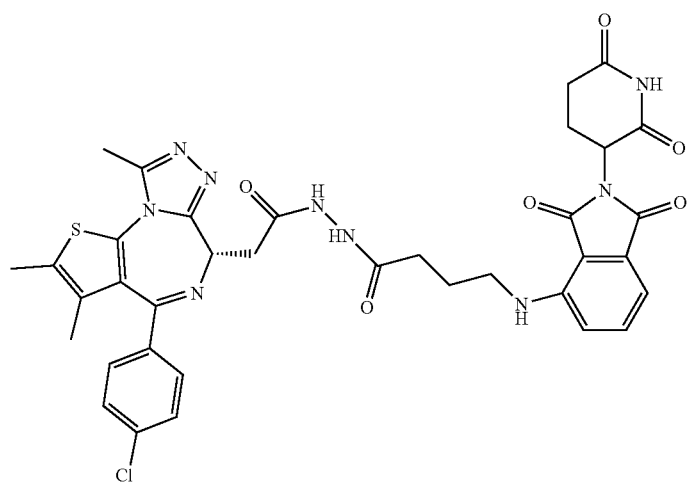

-continued
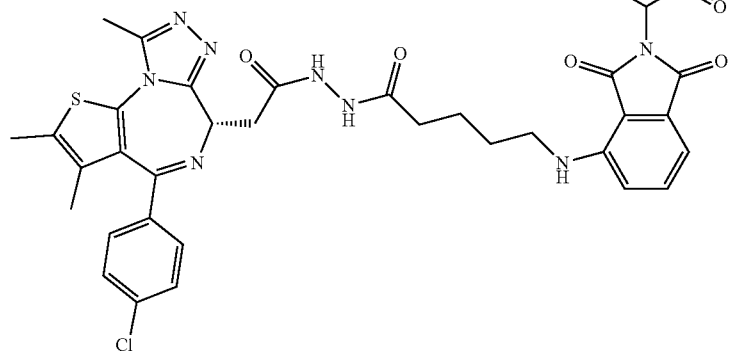
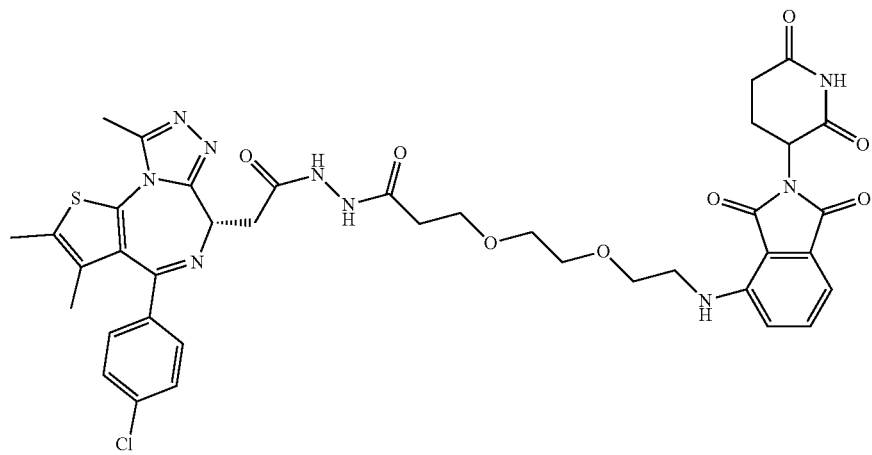
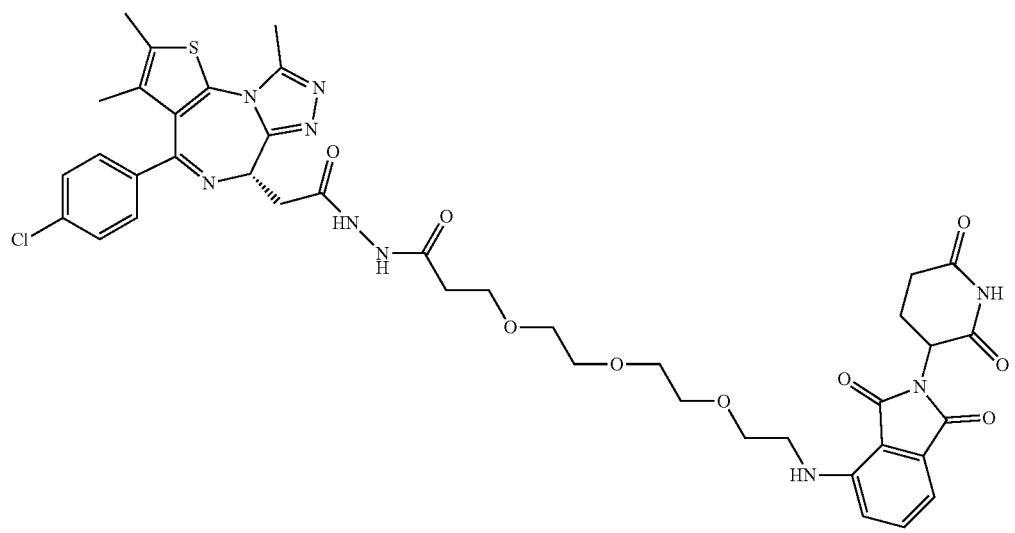

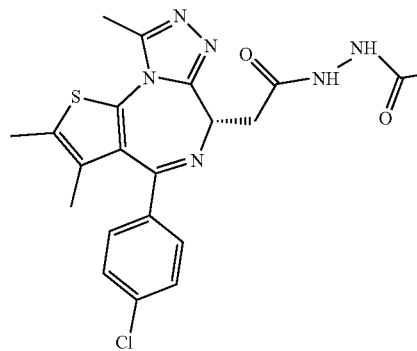
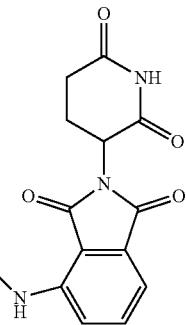
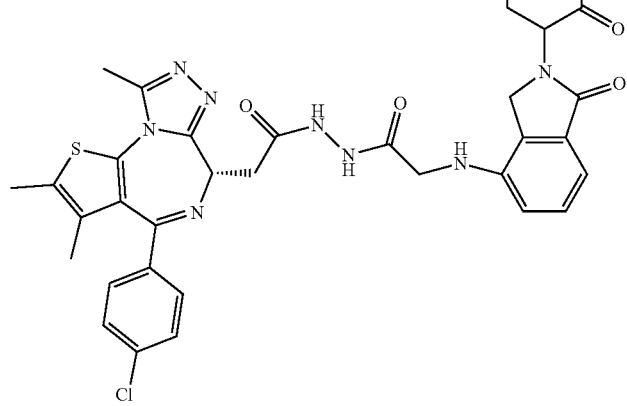
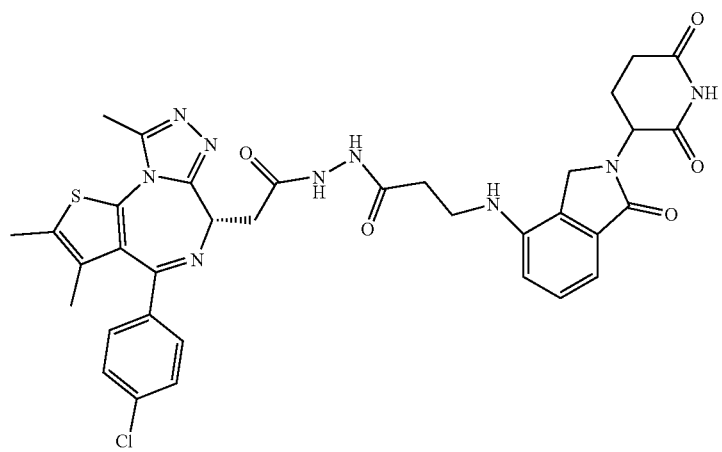

-continued
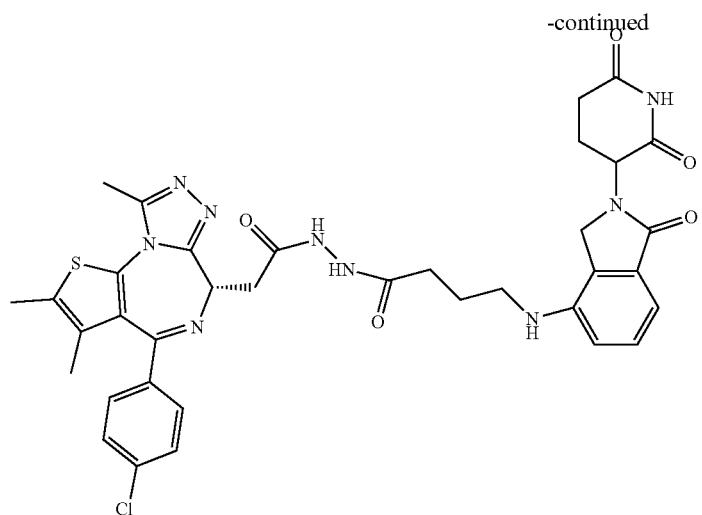
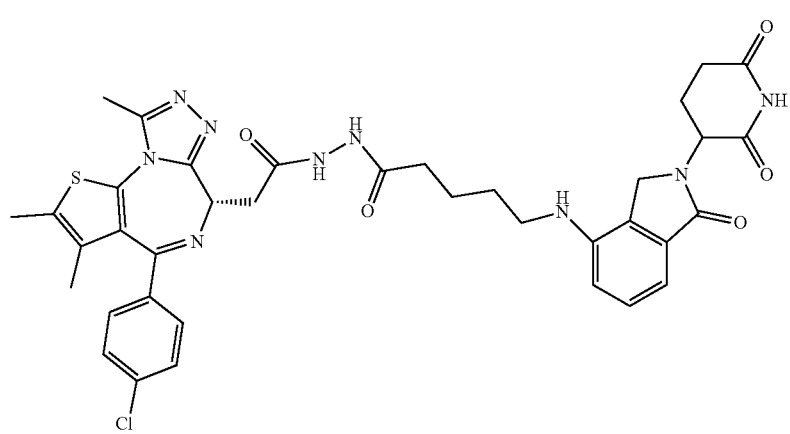
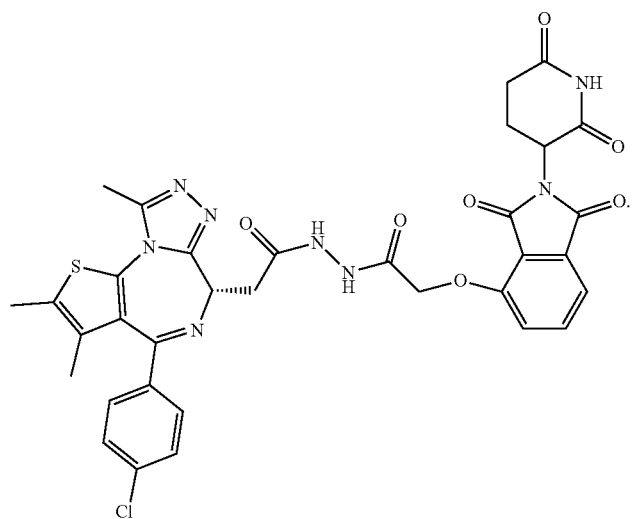
8. A pharmaceutical composition comprising the compound of formula (I) or a tautomer, optical isomer, solvate, or pharmaceutically acceptable salt thereof according to claim 1.

9. A method for preparing the compound of formula (I) or a tautomer, optical isomer, solvate, or pharmaceutically acceptable salt thereof according to claim 1, comprising subjecting the compound of formula (M) and the compound of formula (C) to condensation reaction to afford the compound of formula (I),
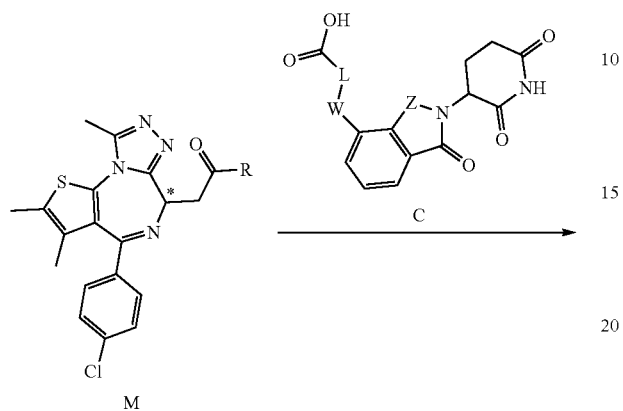
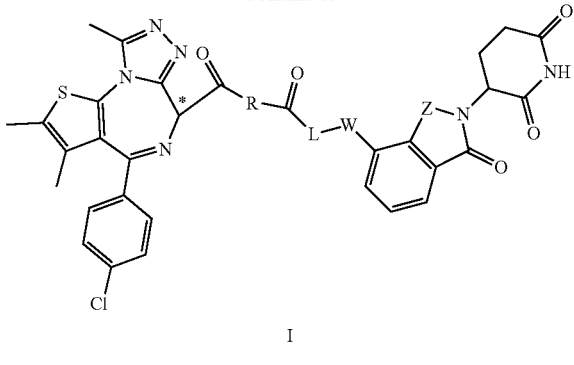
wherein, R, L, W and Z are as defined in claim 1.
* * * * *